(12) United States Patent
Leksic et al.

(10) Patent No.: US 7,956,048 B2
(45) Date of Patent: Jun. 7, 2011

(54) POLYMORPHS OF ELTROMBOPAG AND ELTROMBOPAG SALTS AND PROCESSES FOR PREPARATION THEREOF

(75) Inventors: Edislav Leksic, Zagreb (HR); Helena Ceric, Zagreb (HR); Tina Mundorfer, Zagreb (HR); Irena Zrinski Antonac, Zagreb (HR); Zrinka Mastelic Samardzic, Zagreb (HR)

(73) Assignee: Pliva Hrvatska D.O.O., Zabreb (HR)

( * ) Notice: Subject to any disclaimer, the term of this patent is extended or adjusted under 35 U.S.C. 154(b) by 0 days.

(21) Appl. No.: 12/752,642

(22) Filed: Apr. 1, 2010

(65) Prior Publication Data

US 2010/0256212 A1    Oct. 7, 2010

Related U.S. Application Data

(60) Provisional application No. 61/165,638, filed on Apr. 1, 2009, provisional application No. 61/167,297, filed on Apr. 7, 2009, provisional application No. 61/171,894, filed on Apr. 23, 2009, provisional application No. 61/177,019, filed on May 11, 2009, provisional application No. 61/180,961, filed on May 26, 2009, provisional application No. 61/223,685, filed on Jul. 7, 2009, provisional application No. 61/266,364, filed on Dec. 3, 2009.

(51) Int. Cl.
*C07D 231/46* (2006.01)
*A61K 31/4152* (2006.01)
*A61K 31/655* (2006.01)

(52) U.S. Cl. ...... 514/150; 514/404; 534/792; 548/367.4

(58) Field of Classification Search .................. None
See application file for complete search history.

(56) References Cited

U.S. PATENT DOCUMENTS

| 7,160,870 B2 | 1/2007 | Duffy et al. |
| 7,332,481 B2 | 2/2008 | Duffy et al. |
| 7,547,719 B2 * | 6/2009 | Moore .......................... 514/404 |
| 7,795,293 B2 * | 9/2010 | Moore .......................... 514/404 |
| 2004/0019190 A1 | 1/2004 | Erickson-Miller et al. |
| 2006/0178518 A1 | 8/2006 | Moore |

FOREIGN PATENT DOCUMENTS

| EP | 1 294 378 | 10/2007 |
| WO | WO 01/89457 | 11/2001 |
| WO | WO 03/098992 | 12/2003 |

OTHER PUBLICATIONS

M.R. Caira "Crystalline Polymorphism of Organic Compounds" Topics in Current Chemistry, vol. 198, p. 163-208, (1998) XP001156954.

* cited by examiner

*Primary Examiner* — Fiona T Powers
(74) *Attorney, Agent, or Firm* — Merchant & Gould PC

(57) ABSTRACT

New polymorphs of Eltrombopag and Eltrombopag ethanolamine salt have been obtained and characterized. These polymorphs and pharmaceutical compositions comprising them are useful, for example, in treating conditions leading to thrombocytopenia.

17 Claims, 40 Drawing Sheets

POLYMORPHS OF ELTROMBOPAG AND ELTROMBOPAG SALTS AND PROCESSES FOR PREPARATION THEREOF

CROSS-REFERENCE TO RELATED APPLICATIONS

This application claims the benefit of U.S. Provisional Patent Application Ser. Nos. 61/165,638; filed Apr. 1, 2009; 61/167,297, filed Apr. 7, 2009; 61/171,894, filed Apr. 23, 2009; 61/177,019, filed May 11, 2009; 61/180,961, filed May 26, 2009; 61/223,685, filed Jul. 7, 2009; and 61/266,364, filed Dec. 3, 2009, all of which are incorporated herein by reference.

FIELD OF THE INVENTION

The present invention relates to polymorphs of Eltrombopag and Eltrombopag ethanolamine salt, preparation of these polymorphs and pharmaceutical compositions comprising them.

BACKGROUND OF THE INVENTION

Eltrombopag, (Z)-3'-(2-(1-(3,4-dimethylphenyl)-3-methyl-5-oxo-1H-pyrazol-4(5H)-ylidene)hydrazinyl)-2'-hydroxybiphenyl-3-carboxylic acid is a compound having the following chemical structure:

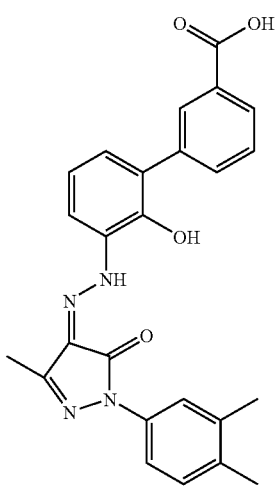

It is a small-molecule, non-peptide thrombopoitin (TPO) receptor agonist that stimulates the proliferation and differentiation of megakaryocytes.

Eltrombopag is marketed under the trade name Promacta® by GlaxoSmithKline and Ligand Pharmaceuticals as a bisethanolamine salt of the following chemical structure:

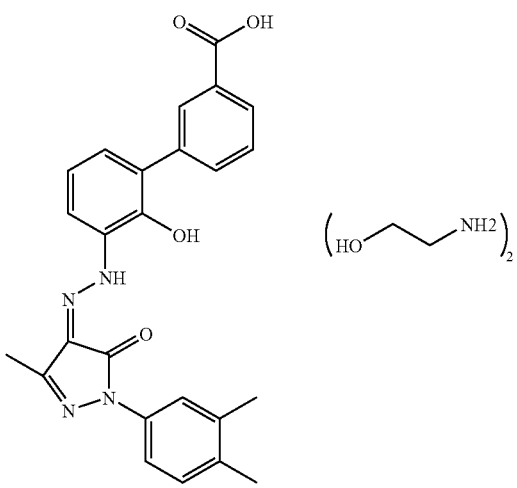

for the treatment of conditions leading to thrombocytopenia.

Eltrombopag is disclosed in U.S. Pat. Nos. 7,332,481 and 7,160,870; WO patent application 01/89457; and in EP patent No. 1294378.

Eltrombopag bisethanolamine salt is disclosed in US 2006/0178518 (corresponding to WO 03/098992).

Polymorphism, the occurrence of different crystal forms, is a property of some molecules and molecular complexes. A single molecule may give rise to a variety of polymorphs having distinct crystal structures and physical properties like melting point, thermal behaviours (e.g. measured by thermogravimetric analysis—"TGA", or differential scanning calorimetry—"DSC"), x-ray diffraction pattern, infrared absorption fingerprint, and solid state NMR spectrum. One or more of these techniques may be used to distinguish different polymorphic forms of a compound.

Discovering new polymorphic forms and solvates of a pharmaceutical product can provide materials having desirable processing properties, such as ease of handling, ease of processing, storage stability, and ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life. For at least these reasons, there is a need for additional polymorphs of Eltrombopag and Eltrombopag ethanolamine salt.

SUMMARY OF THE INVENTION

The present invention provides crystalline forms of Eltrombopag, Eltrombopag bisethanolamine and monoethanolamine salts, and processes for preparing them.

In one embodiment the present invention encompasses crystalline Eltrombopag designated form I characterized by a data selected from a group consisting of: powder XRD pattern having peaks at 4.0, 7.3, 7.7, 12.1 and 16.1° 2θ±0.2° 2θ; a PXRD pattern as depicted in FIG. 1; a solid state $^{13}$C NMR spectrum having peaks at 166.9, 155.4, 134.1, 125.7 and 111.8±0.2 ppm; a solid state $^{13}$C NMR spectrum as depicted in FIG. 35; and any combination thereof.

In another embodiment the present invention encompasses crystalline Eltrombopag designated form III characterized by data selected from a group consisting of: powder XRD pattern having peaks at 9.2, 11.2, 12.2 and 14.0° 2θ±0.2° 2θ; a PXRD pattern as depicted in FIG. 3; a solid state $^{13}$C NMR spectrum having peaks at 170.6, 128.7, 124.2 and 113.8±0.2 ppm; a solid state $^{13}$C NMR spectrum as depicted in FIG. 36; and any combination thereof.

In yet another embodiment the present invention encompasses crystalline Eltrombopag designated form V characterized by data selected from a group consisting of: powder XRD pattern having peaks at 5.9, 8.2, 10.5 and 12.5° 2θ±0.2° 2θ; a PXRD pattern as depicted in FIG. 7; a solid state $^{13}$C NMR spectrum having peaks at 142.0, 131.6, 114.9 and 67.8±0.2 ppm; a solid state $^{13}$C NMR spectrum as depicted in FIG. 37; and any combination thereof.

In one embodiment the present invention encompasses crystalline Eltrombopag designated form XVI characterized by a data selected from a group consisting of: powder XRD pattern having peaks at 7.1, 9.5, 13.9, 21.2 and 25.5° 2θ±0.2° 2θ; a PXRD pattern as depicted in FIG. 20; a solid state $^{13}$C NMR spectrum having peaks at 168.7, 156.7, 127.6 and 112.8±0.2 ppm; a solid state $^{13}$C NMR spectrum as depicted in FIG. 38; and any combination thereof.

In another embodiment the present invention encompasses the use of any one, or combination, of the above described crystalline forms of Eltrombopag to prepare Eltrombopag ethanolamine salt, or a formulation thereof.

In yet another embodiment the present invention encompasses a process for preparing Eltrombopag ethanolamine salt comprising preparing any one, or combination, of the above described crystalline forms of Eltrombopag by the processes of the present invention and converting them to Eltrombopag bisethanolamine salt.

In yet another embodiment the present invention encompasses crystalline Eltrombopag bisethanolamine salt designated form II characterized by a data selected from a group consisting of: powder XRD pattern having peaks at 9.3, 11.8, 13.2 and 17.7° 2θ±0.2° 2θ; a PXRD pattern as depicted in FIG. 24; a solid state $^{13}$C NMR spectrum having peaks at 174.9, 147.1, 135.4 and 58.7±0.2 ppm; a solid state $^{13}$C NMR spectrum as depicted in FIG. 39; and any combination thereof.

In one embodiment the present invention encompasses the use the below described crystalline form of Eltrombopag bisethanolamine salt to prepare for the manufacture of a medicament for the treatment of conditions leading to thrombocytopenia.

In another embodiment, the present invention encompasses a pharmaceutical composition comprising at least one of the below described polymorphs of Eltrombopag monoethanolamine and Eltrombopag bisethanolamine salt and at least one pharmaceutically acceptable excipient.

In yet another embodiment the present invention encompasses the use of any one, or combination, of the below described crystalline forms of Eltrombopag monoethanolamine salt to prepare Eltrombopag bisethanolamine salt, and or formulation comprising thereof.

DETAILED DESCRIPTION OF THE INVENTION

The present invention relates to polymorphs of Eltrombopag, Eltrombopag ethanolamine salt, preparation of these polymorphs and pharmaceutical compositions thereof. In particular, the present application provides crystalline forms of Eltrombopag having high chemical purity, which can be used to prepare Eltrombopag salt in high chemical purity.

The present application provides Eltrombopag in a crystalline form, which is exceptionally attractive for making pharmaceutical formulations, as compared to the amorphous forms disclosed in the prior art, which generally demonstrate low purity.

As used herein, and unless stated otherwise, XRPD peaks preferably refer to those measured using Cu radiation at 1.54 angstroms.

As used herein, the term "Room temperature" refers to a temperature between about 20° C. and about 30° C. Usually, room temperature ranges from about 20° C. to about 25° C.

As used herein, the term "Overnight" refers to a period of between about 15 and about 20 hours, typically between about 16 to about 20 hours.

A crystal form may be referred to herein as being characterized by graphical data "as depicted in" a Figure. Such data include, for example, powder X-ray diffractograms and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

A crystal form (or polymorph) may be referred to herein as substantially free of any other crystalline (or polymorphic) forms. As used herein in this context, the expression "substantially free of any other forms" will be understood to mean that the crystalline form contains 20% or less, 10% or less, 5% or less, 2% or less, or 1% or less of any other forms of the subject compound as measured, for example, by XRPD. Thus, polymorphs of Eltrombopag and Eltrombopag ethanolamine salt described herein as substantially free of any other polymorphic forms would be understood to contain greater than 80% (w/w), greater than 90% (w/w), greater than 95% (w/w), greater than 98% (w/w), or greater than 99% (w/w) of the subject polymorphic form of Eltrombopag. Accordingly, in some embodiments of the invention, the described polymorphs of Eltrombopag and Eltrombopag ethanolamine salt may contain from 1% to 20% (w/w), from 5% to 20% (w/w), or from 5% to 10% (w/w) of one or more other crystal forms of Eltrombopag.

The present invention provides crystalline Eltrombopag.

Figure 1:
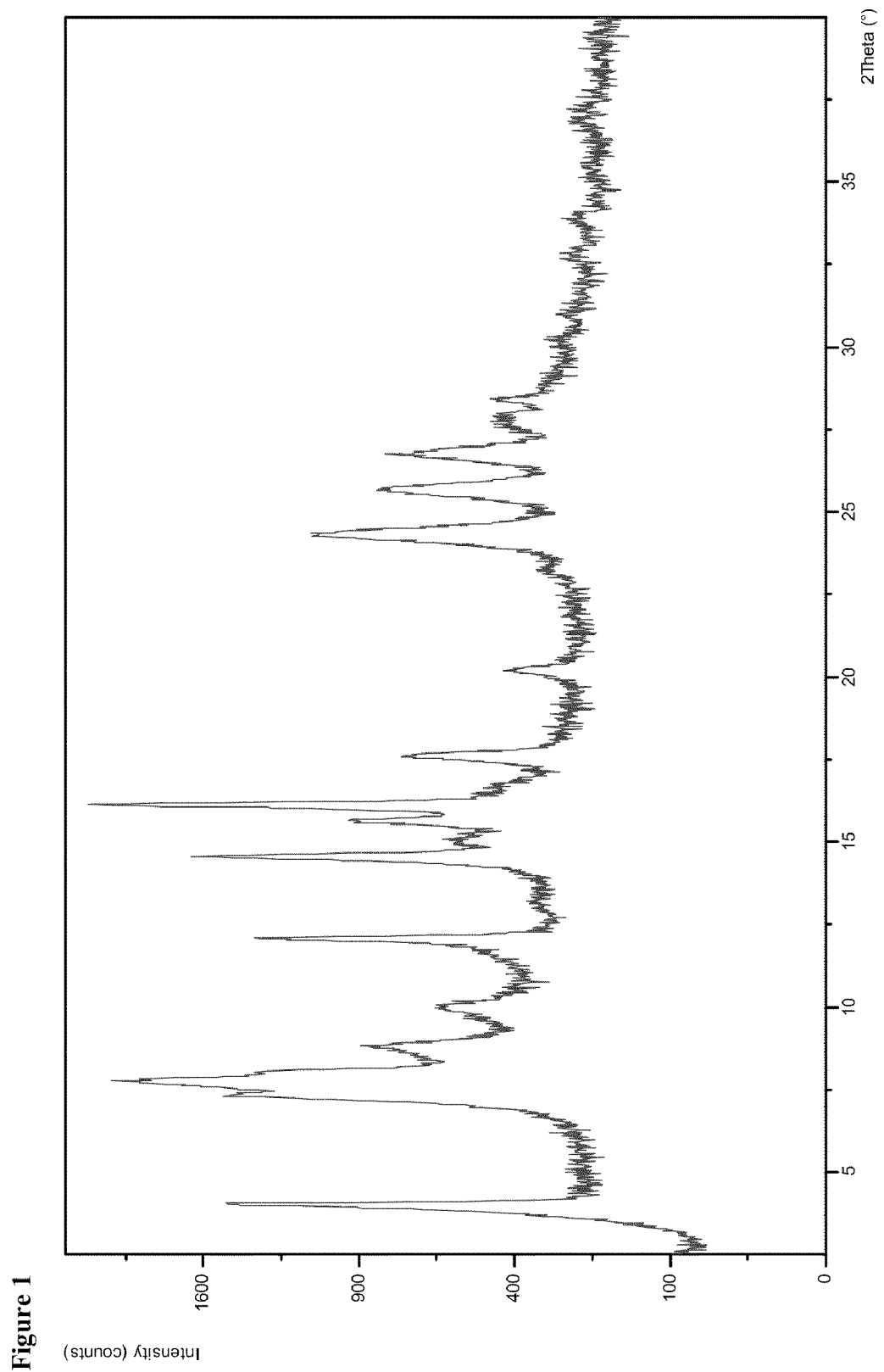
FIG. 1 shows a powder XRD pattern of crystalline Eltrombopag designated form I.
Figure 35:
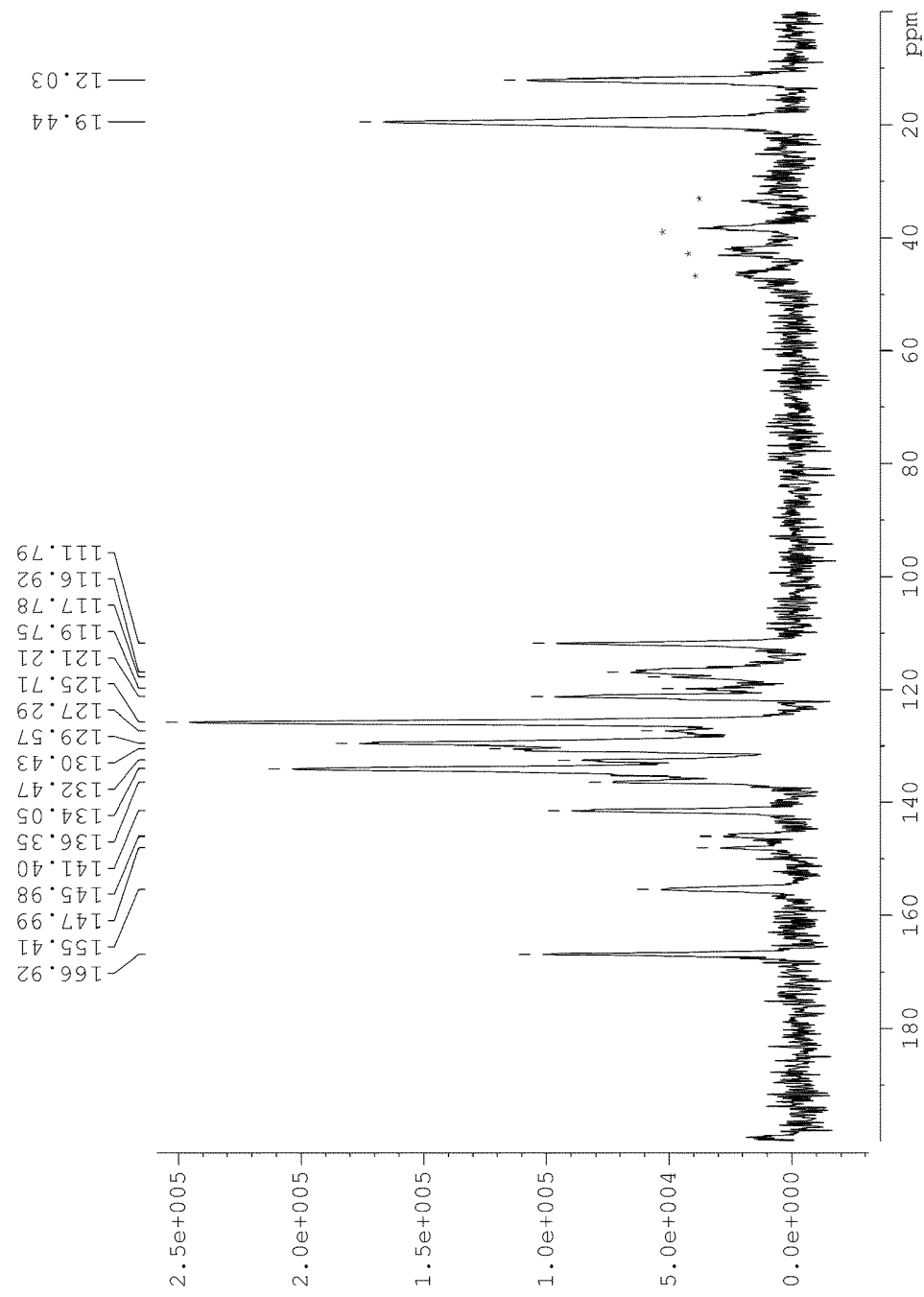
FIG. 35 shows a solid state $^{13}$C NMR spectrum of crystalline Eltrombopag designated form I.

In one embodiment the present invention encompasses crystalline Eltrombopag characterized by data selected from a group consisting of: powder XRD pattern having peaks at 4.0, 7.3, 7.7, 12.1 and 16.1° 2θ±0.2° 2θ; a PXRD pattern as depicted in FIG. 1; a solid state $^{13}$C NMR spectrum having peaks at 166.9, 155.4, 134.1, 125.7 and 111.8±0.2 ppm; a solid state $^{13}$C NMR spectrum as depicted in FIG. 35; and any combination thereof. This crystalline form of Eltrombopag is designated herein as form I.

Figure 2:
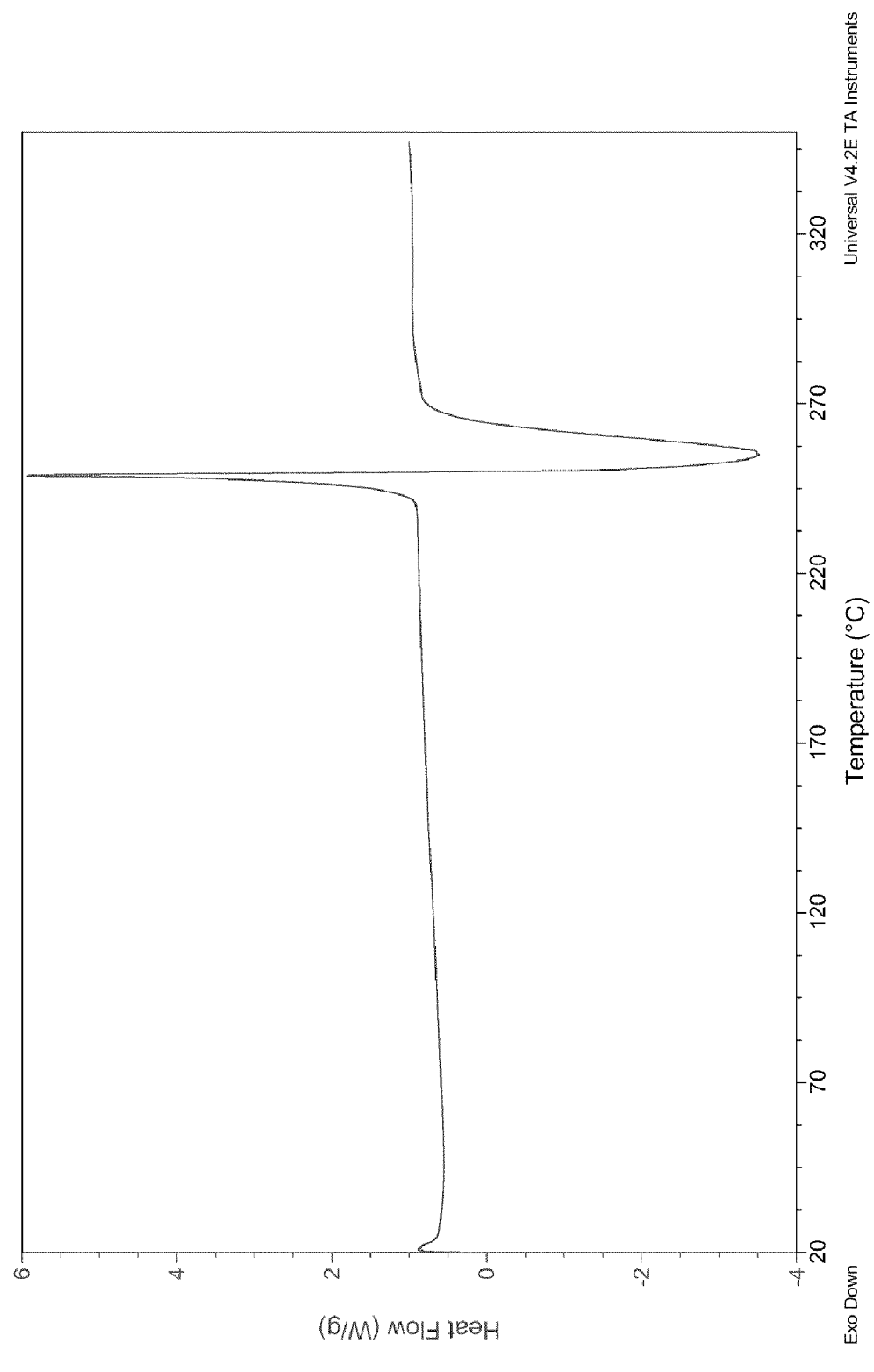
FIG. 2 shows a DSC thermogram of crystalline Eltrombopag designated form I.

The above form I of Eltrombopag can be further characterized by data selected from a group consisting of: a powder XRD pattern having peaks at 8.8, 14.6, 17.6, 24.3 and 26.8° 2θ±0.2° 2θ; a DSC thermogram as depicted in FIG. 2; a solid state $^{13}$C NMR spectrum having peaks at 141.4, 130.4, 119.8 and 117.8±0.2 ppm; and any combination thereof.

The above crystalline Eltrombopag form I is an anhydrous form.

As used herein, and unless stated otherwise, the term "anhydrous" in relation to crystalline Eltrombopag relates to a crystalline Eltrombopag which contains not more than 1% (w/w) of either water or organic solvents as measured by TGA.

Crystalline Eltrombopag form I has advantageous properties selected from at least one of: chemical purity, flowability, solubility, morphology or crystal habit, stability—such as storage stability, stability to dehydration, stability to polymorphic conversion, low hygroscopicity, low content of residual solvents. Particularly, the crystalline Eltrombopag form I of the present invention has advantageous chemical purity, thermo-dynamical stability and solubility and it is non-hygroscopic in relative humidity ("RH") of 80%, 100% at room temperature, for a period of at least 10 months.

As used herein the term non-hygroscopic in relation to crystalline Eltrombopag refers to less than 0.2% (w/w) absorption of atmospheric water to the crystalline Eltrombopag in the above specified conditions, as measured by TGA.

As used herein the term "thermo-dynamical stability" in relation to crystalline Eltrombopag form I refers to less than 20%, 10%, 5%, 1%, or 0.5% conversion of crystalline Eltrombopag form I to any other solid state form of Eltrombopag under heating up to temperature of 200° C. at a heating rate of 10° C./minute, as measured by XRPD. In some embodiments, the conversion is 1%-20%, 1%-10% or 1%-5%.

Preferably, crystalline Eltrombopag form I of the present invention is substantially free of any other polymorph forms.

Figure 3:
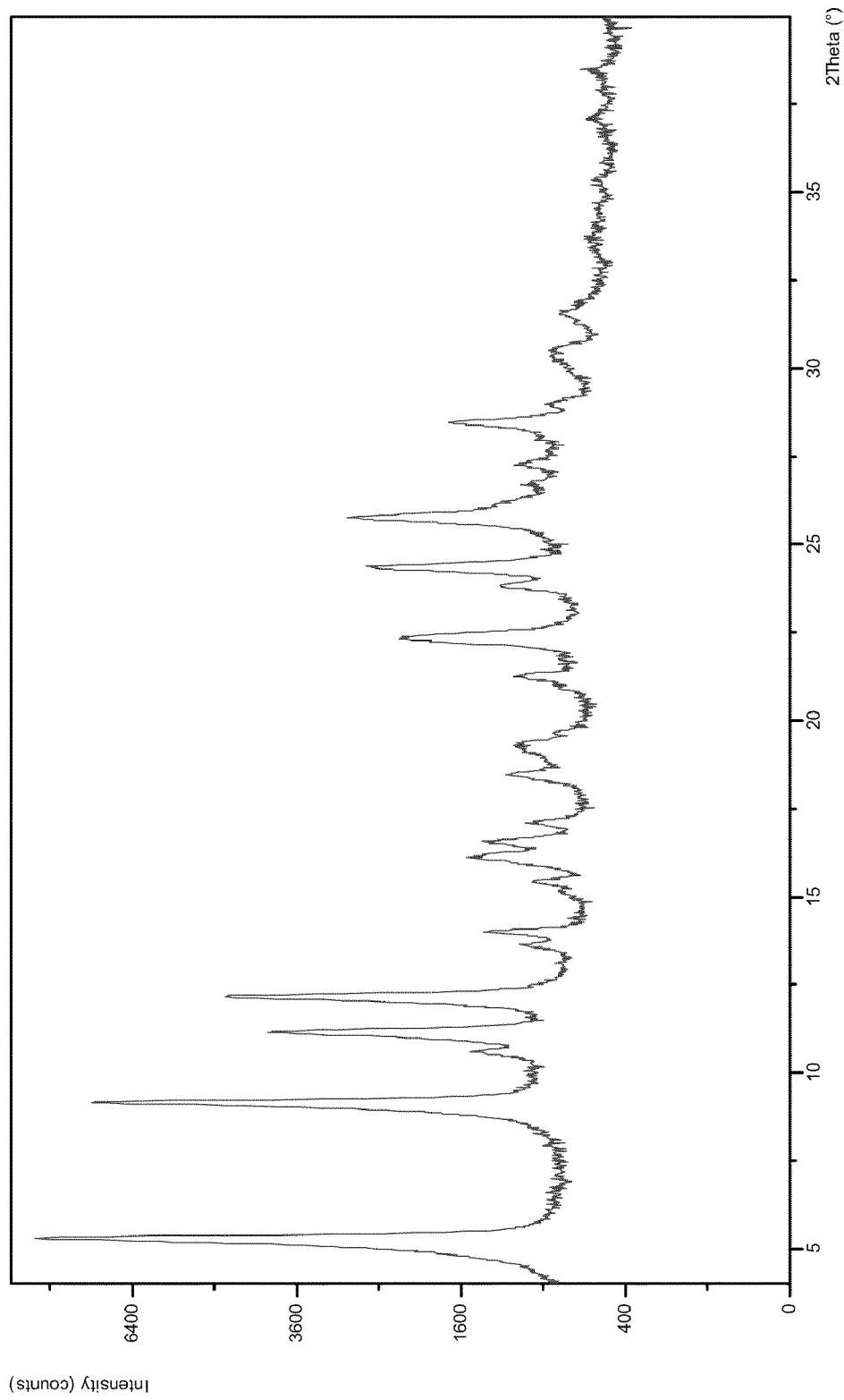
FIG. 3 shows a powder XRD pattern of crystalline Eltrombopag designated form III.
Figure 20:
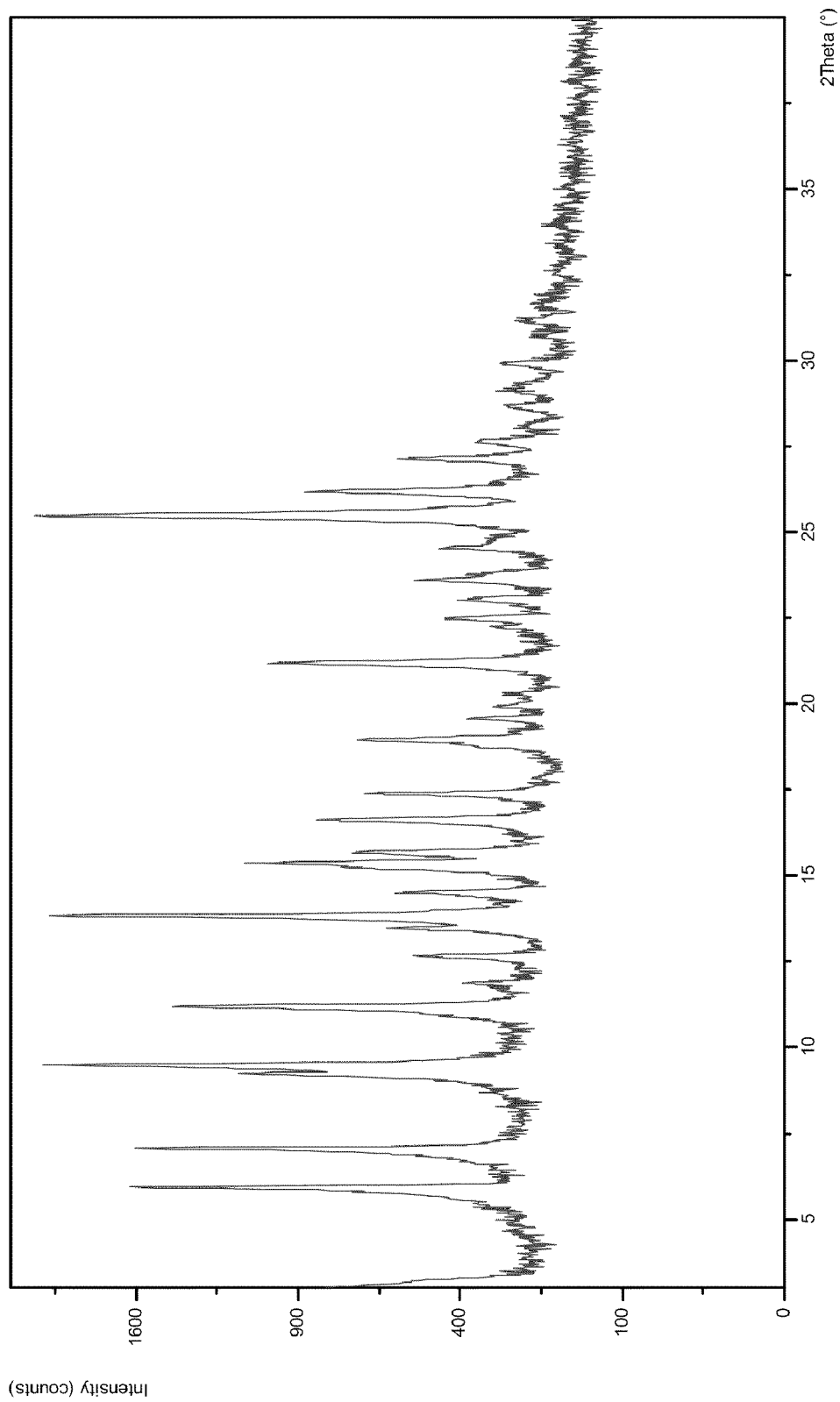
FIG. 20 shows a powder XRD pattern of crystalline Eltrombopag form XVI.
Figure 36:
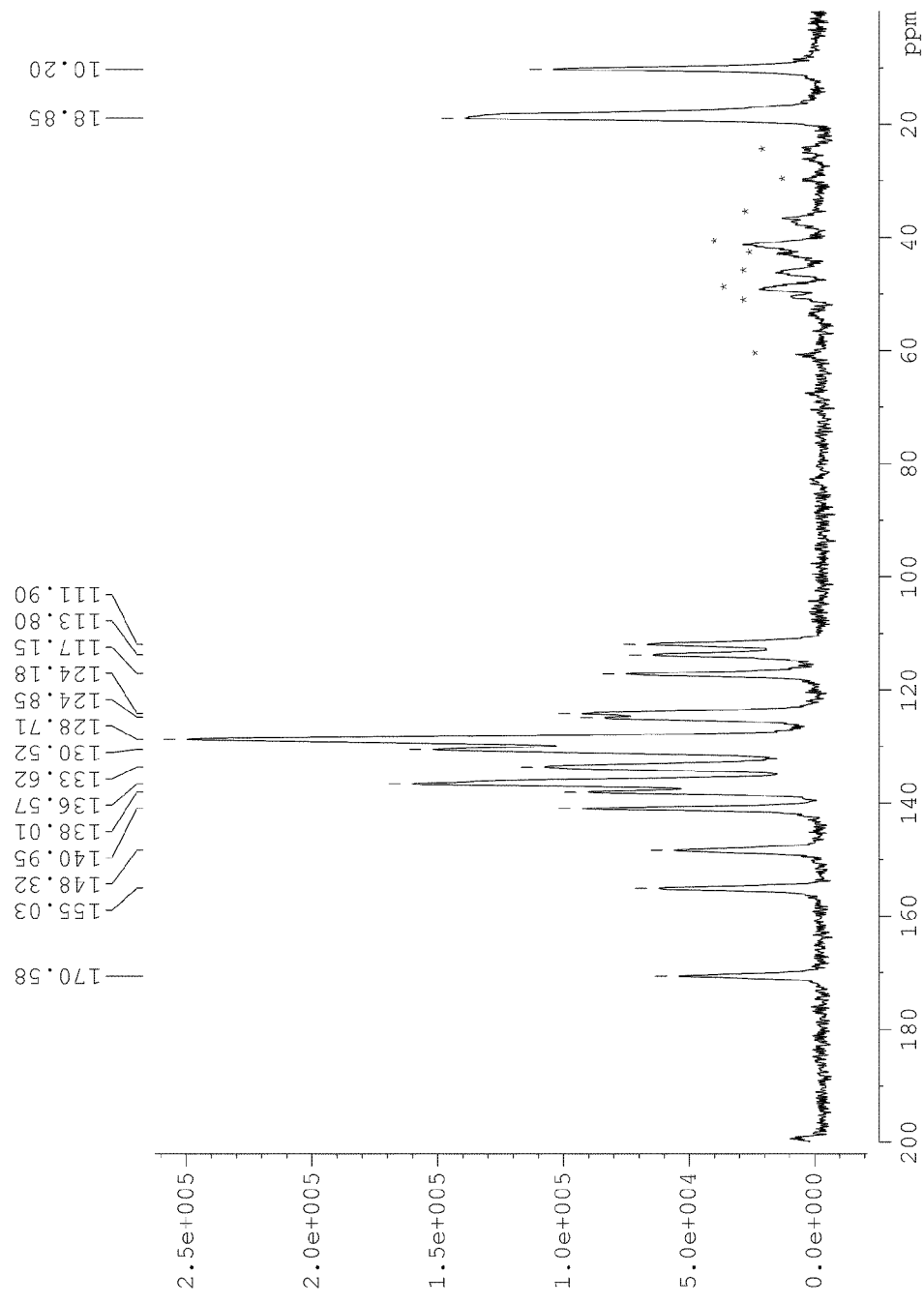
FIG. 36 shows a solid state $^{13}$C NMR spectrum of crystalline Eltrombopag designated form III.
Figure 38:
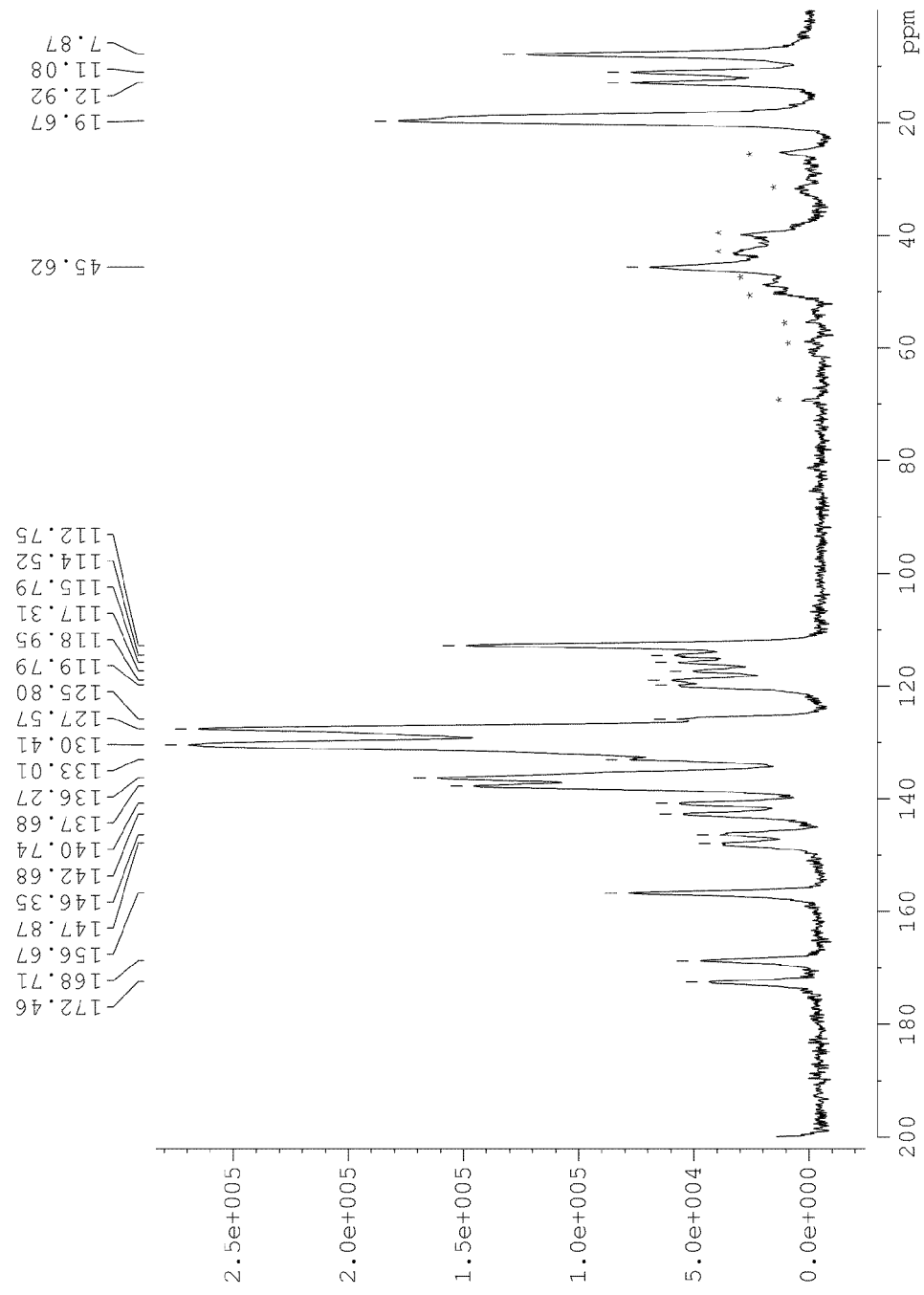
FIG. 38 shows a solid state $^{13}$C NMR spectrum of crystalline Eltrombopag designated form XVI.

The above form I can be prepared by a process comprising crystallizing Eltrombopag from glacial acetic acid or suspending crystalline Eltrombopag form III, characterized by data selected from a group consisting of: powder XRD pattern having peaks at 9.2, 11.2, 12.2 and 14.0° 2θ±0.2° 2θ; a PXRD pattern as depicted in FIG. 3; a solid state $^{13}$C NMR spectrum having peaks at 170.6, 128.7, 124.2 and 113.8±0.2 ppm; a solid state $^{13}$C NMR spectrum as depicted in FIG. 36; and any combination thereof, or crystalline Eltrombopag form XVI characterized by data selected from a group consisting of: powder XRD pattern having peaks at 7.1, 9.5, 13.9, 21.2 and 25.5° 2θ±0.2° 2θ; a PXRD pattern as depicted in FIG. 20; a solid state $^{13}$C NMR spectrum having peaks at 168.7, 156.7, 127.6 and 112.8±0.2 ppm; a solid state $^{13}$C NMR spectrum as depicted in FIG. 38; and any combination thereof, in glacial acetic acid.

Typically, the process comprises providing a solution or a suspension of Eltrombopag in glacial acetic acid and precipitating to obtain a suspension comprising the form I; wherein in case where a suspension is provided, the starting Eltrombopag is crystalline Eltrombopag form III or crystalline Eltrombopag form XVI.

Typically, when a solution is provided, glacial acetic acid is used in an amount sufficient for dissolving Eltrombopag. The solution or the suspension of Eltrombopag and glacial acetic acid can be provided by combining Eltrombopag or crystalline Eltrombopag form III and glacial acetic acid, and heating the combination. The combination can be heated to a temperature from about 96° C. to about 118°, preferably it is heated to a temperature from about 114° C. to about 118° C. After the solution or the suspension is formed, it is cooled to provide a suspension in which Eltrombopag form I precipitates. Suitable cooling temperature is from about 40° C. to about 0° C., from about room temperature to about 0° C., or from about 23° C. to about 0° C.

The above process for preparing Eltrombopag form I can further comprise recovery of the obtained Eltrombopag form I. The recovery process may comprise, for example, filtering the crystallizing form, washing and drying. Washing can be done with a mixture of methanol and water. Drying can be done under vacuum, at a temperature such as about 35° C. to about 60° C., over a period of about 2 hours to about 12 hours.

The above described process preferably provides Eltrombopag form I in chemical purity of at least about 99%, at least about 99.5%, or at least about 99.8%, area percent as measured by HPLC.

In certain embodiments, the above described process for preparing Eltrombopag form I can be used to purify Eltrombopag and thus produce chemically pure Eltrombopag salt. In preferred embodiments, the present invention provides a process of purification of Eltrombopag, comprising crystallizing Eltrombopag or suspending crystalline Eltrombopag form III or crystalline Eltrombopag form XVI in glacial acetic acid. In particular, the above chemically pure Eltrombopag form I can be purified from (Z)-methyl 3'-(2-(1-(3,4-dimethylphenyl)-3-methyl-5-oxo-1H-pyrazol-4(5H)-ylidene)hydrazinyl)-2'-hydroxybiphenyl-3-carboxylate of (referred as "EPT impurity 1") the following formula:

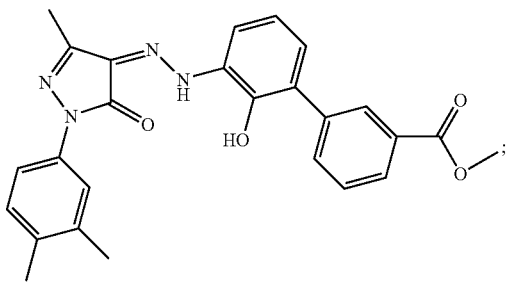

and (Z)-3'-(2-(1-(3,4-dimethylphenyl)-3-methyl-5-oxo-1H-pyrazol-4(5H)-ylidene)-hydrazinyl)-2'-hydroxybiphenyl-3-carboxamide (referred as "EPT impurity 2") of the following formula:

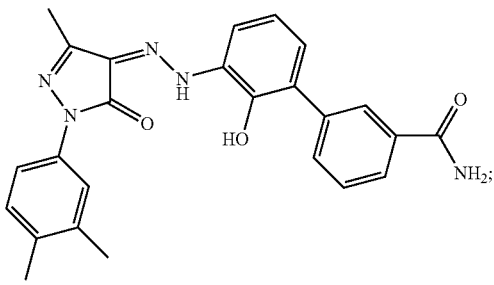

In preferred embodiments, each of the above impurities in the purified Eltrombopag can be present in an amount from about 0% to about 0.1%, from about 0.01% to about 0.1%, from about 0.01% to about 0.07%, or from about 0.01% to about 0.05%, as measured by HPLC.

Eltrombopag form I can also be prepared by a process comprising suspending a mixture of crystalline Eltrombopag form I and crystalline Eltrombopag form III in a mixture of acetone and water.

The above process comprises combining the mixture of crystalline Eltrombopag form I and form III and acetone to obtain a first suspension, which is heated prior to the addition of water. The first suspension can be heated to a temperature of about reflux temperature, preferably, about 57° C., which results in a second suspension. The second suspension is then combined with water to form a suspension. The suspension can be cooled prior to recovering crystalline form I. Suitable cooling temperature is about room temperature.

The above process for preparing Eltrombopag form I can further comprise recovery of the obtained Eltrombopag form I. The recovery process may comprise, for example, filtering the crystallized form and drying. Drying can be done under vacuum, for example at pressure of about 5 mBar. Drying can be done, for example, at a temperature of about 50° C., for a period of about 1 hour.

Figure 7:
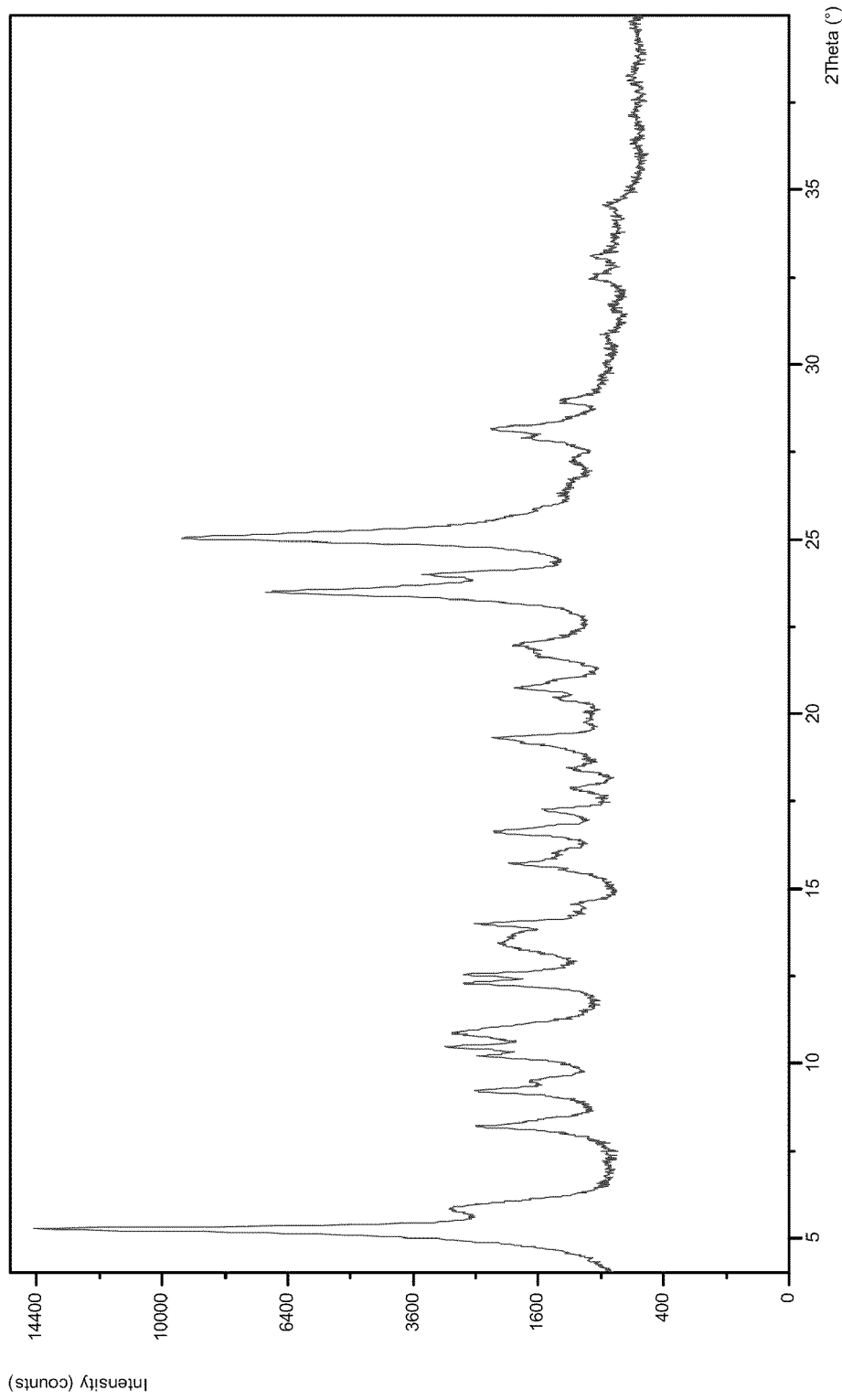
FIG. 7 shows a powder XRD pattern of crystalline Eltrombopag designated form V.

Crystalline Eltrombopag form I can be used to prepare other forms of Eltrombopag and Eltrombopag ethanolamine salt, in particular crystalline Eltrombopag designated form V characterized by data selected from a group consisting of: powder XRD pattern having peaks at 5.9, 8.2, 10.5 and 12.5° 2θ±0.2° 2θ; a PXRD pattern as depicted in FIG. 7. In certain embodiments, the present invention provides a process for preparing crystalline Eltrombopag form V, comprising preparing crystalline Eltrombopag form I by a process comprising crystallizing or suspending Eltrombopag form I in glacial acetic acid and converting it to crystalline Eltrombopag form V by a process comprising crystallizing Eltrombopag form V from a mixture of tetrahydrofuran ("THF") and water.

In another embodiment the present invention encompasses crystalline Eltrombopag characterized by a data selected from a group consisting of: powder XRD pattern having peaks at 9.2, 11.2, 12.2 and 14.0° 2θ±0.2° 2θ; a PXRD pattern as depicted in FIG. 3; a solid state $^{13}$C NMR spectrum having peaks at 170.6, 128.7, 124.2 and 113.8±0.2 ppm; a solid state $^{13}$C NMR spectrum as depicted in FIG. 36; and any combination thereof. This crystalline form of Eltrombopag is designated herein as form III.

Figure 4:
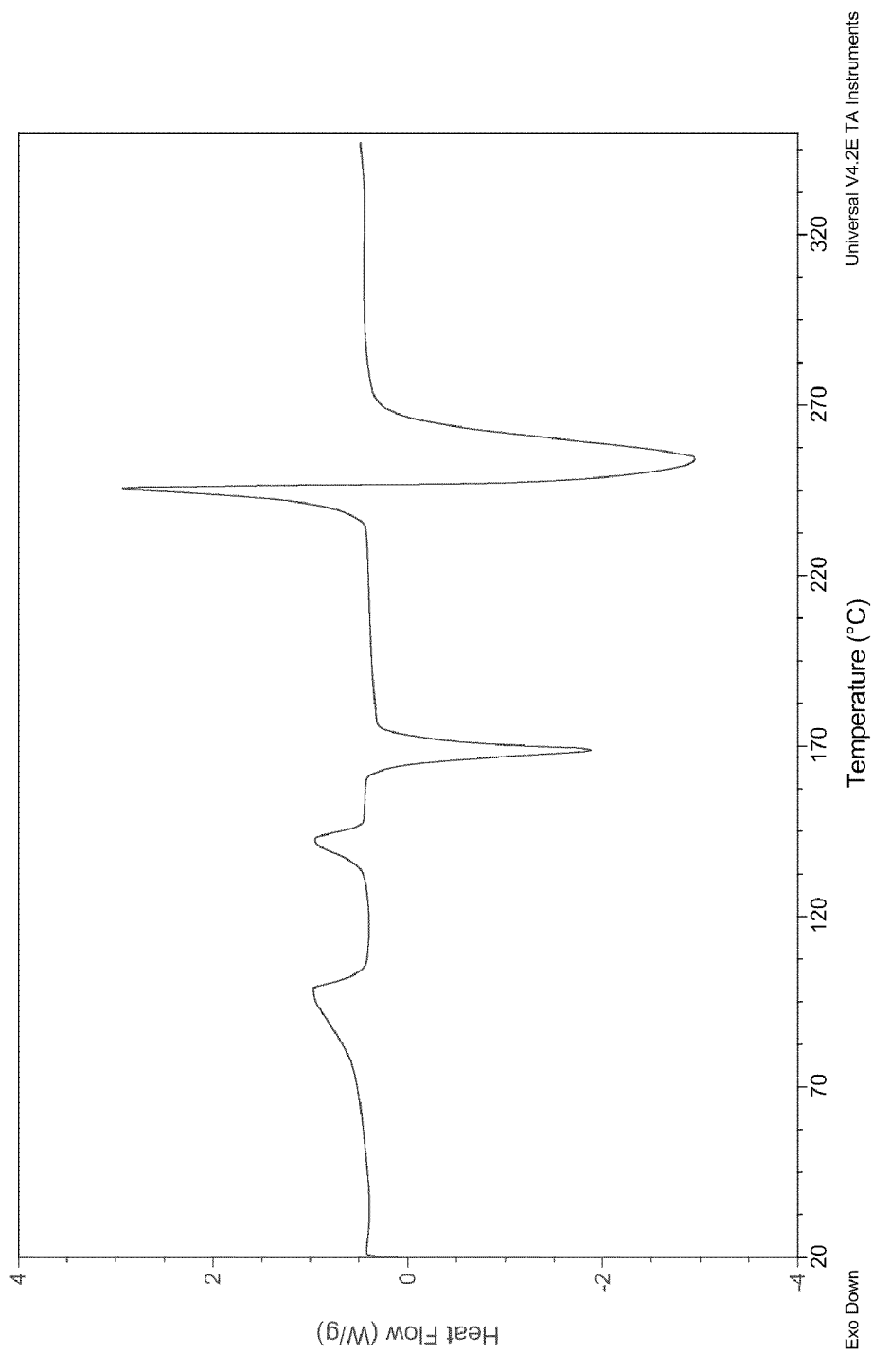
FIG. 4 shows a DSC thermogram of crystalline Eltrombopag designated form III.

The above form III of Eltrombopag can be further characterized by data selected from a group consisting of: a powder XRD pattern having peaks at 5.3, 16.1, 22.4 and 24.3° 2θ±0.2° 2θ; a DSC thermogram as depicted in FIG. 4; a solid state $^{13}$C NMR spectrum having peaks at 155.0, 141.0, 136.6 and 133.6±0.2 ppm; and any combination thereof.

The above crystalline Eltrombopag form III is a hydrate.

Crystalline Eltrombopag form III has advantageous properties selected from at least one of: chemical purity, flowability, solubility, morphology or crystal habit, stability—such as storage stability, stability to dehydration, stability to polymorphic conversion, low hygroscopicity, low content of residual solvents. Particularly, the crystalline Eltrombopag form III of the present invention have advantageous chemical purity and morphology of irregular particle shape which provide the bulk product with excellent flowability properties that are of benefit for pharmaceutical formulations, and it is non-hygroscopic in relative humidity ("RH") of 80%, 100% at room temperature, for a period of at least 10 months.

Preferably, crystalline Eltrombopag form III of the present invention is substantially free of any other polymorph forms.

The above form III can be prepared by a process comprising reacting crystalline 3'-amino-2'-hydroxybiphenyl-3-carboxylic acid ("BPCA") form I and crystalline 1-(3,4-dimethylphenyl)-3-methyl-1H-pyrazol-5-ol ("Pyrazole") from 1 in methanol to obtain Eltrombopag from III.

The above described process preferably provides Eltrombopag form III in chemical purity of at least about 98%, preferably at least about 98.5, area percent as measured by HPLC.

Figure 31:
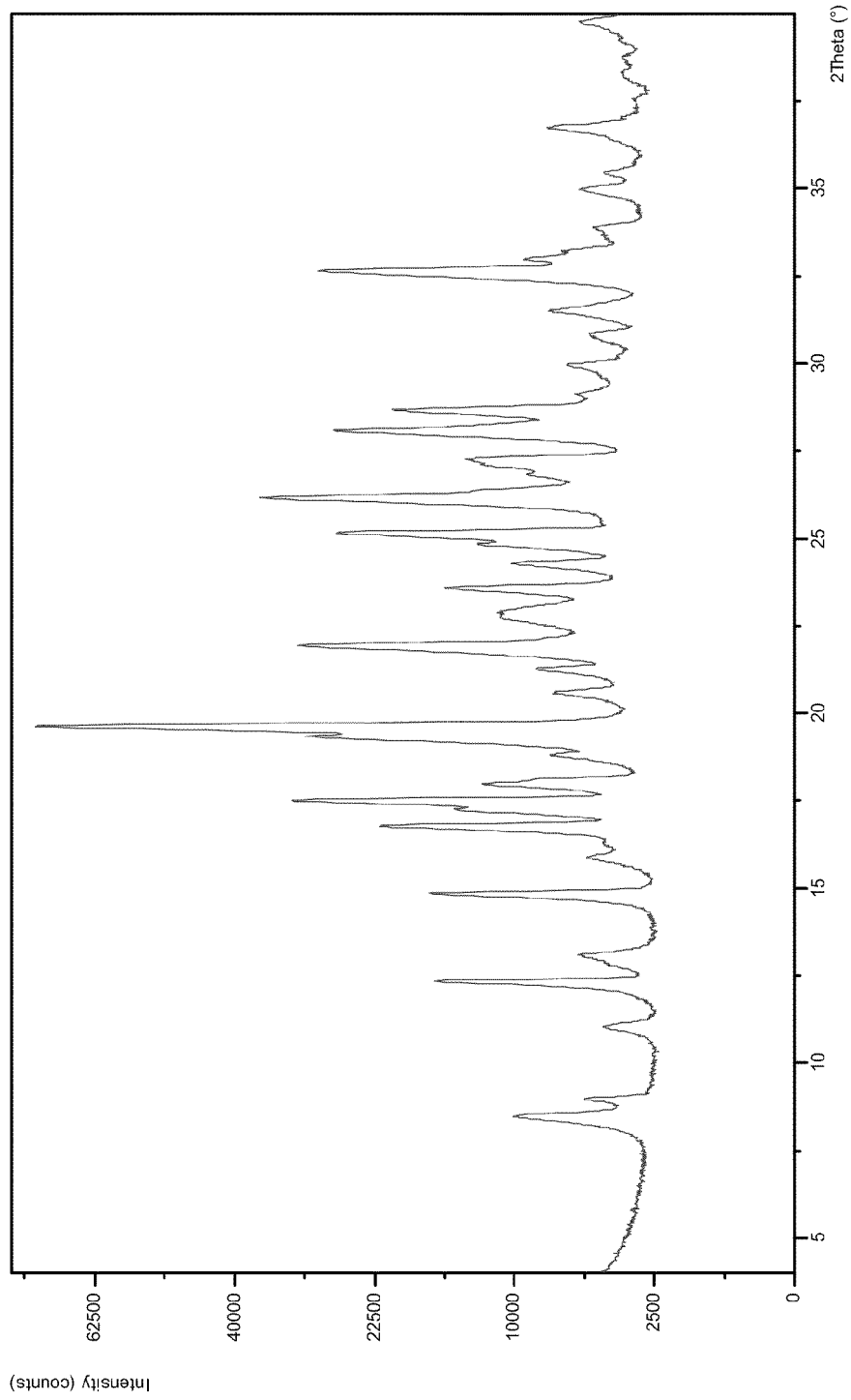
FIG. 31 shows a powder XRD pattern of crystalline 1-(3,4-dimethylphenyl)-3-methyl-1H-pyrazol-5-ol ("pyrazole") form I.

Crystalline pyrazole form I is characterized by data selected from a group consisting of: an X-ray powder diffraction having peaks at 10.72, 12.93, 17.95, 20.96, and 26.01° 2θ±0.2° 2θ; a PXRD pattern described in FIG. 31; and any combination thereof. This pyrazole crystalline Form can be further characterized by a PXRD having peaks at 9.7, 14.36, 17.09, 23.14 and 27.84° 2θ±0.2° 2θ.

Crystalline BPCA form I is characterized by data selected from a group consisting of: X-ray powder diffraction having peaks at 8.51, 14.87, 19.66, 26.19 and 32.66° 2θ±0.2° 2θ; a PXRD pattern described in FIG. 32; and any combination thereof. This BPCA crystalline Form can be further characterized by a PXRD having peaks at 12.35, 16.80, 17.53, 21.97 and 25.18° 2θ±0.2° 2θ.

The above form III can also be prepared by a process comprising dissolving Eltrombopag in ethyl acetate and cooling to precipitate crystalline Eltrombopag form III. Typically, the process comprises providing a solution of Eltrombopag in ethyl acetate and precipitating to obtain a suspension comprising the form III. The solution of Eltrombopag and ethyl acetate can be provided by combining Eltrombopag and ethyl acetate and heating the combination. The combination can be heated to a temperature from about 57° C. to about 77°, about 73° C. to about 77° C., or about 77° C. After the solution is formed, it can be cooled to provide a suspension in which Eltrombopag form III precipitates. Cooling is to a temperature such as about 0° C. to about −5° C., or about 0° C.

The above process for preparing Eltrombopag form III can further comprise recovery of the obtained Eltrombopag form III. The recovery process may comprise, for example, filtering the crystalline form and drying. Drying can be done at a temperature such as about room temperature, for example about 22° C., for a period of about overnight.

Crystalline Eltrombopag form III can be used to prepare other forms of Eltrombopag and Eltrombopag ethanolamine salt, in particular crystalline Eltrombopag form I. In certain embodiments, the present invention provides a process for preparing crystalline Eltrombopag form I, comprising preparing crystalline Eltrombopag form III by reacting crystalline BPCA form I and crystalline pyrazole form Ito obtain crystalline Eltrombopag from III and converting the obtained crystalline Eltrombopag from III to crystalline Eltrombopag form I by a process comprising crystallizing or suspending Eltrombopag form III in glacial acetic acid. The process can further comprise re-crystallizing Eltrombopag form III obtained from the reaction in ethyl acetate prior to converting it to crystalline Eltrombopag form I.

Figure 5:
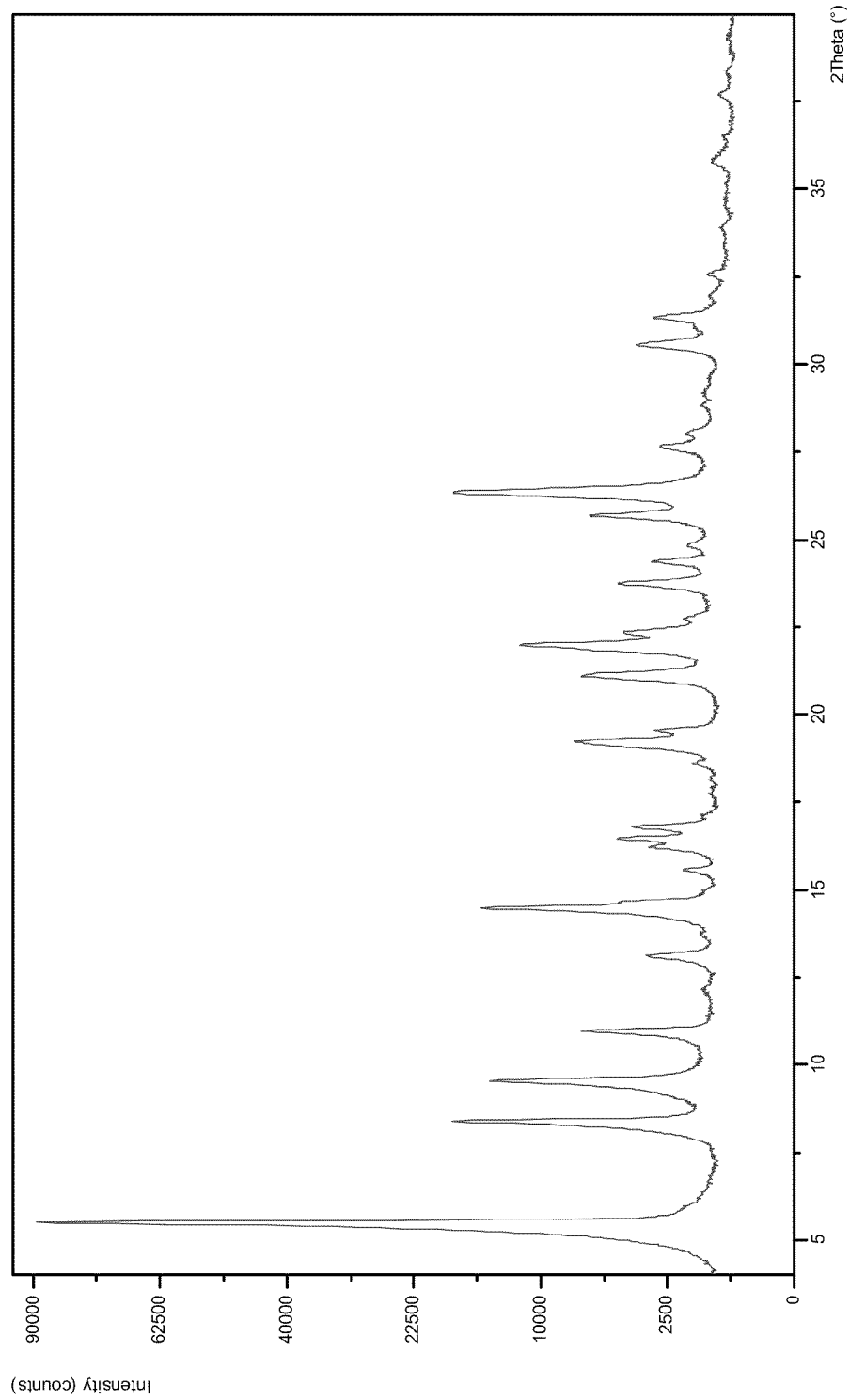
FIG. 5 shows a powder XRD pattern of crystalline Eltrombopag designated form IV.

In yet another embodiment the present invention encompasses crystalline Eltrombopag characterized by data selected from a group consisting of: a powder XRD pattern having peaks at 5.5, 9.6, 14.5, 16.5 and 19.3° 2θ±0.2° 2θ; a PXRD pattern as depicted in FIG. 5; and any combination thereof. This crystalline form of Eltrombopag is designated herein as form IV.

Figure 6:
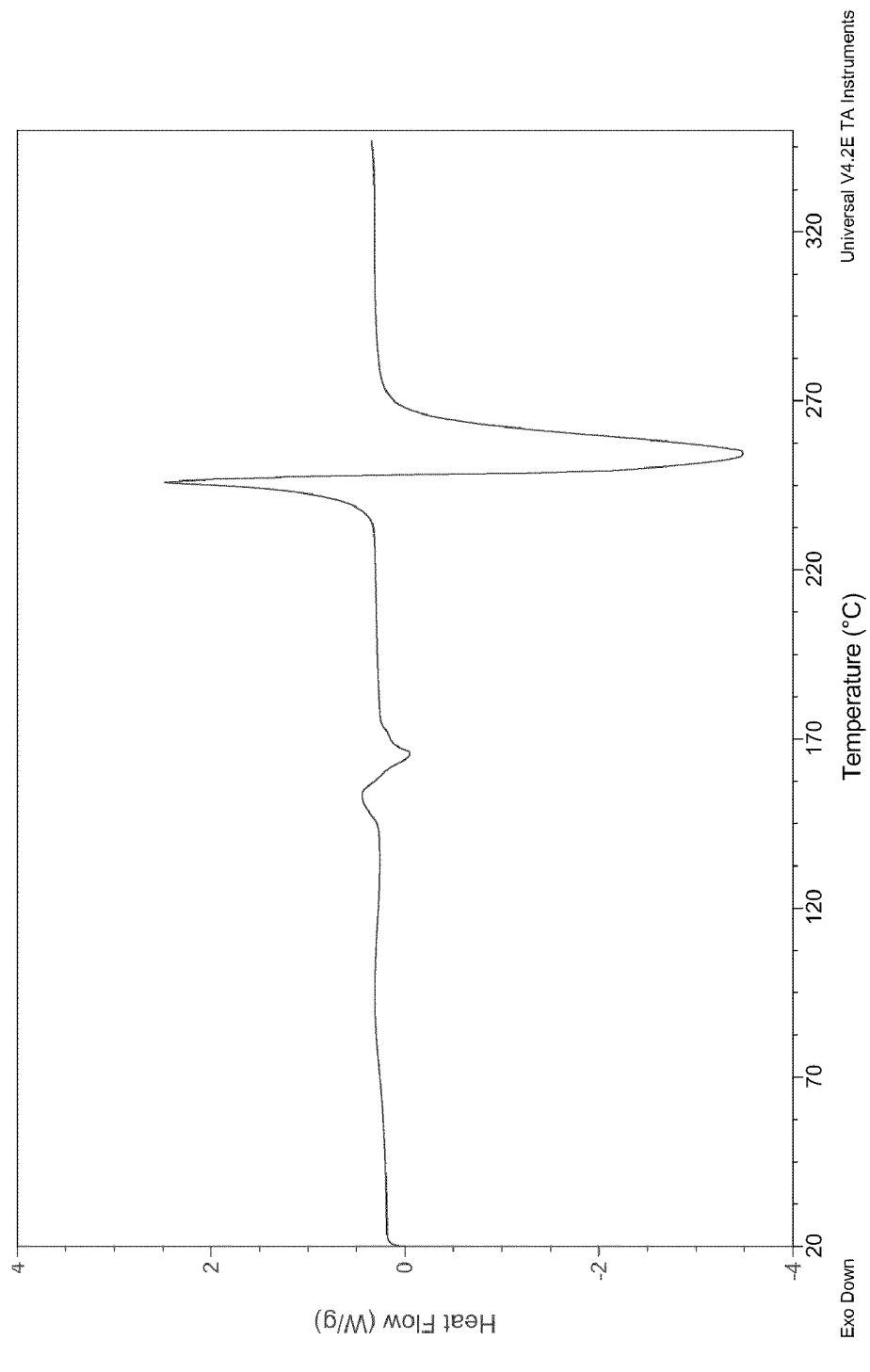
FIG. 6 shows a DSC thermogram of crystalline Eltrombopag designated form IV.

The above form IV of Eltrombopag can be further characterized by data selected from a group consisting of: a powder XRD pattern having peaks at 8.4, 11.0, 13.1, 21.1 and 22.0° 2θ±0.2° 2θ; a DSC thermogram as depicted in FIG. 6; and any combination thereof.

The above form IV can be prepared by a process comprising suspending crystalline Eltrombopag form I in a mixture of methanol and water. The process can comprise combining the crystalline Eltrombopag form I and a mixture of methanol and water, to obtain a first suspension. A suitable ratio of methanol and water in the mixture can be, for example, about 1:3 V/V. The first suspension is then heated, providing the suspension, prior to recovering the form IV. Example for heating temperature can be about 80° C.

The above process for preparing Eltrombopag form IV can further comprise recovery of the obtained Eltrombopag form IV. The recovery process may comprise, for example, cooling the heated suspension, for example, to a temperature of about room temperature, e.g. about 22° C., filtering the crystalling form, washing, e.g., with methanol, and drying. Drying can be air drying, for a period such as about overnight.

Figure 37:
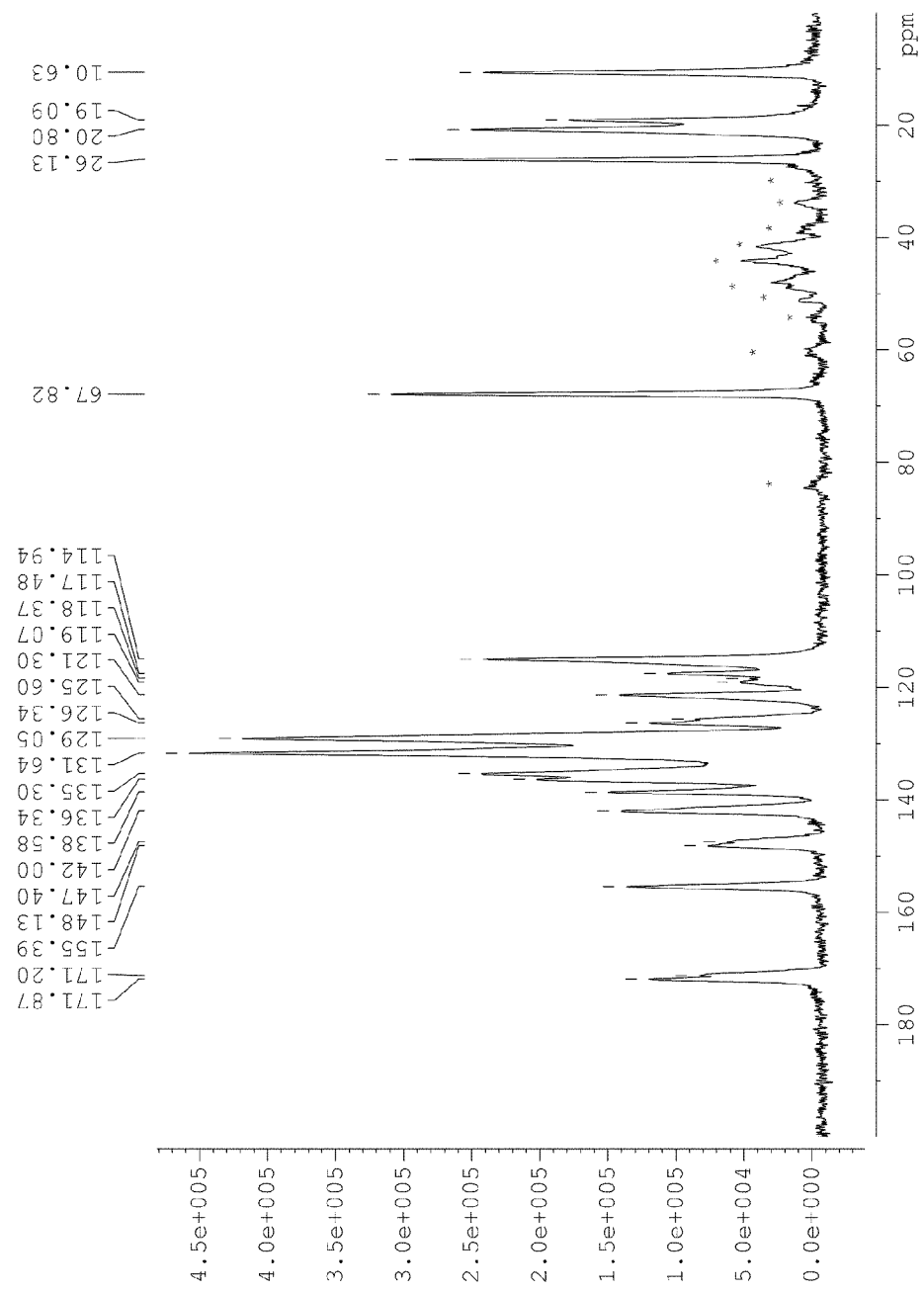
FIG. 37 shows a solid state $^{13}$C NMR spectrum of crystalline Eltrombopag designated form V.

In one embodiment the present invention encompasses crystalline Eltrombopag characterized by data selected from a group consisting of: a powder XRD pattern having peaks at 5.9, 8.2, 10.5 and 12.5° 2θ±0.2° 2θ; a PXRD pattern as depicted in FIG. 7; a solid state $^{13}$C NMR spectrum having peaks at 142.0, 131.6, 114.9 and 67.8±0.2 ppm; a solid state $^{13}$C NMR spectrum as depicted in FIG. 37; and any combination thereof. This crystalline form of Eltrombopag is designated herein as form V.

Figure 8:
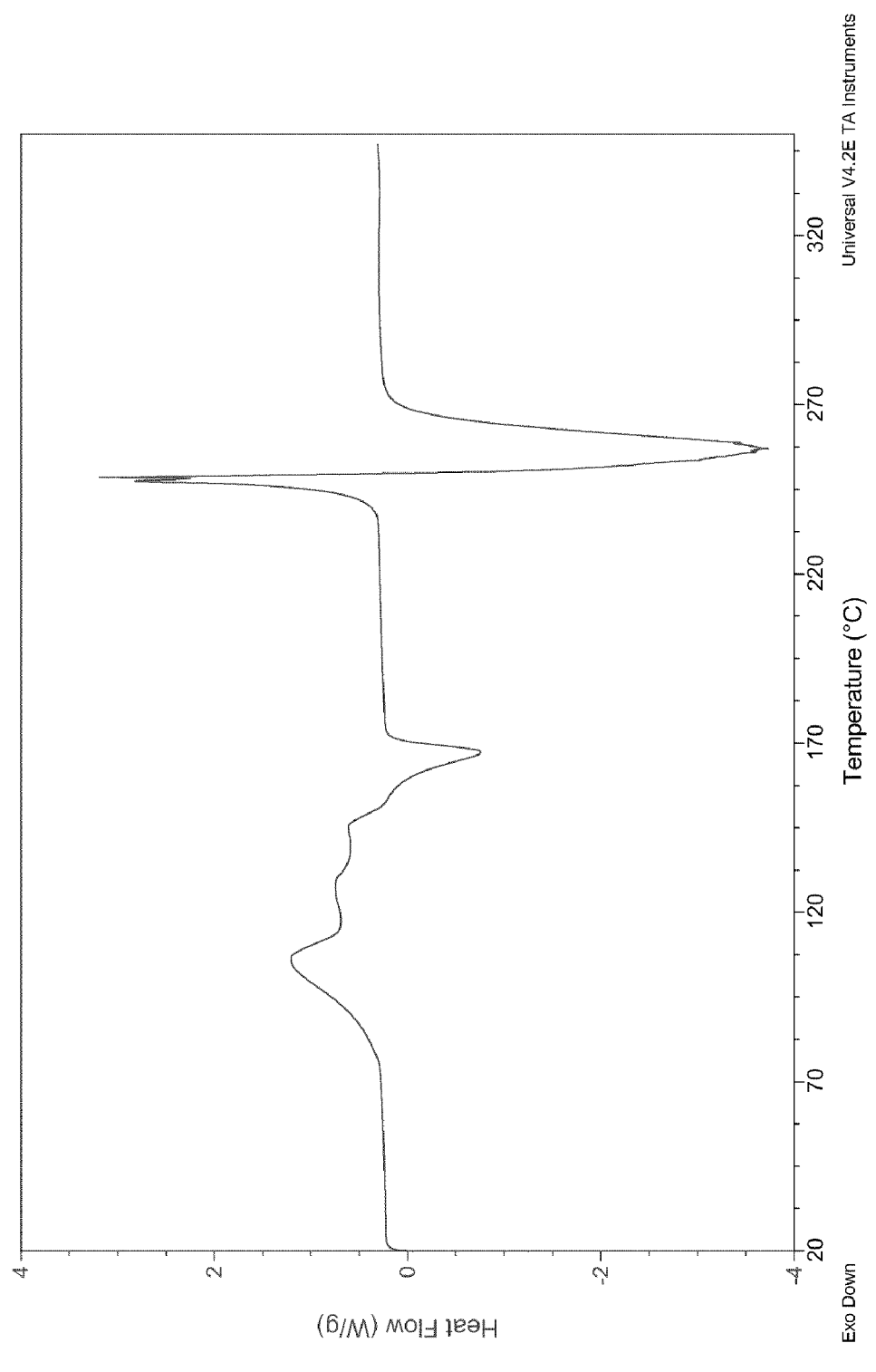
FIG. 8 shows a DSC thermogram of crystalline Eltrombopag designated form V.

The above form V of Eltrombopag can be further characterized by data selected from a group consisting of: a powder XRD pattern having peaks at 5.3, 9.2, 14.0, 23.5 and 25.0° 2θ±0.2° 2θ; a DSC thermogram as depicted in FIG. 8; a solid state $^{13}$C NMR spectrum having peaks at 171.9, 155.4, 136.3 and 121.3±0.2 ppm; and any combination thereof.

The above crystalline Eltrombopag form V is a tetrahydrofuran/water solvate.

Crystalline Eltrombopag form V has advantageous properties selected from at least one of: chemical purity, flowability, solubility, morphology or crystal habit, stability—such as storage stability, stability to dehydration, stability to polymorphic conversion, and low hygroscopicity. Particularly, the crystalline Eltrombopag form V of the present invention has advantageous chemical purity and it is non-hygroscopic in relative humidity ("RH") of 80%, 100% at room temperature, for a period of at least 10 months.

Preferably, crystalline Eltrombopag form V of the present invention is substantially free of any other polymorph forms.

The above form V can be prepared by a process comprising crystallizing the Eltrombopag from a mixture of tetrahydrofuran ("THF") and water. Typically, the crystallization comprises providing a solution of Eltrombopag in THF and adding water to obtain a suspension comprising the form V. The solution of Eltrombopag and THF can be provided by combining Eltrombopag and THF. To aid in dissolution, the combination can be heated, for example to a temperature of about 60° C. to about reflux temperature. After the solution is formed, water or a mixture of water and methanol, e.g. in a ratio of about 1:1 V/V, is added, for example in a dropwise manner, to the solution, providing a suspension comprising the crystalline Eltrombopag form V. The precipitated Eltrombopag form V can then be recovered. The recovery process may comprise, for example, filtering the crystalline form, washing and drying. Washing can be done with either water or a mixture of THF and water. Drying can be done under vacuum, for instance, at pressure of about 5 mBar, at a temperature of about 50° C., for a period such as about 1 hour.

The above process of Eltrombopag can further comprise purification of Eltrombopag prior to the crystallization. Said purification comprises suspending or crystallizing Eltrombopag from glacial acetic acid. Typically, the purification step provide crystalline Eltrombopag from I.

Figure 9:
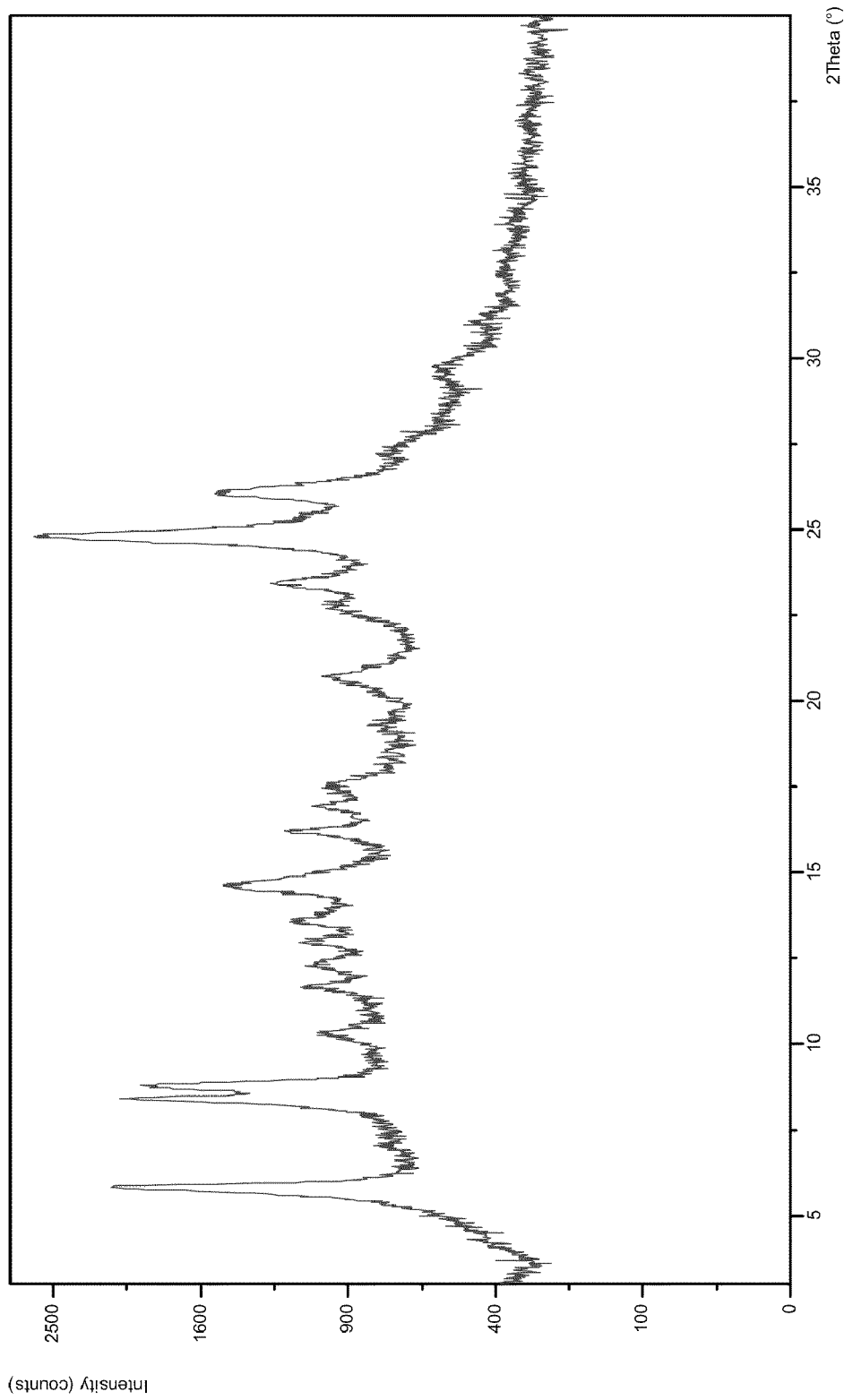
FIG. 9 shows a powder XRD pattern of crystalline Eltrombopag designated form VI.

In one embodiment the present invention encompasses crystalline Eltrombopag characterized by data selected from a group consisting of: powder XRD pattern having peaks at 5.9, 8.8, 10.3 and 11.7° 2θ±0.2° 2θ; a PXRD pattern as depicted in FIG. 9; and any combination thereof. This crystalline form of Eltrombopag can be designated form VI.

The above form VI of Eltrombopag can be further characterized by a powder XRD pattern having peaks at 8.4, 14.7, 16.2, 23.5 and 24.8° 2θ±0.2° 2θ.

The above form VI can be prepared by a process comprising heating crystalline Eltrombopag form V to a temperature from about 115° C. to about 125°, from about 118° to about 122° C., or from about 120° C. Heating can be done at a rate of 10° C. per minute. The above process can be done under nitrogen. After heating, the sample is cooled, for example to a temperature of about 20°, at a cooling rate of, for example, about 10° C./min.

Figure 10:
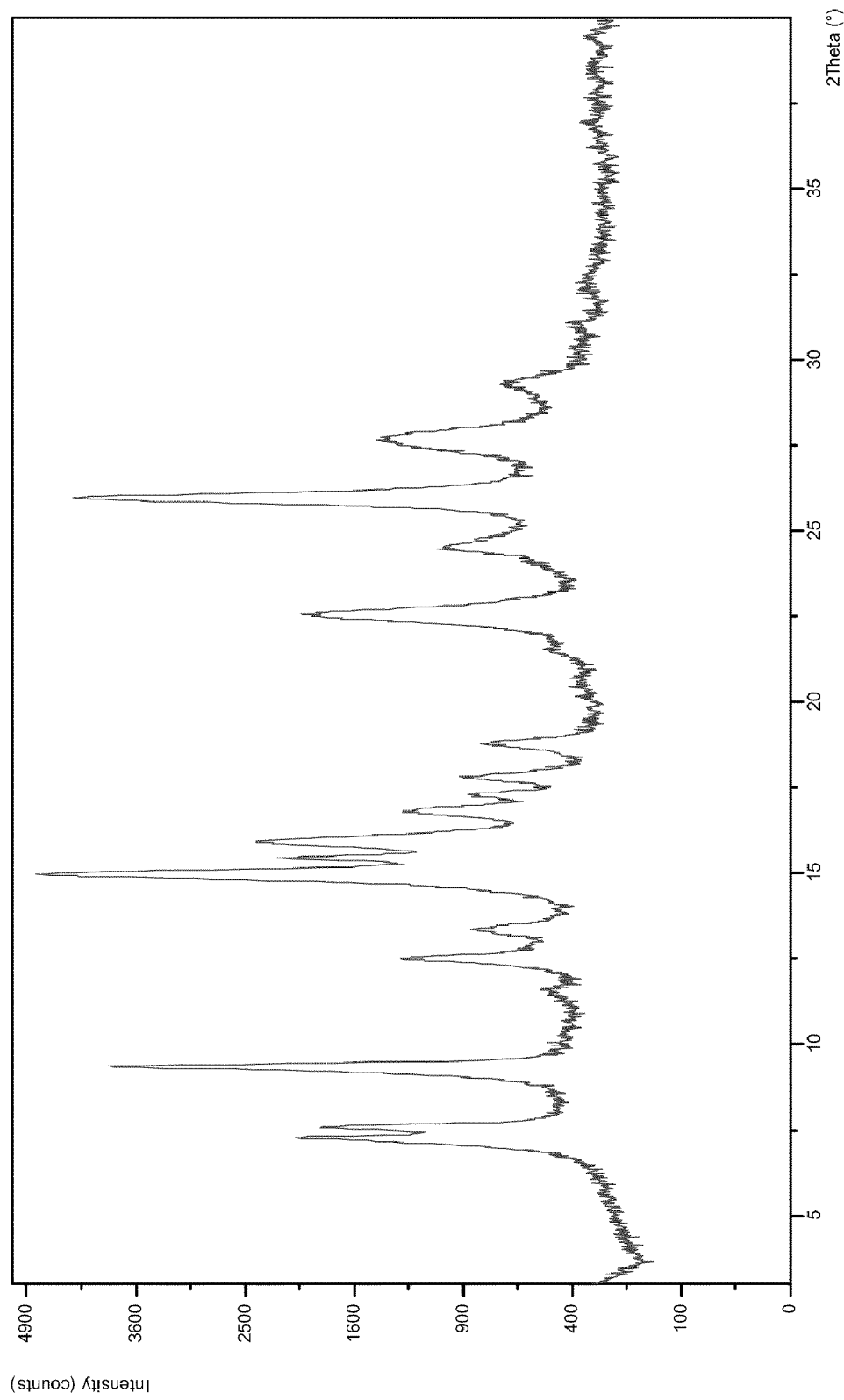
FIG. 10 shows a powder XRD pattern of crystalline Eltrombopag designated form VII.

In one embodiment the present invention encompasses crystalline Eltrombopag characterized by data selected from a group consisting of: powder XRD pattern having peaks at 7.6, 9.4, 15.0 and 16.0° 2θ±0.2° 2θ; a PXRD pattern as depicted in FIG. 10; and any combination thereof. This crystalline form of Eltrombopag is designated herein as form VII.

The above form VII of Eltrombopag can be further characterized by a powder XRD pattern having peaks at about 7.3, 12.5, 18.8, 22.5 and 26.0° 2θ±0.2° 2θ.

The above form VII can be prepared by a process comprising heating crystalline Eltrombopag form V to a temperature from about 200° C. to about 220° C., from about 211° C. to about 215° C., or from 213° C. Heating can be done at a rate of 10° C. per minute. The above process can be done under nitrogen. After heating, the sample is cooled, for example to a temperature of about 20°, at a cooling rate of about 10° C./min.

Figure 11:
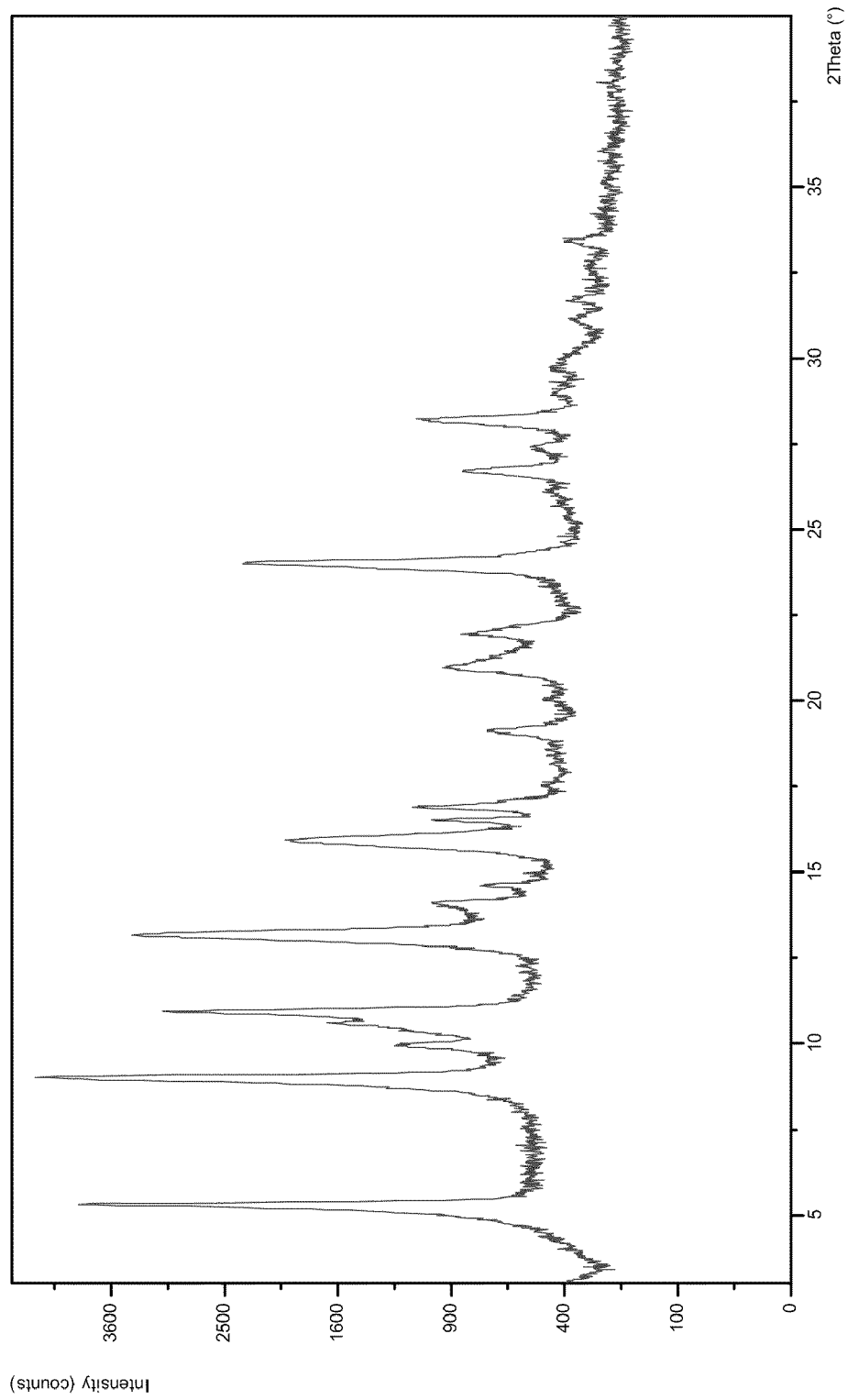
FIG. 11 shows a powder XRD pattern of crystalline Eltrombopag designated form VIII.

In one embodiment the present invention encompasses crystalline Eltrombopag characterized by data selected from a group consisting of: powder XRD pattern having peaks at 9.0, 13.2, 16.0 and 24.0° 2θ±0.2° 2θ; a PXRD pattern as depicted in FIG. 11; and any combination thereof. This crystalline form of Eltrombopag is designated herein as form VIII.

Figure 12:
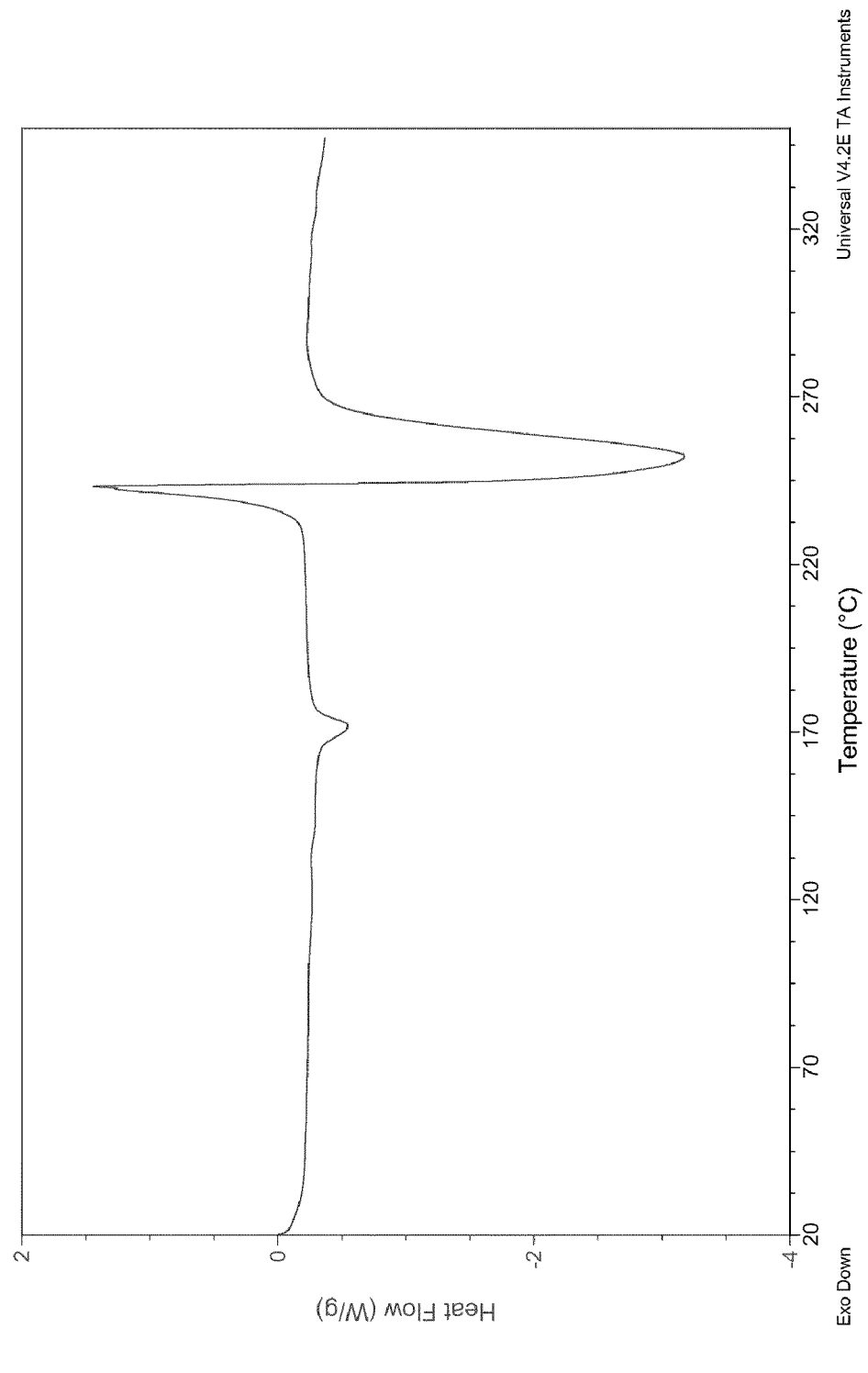
FIG. 12 shows a DSC thermogram of crystalline Eltrombopag designated form VIII.

The above form VIII of Eltrombopag can be further characterized by data selected from a group consisting of: a powder XRD pattern having peaks at 5.3, 11.0, 17.0, 19.1 and 28.2° 2θ±0.2° 2θ; a DSC thermogram as depicted in FIG. 12; and any combination thereof.

The above form VIII can be prepared by a process comprising suspending crystalline Eltrombopag form IV in a mixture of dichloromethane and water. The process comprises combining crystalline Eltrombopag form IV and a mixture of dichloromethane and water and adding water to obtain Eltrombopag form I. The process may further comprise basifying and then acidifying the suspension, prior to recovering the crystalline form. Basifying can be done by adding a base to the suspension. Examples for base can be an inorganic base like an alkali metal base, such as sodium hydroxide. Acidifying is done by adding an acid to the basified suspension. Suitable acid can be an inorganic acid, for example, hydrochloric acid.

The Eltrombopag form VIII can then be recovered. The recovery process may comprise separating the phases, filtering Eltrombopag form VIII from the organic phase and drying, e.g under vacuum. Drying can be done at a pressure of about 5 mBar, for example at a temperature of about 50° C., over a period of about ½ hour.

Figure 13:
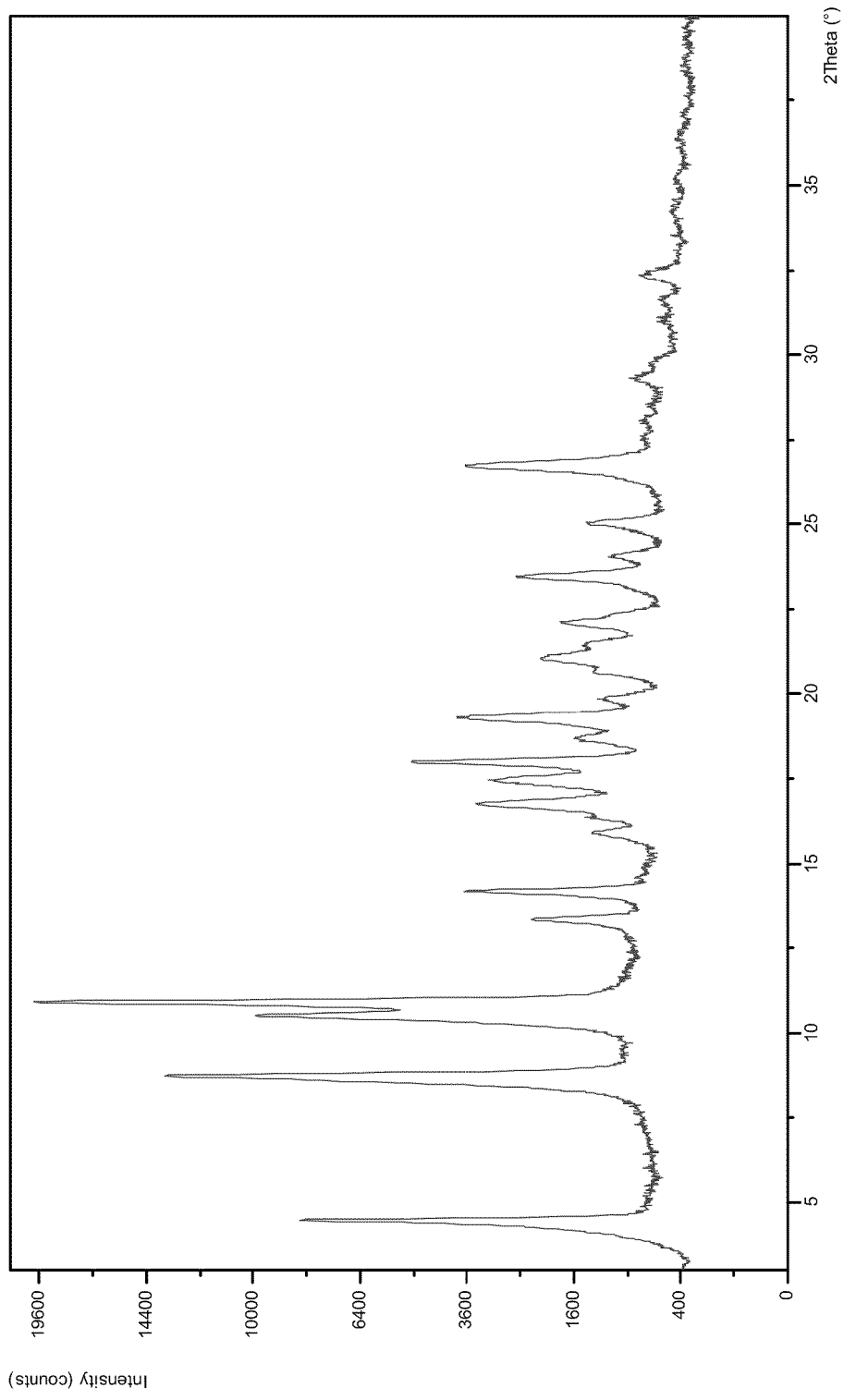
FIG. 13 shows a powder XRD pattern of crystalline Eltrombopag form IX.

In yet another embodiment the present invention encompasses crystalline Eltrombopag characterized by a data selected from a group consisting of: powder XRD pattern having peaks at 4.5, 14.2, 17.4 and 18.0° 2θ±0.2° 2θ; a PXRD pattern as depicted in FIG. 13; and any combination thereof. This crystalline form of Eltrombopag is designated herein as form IX.

The above form IX of Eltrombopag can be further characterized by a powder XRD pattern having peaks at 8.8, 10.9, 13.4 and 26.7° 2θ±0.2° 2θ.

The above form IX can be prepared by a process comprising crystallizing Eltrombopag from THF. The crystallization comprises providing a solution of Eltrombopag in THF and precipitating the crystalline form. The solution can be provided by combining Eltrombopag and THF; and heating the combination, for instance to a temperature at which a solution is formed. Precipitation can be achieved by cooling the solution to obtain a suspension comprising the crystalline form. The cooling temperature can be about room temperature, or about 22° C. The obtained crystalline form can then be recovered from the suspension. The recovery can comprise filtering the crystalline form and maintaining the recovered solid, for example at a temperature of about room temperature.

Figure 14:
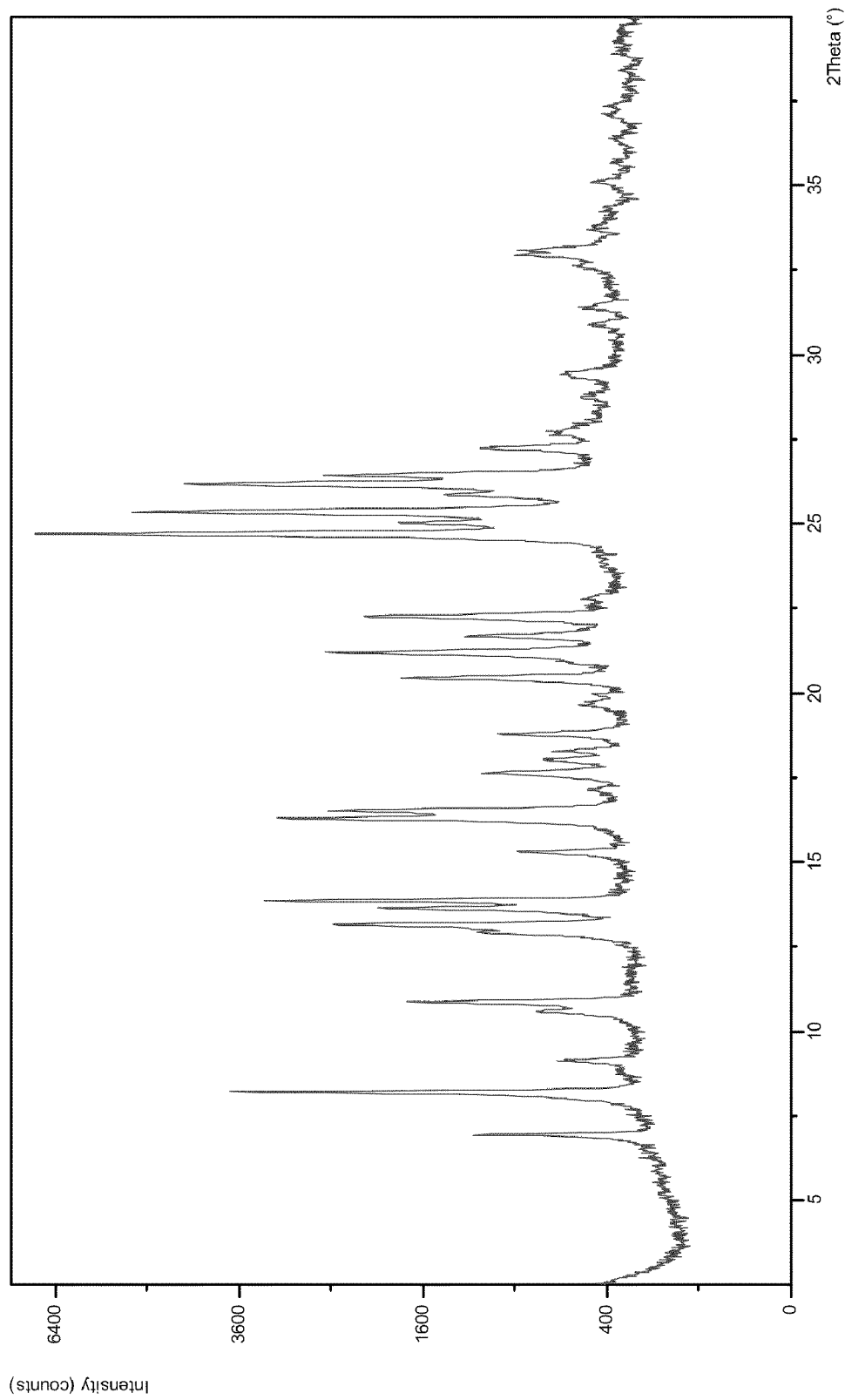
FIG. 14 shows a powder XRD pattern of crystalline Eltrombopag form X.

In one embodiment the present invention encompasses crystalline Eltrombopag characterized by a data selected from a group consisting of: powder XRD pattern having peaks at 6.9, 13.8, 20.4 and 24.7° 2θ±0.2° 2θ; a PXRD pattern as depicted in FIG. 14; and any combination thereof. This crystalline form of Eltrombopag is designated herein as form X. The above form X of Eltrombopag can be further characterized by a powder XRD pattern having peaks at 8.2, 13.2, 16.3 and 25.3° 2θ±0.2° 2θ.

The above form X can be prepared by a process comprising crystallizing Eltrombopag from DMSO. The crystallization comprises providing a solution of Eltrombopag in DMSO and precipitating the crystalline form. The solution can be provided by combining Eltrombopag and DMSO; and heating the combination, for example, to a temperature at which a solution is formed. Precipitation can be achieved, for example, by cooling the solution to obtain a suspension comprising the crystalline form. A suitable cooling temperature is a temperature, for example, of about room temperature, or about 22° C. The obtained crystalline form can then be recovered from the suspension. The recovery can comprise filtering the crystalline form and maintaining the recovered solid, for example at a temperature of about room temperature.

Figure 15:
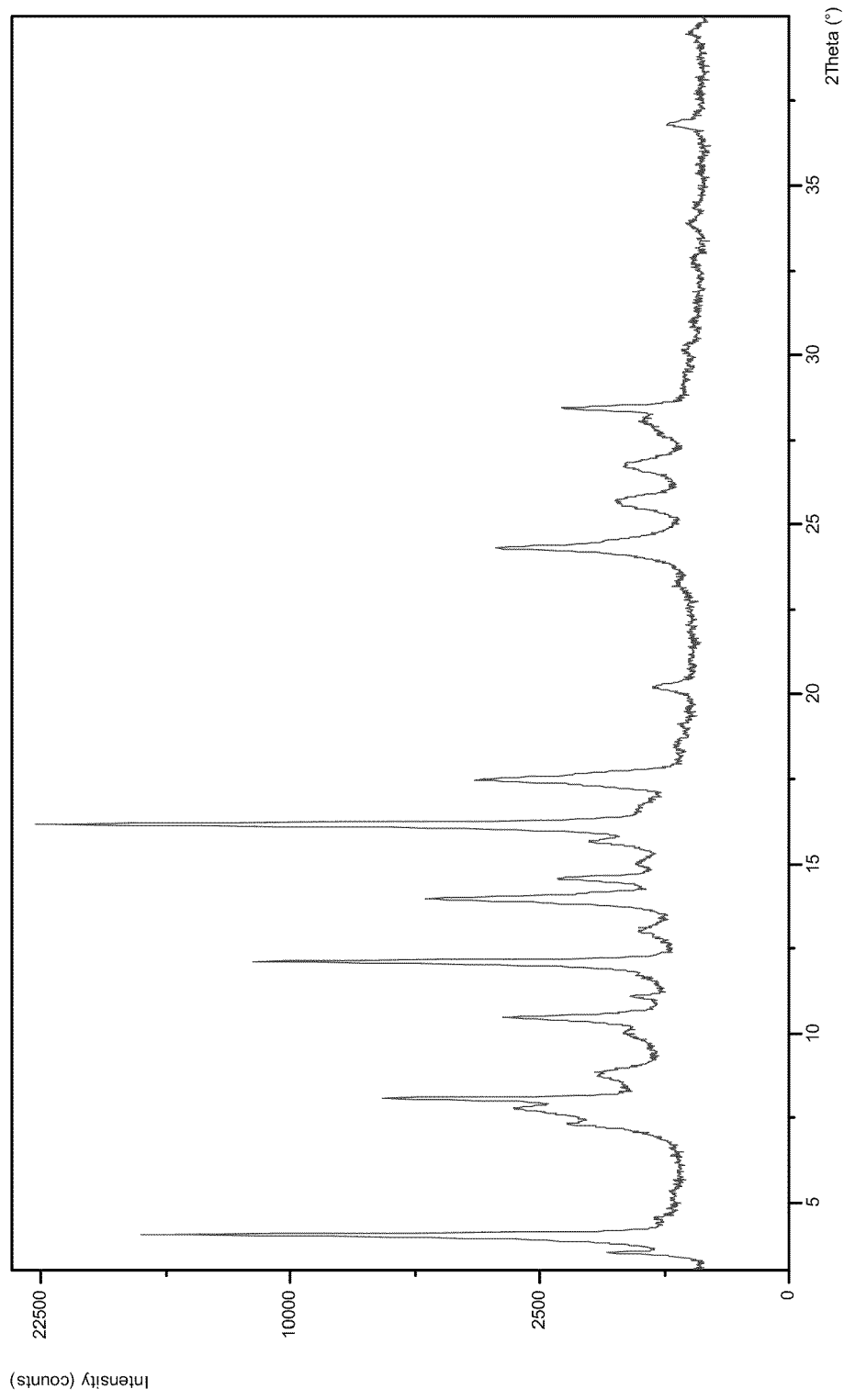
FIG. 15 shows a powder XRD pattern of crystalline Eltrombopag form XI.

In another embodiment the present invention encompasses crystalline Eltrombopag characterized by a data selected from a group consisting of: a powder XRD pattern having peaks at 3.5, 10.5, 14.0 and 28.4° 2θ±0.2° 2θ; a PXRD pattern as depicted in FIG. 15; and any combination thereof. This crystalline form of Eltrombopag is designated herein as form XI. The above form XII of Eltrombopag can be further characterized by a powder XRD pattern having peaks at 4.1, 8.1, 12.1 and 16.2° 2θ±0.2° 2θ.

The above form XI can be prepared by a process comprising crystallizing Eltrombopag from acetone. The crystallization comprises providing a solution of Eltrombopag in acetone and precipitating the crystalline form. The solution can be provided by combining Eltrombopag and acetone; and heating the combination, for instance, to a temperature at which a solution is formed. Precipitation can be achieved, for example, by cooling the solution to obtain a suspension comprising the crystalline form. A suitable cooling temperature, for example, is a temperature of about room temperature, or about 22° C. The obtained crystalline form can then be recovered from the suspension. The recovery can comprise filtering the crystalline form and maintaining the recovered solid. Maintaining can be done at about room temperature.

Figure 16:
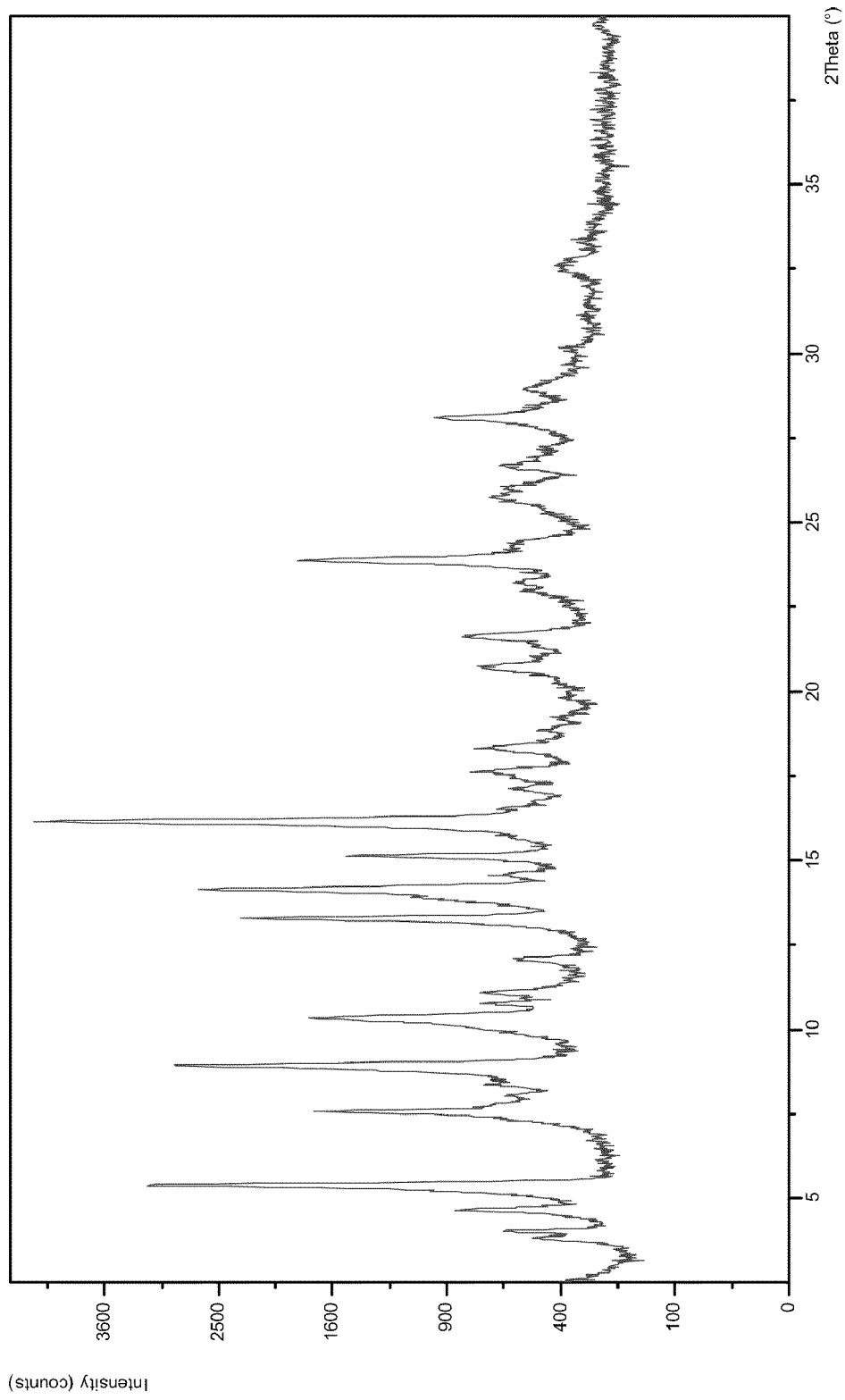
FIG. 16 shows a powder XRD pattern of crystalline Eltrombopag form XII.

In yet another embodiment the present invention encompasses crystalline Eltrombopag characterized by a data selected from a group consisting of: powder XRD pattern having peaks at 4.6, 7.6, 8.9 and 16.2° 2θ±0.2° 2θ; a PXRD pattern as depicted in FIG. 16; and any combination thereof. This crystalline form of Eltrombopag is designated herein as form XII. The above form XII of Eltrombopag can be further characterized by a powder XRD pattern having peaks at 10.4, 13.3, 14.1, 15.1 and 23.9° 2θ±0.2° 2θ.

The above form XII can be prepared by a process comprising crystallizing Eltrombopag from methoxybenzene. The crystallization comprises providing a solution of Eltrombopag in methoxybenzene and precipitating the crystalline form. The solution can be provided by combining Eltrombopag and methoxybenzene; and heating the combination, for instance, to a temperature at which a solution is formed. Precipitation can be achieved, for example, by cooling the solution to obtain a suspension comprising the crystalline form. A suitable cooling temperature, for example, is a temperature of about room temperature, about 22° C. The obtained crystalline form can then be recovered from the suspension. The recovery can comprise filtering the crystalline form and maintaining the recovered solid, for instance at a temperature of about room temperature.

Figure 17:
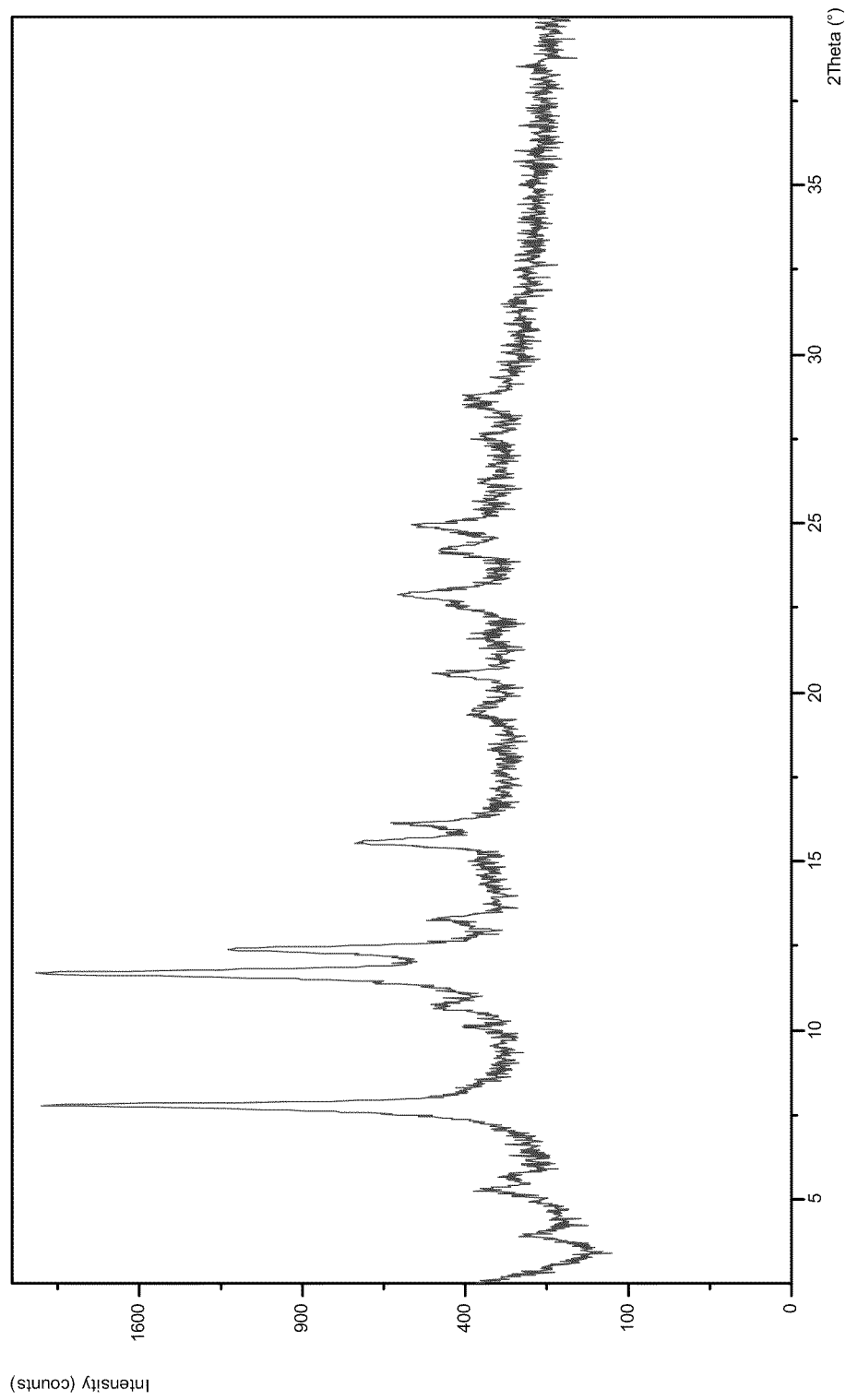
FIG. 17 shows a powder XRD pattern of crystalline Eltrombopag form XIII.

In one embodiment the present invention encompasses crystalline Eltrombopag characterized by a data selected from a group consisting of: powder XRD pattern having peaks at 3.9, 7.8, 11.7 and 12.4° 2θ±0.2° 2θ; a PXRD pattern as depicted in FIG. 17; and any combination thereof. This crystalline form of Eltrombopag is designated herein as form XIII. The above form XIII of Eltrombopag can be further characterized by a powder XRD pattern having peaks at 15.5, 20.5, 23.0 and 25.0° 2θ±0.2° 2θ.

The above form XIII can be prepared by a process comprising crystallizing Eltrombopag from diethyl ether. The crystallization comprises providing a solution of Eltrombopag in diethyl ether and precipitating the crystalline form. The solution can be provided by combining Eltrombopag and diethyl ether; and heating the combination, for instance, to a temperature at which a solution is formed. Precipitation can be achieved, for example, by cooling the solution to obtain a suspension comprising the crystalline form. A suitable cooling temperature is, for example, about room temperature, about 22° C. The obtained crystalline form can then be recovered from the suspension. The recovery can comprise filtering the crystalline form and maintaining the recovered solid. Maintaining can be done at about room temperature.

Figure 18:
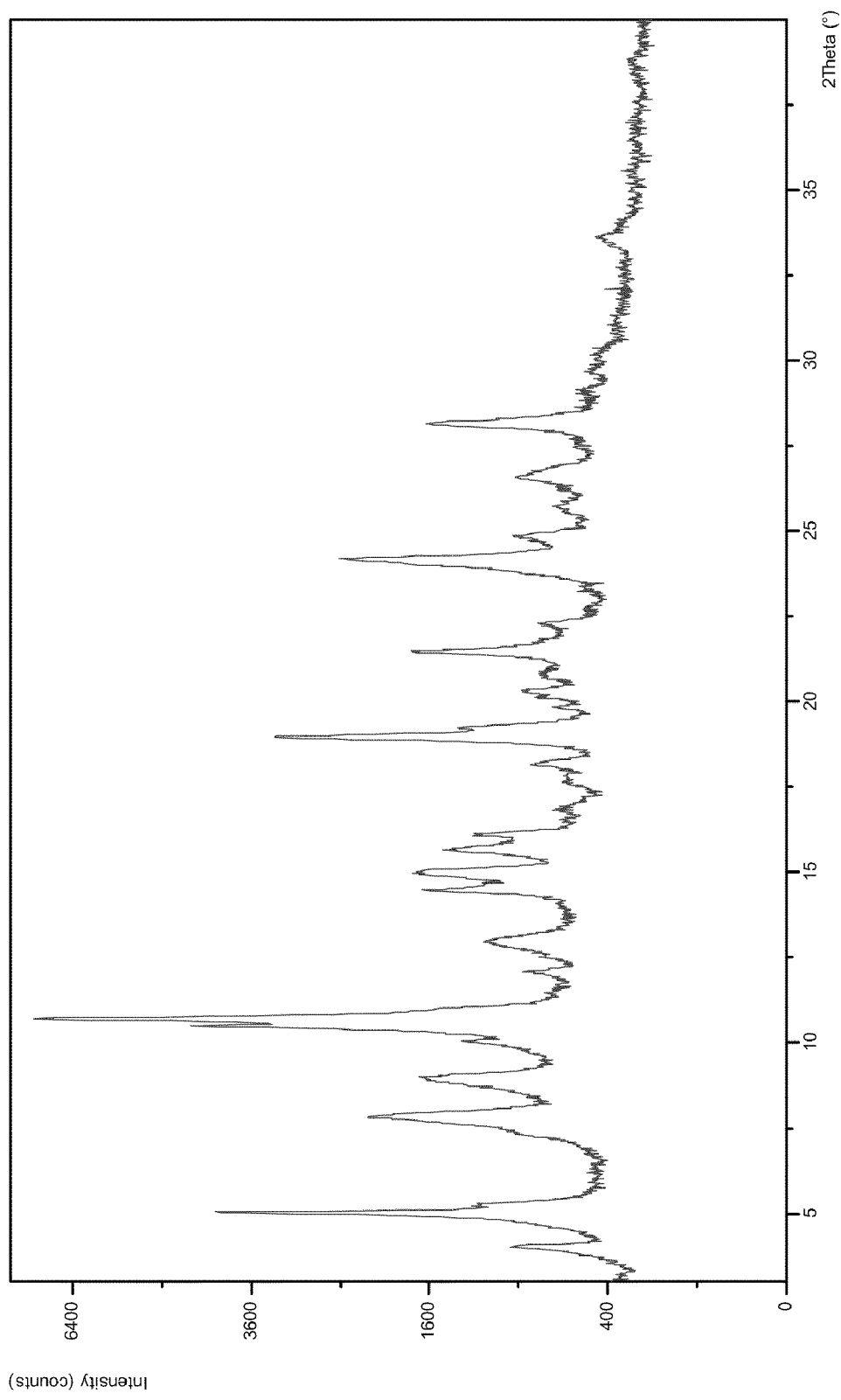
FIG. 18 shows a powder XRD pattern of crystalline Eltrombopag form XIV.

In another embodiment the present invention encompasses crystalline Eltrombopag characterized by a data selected from a group consisting of: powder XRD pattern having peaks at 5.0, 10.7, 19.0 and 21.4° 2θ±0.2° 2θ; a PXRD pattern as depicted in FIG. 18; and any combination thereof. This crystalline form of Eltrombopag is designated herein as form XIV. The above form XIV of Eltrombopag can be further characterized by a powder XRD pattern having peaks at 4.0, 7.9, 9.1 and 15.1° 2θ±0.2° 2θ.

The above form XIV can be prepared by a process comprising crystallizing Eltrombopag from ethyl acetate. The crystallization comprises providing a solution of Eltrombopag in ethyl acetate and precipitating the crystalline form. The solution can be provided by combining Eltrombopag and ethyl acetate; and heating the combination, for example, to a temperature at which a solution is formed. Precipitation can be achieved, for example, by cooling the solution to obtain a suspension comprising the crystalline form. The cooling temperature can be a temperature such as about room temperature, e.g. about 22° C. The obtained crystalline form can then be recovered from the suspension. The recovery can comprise filtering the crystalline form and maintaining the recovered solid. Maintaining can be done at about room temperature.

Figure 19:
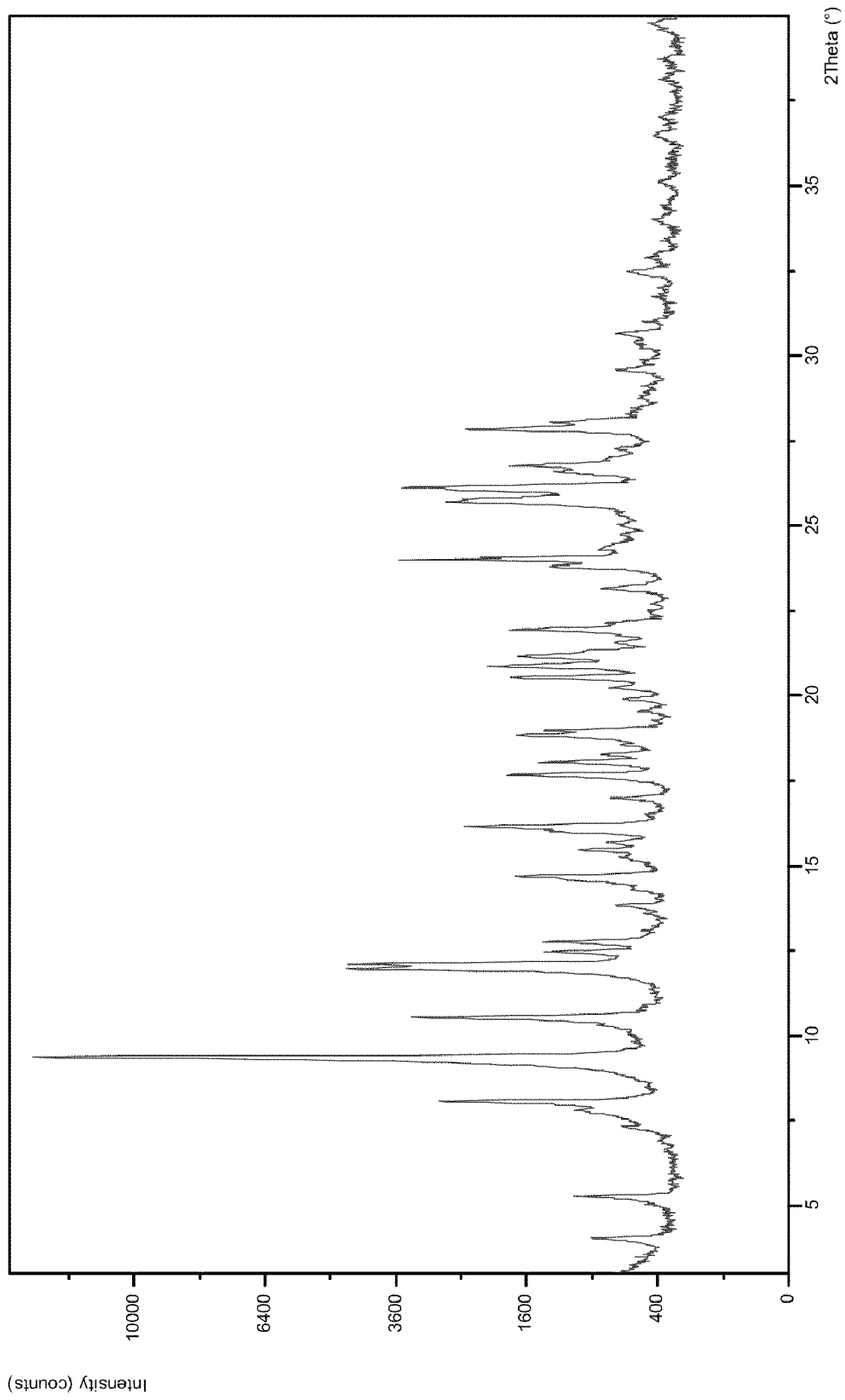
FIG. 19 shows a powder XRD pattern of crystalline Eltrombopag form XV.

In yet another embodiment the present invention encompasses crystalline Eltrombopag characterized by a data selected from a group consisting of: powder XRD pattern having peaks at 11.5 12.0, 12.5 and 20.9° 2θ±0.2° 2θ; a PXRD pattern as depicted in FIG. 19; and any combination thereof. This crystalline form of Eltrombopag is designated herein as form XV. The above form XV of Eltrombopag can be further characterized by a powder XRD pattern having peaks at 4.0, 8.1, 9.4, 16.2 and 27.8° 2θ±0.2° 2θ.

The above form XV can be prepared by a process comprising heating crystalline Eltrombopag form X to a temperature from about 155° C. to about 163°, or from about 160°. A suitable heating rate can be a rate of about 10° C. per minute. Heating can be done, for example, under nitrogen.

In one embodiment the present invention encompasses crystalline Eltrombopag characterized by a data selected from a group consisting of: powder XRD pattern having peaks at 7.1, 9.5, 13.9, 21.2 and 25.5° 2θ±0.2° 2θ; a PXRD pattern as depicted in FIG. 20; a solid state $^{13}$C NMR spectrum having peaks at 168.7, 156.7, 127.6 and 112.8±0.2 ppm; a solid state $^{13}$C NMR spectrum as depicted in FIG. 38; and any combination thereof. This crystalline form of Eltrombopag is designated herein as form XVI.

Figure 21:
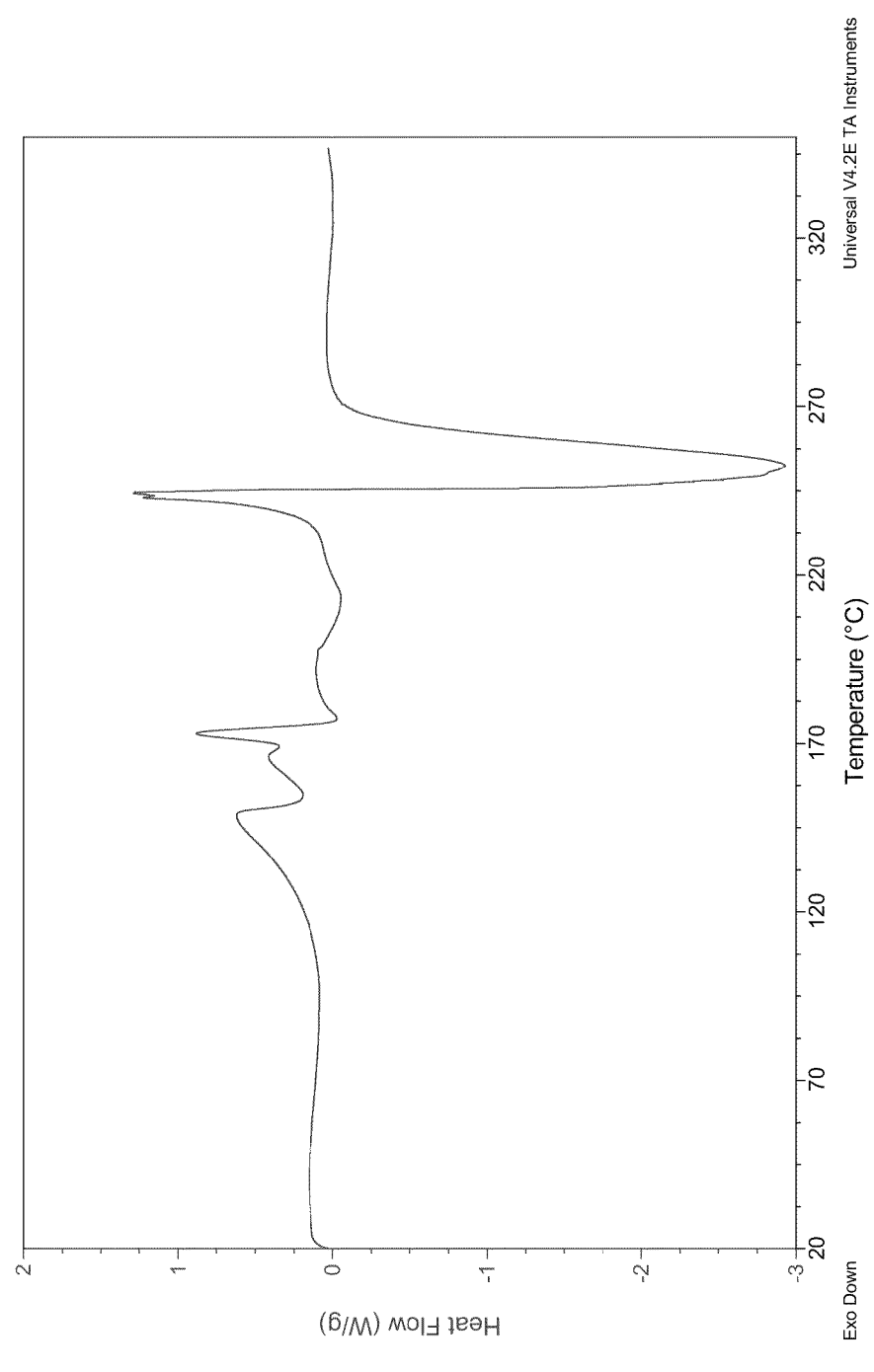
FIG. 21 shows a DSC thermogram of Eltrombopag form XVI.

The above form XVI of Eltrombopag can be further characterized by data selected from a group consisting of: a powder XRD pattern having peaks at 5.9, 11.2, 15.4, 17.4 and 26.2° 2θ±0.2° 2θ; a DSC thermogram as depicted in FIG. 21; a solid state $^{13}$C NMR spectrum having peaks at 146.4, 140.7, 136.3 and 117.3±0.2 ppm; and any combination thereof.

The above crystalline Eltrombopag form XVI is a monohydrate form.

Crystalline Eltrombopag form XVI has advantageous properties selected from at least one of: chemical purity, flowability, solubility, morphology or crystal habit, stability—such as storage stability, stability to dehydration, stability to polymorphic conversion, low hygroscopicity, low content of residual solvents. Particularly, the crystalline Eltrombopag form XVI of the present invention have advantageous chemical purity, it is non-hygroscopic in relative humidity ("RH") of 80%, 100% at room temperature, for a period of at least 5 months and it is highly crystalline and has enhanced powder flowability.

Preferably, crystalline Eltrombopag form XVI of the present invention is substantially free of any other polymorph forms.

The above form XVI can be prepared by a process comprising reacting crystalline 3'-amino-2'-hydroxybiphenyl-3-carboxylic acid ("BPCA") form II and crystalline 1-(3,4-dimethylphenyl)-3-methyl-1H-pyrazol-5-ol ("Pyrazole") from II in methanol to obtain Eltrombopag from XVI. BCPA form II can be obtained, for example, from Topharman Shangai Co., Ltd, Batch No: 090921 BPCA. Pyrazole form II can be obtained, for example, from Topharman Shangai Co., Ltd, Batch No: 090805PYRAZOL.

Crystalline Eltrombopag form XVI of the present invention can be used to prepare other forms of Eltrombopag and Eltrombopag ethanolamine salt, in particular crystalline Eltrombopag form I. In certain embodiments, the present invention provides a process for preparing crystalline Eltrombopag form I, comprising preparing crystalline Eltrombopag form XVI by reacting crystalline BPCA form II and crystalline pyrazole form II to obtain crystalline Eltrombopag from XVI and converting the obtained crystalline Eltrombopag from XVI to crystalline Eltrombopag form I by a process comprising crystallizing or suspending Eltrombopag form XVI in glacial acetic acid.

The present invention describes crystalline forms of Eltrombopag intermediates 1-(3,4-dimethylphenyl)-3-methyl-1H-pyrazol-5-ol ("pyrazole") and 3'-amino-2'-hydroxybiphenyl-3-carboxylic acid ("BPCA").

Figure 33:
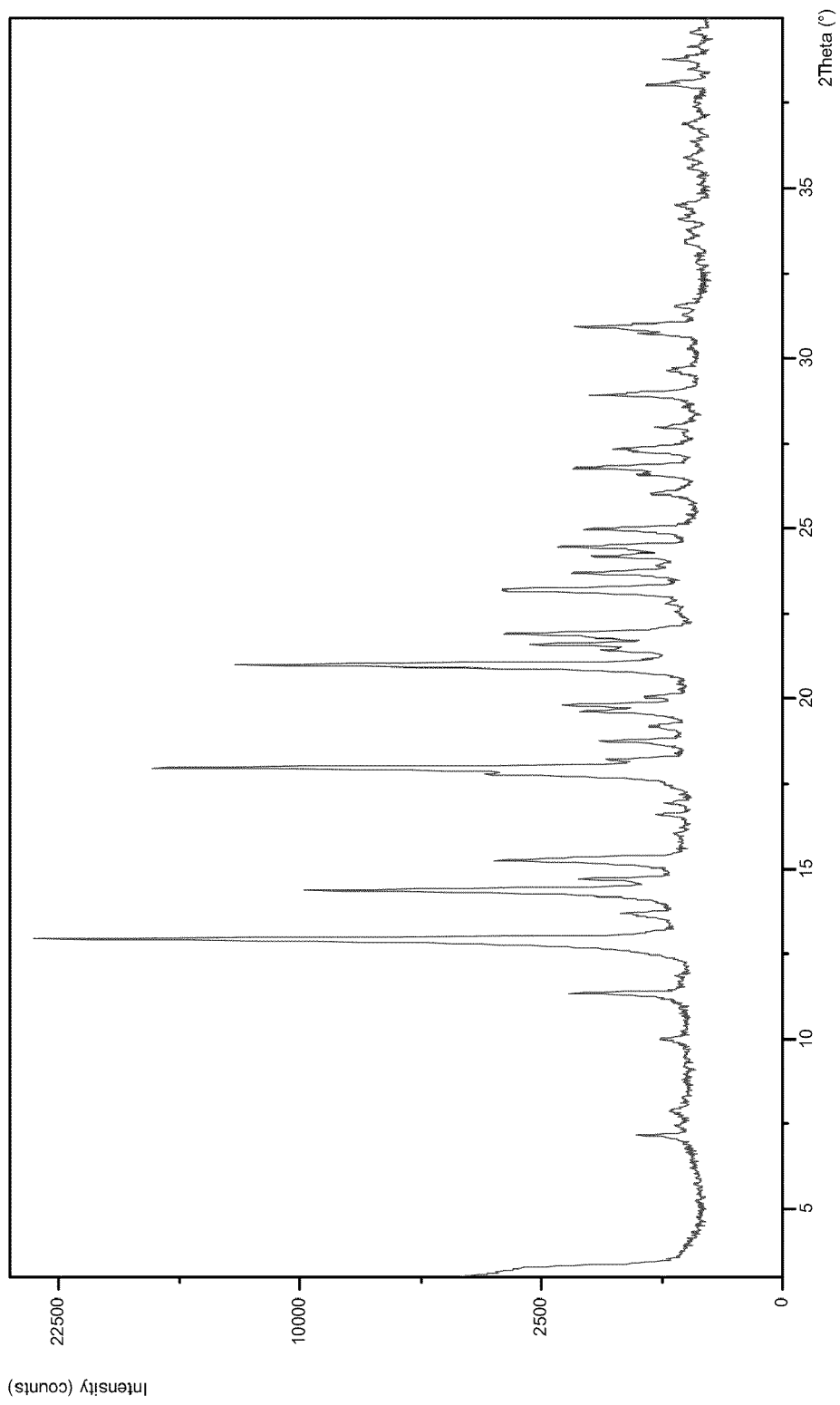
FIG. 33 shows a powder XRD pattern of crystalline 1-(3,4-dimethylphenyl)-3-methyl-1H-pyrazol-5-ol ("pyrazole") form II.

Crystalline pyrazole form II is characterized by a PXRD pattern as depicted in FIG. 33.

Figure 34:
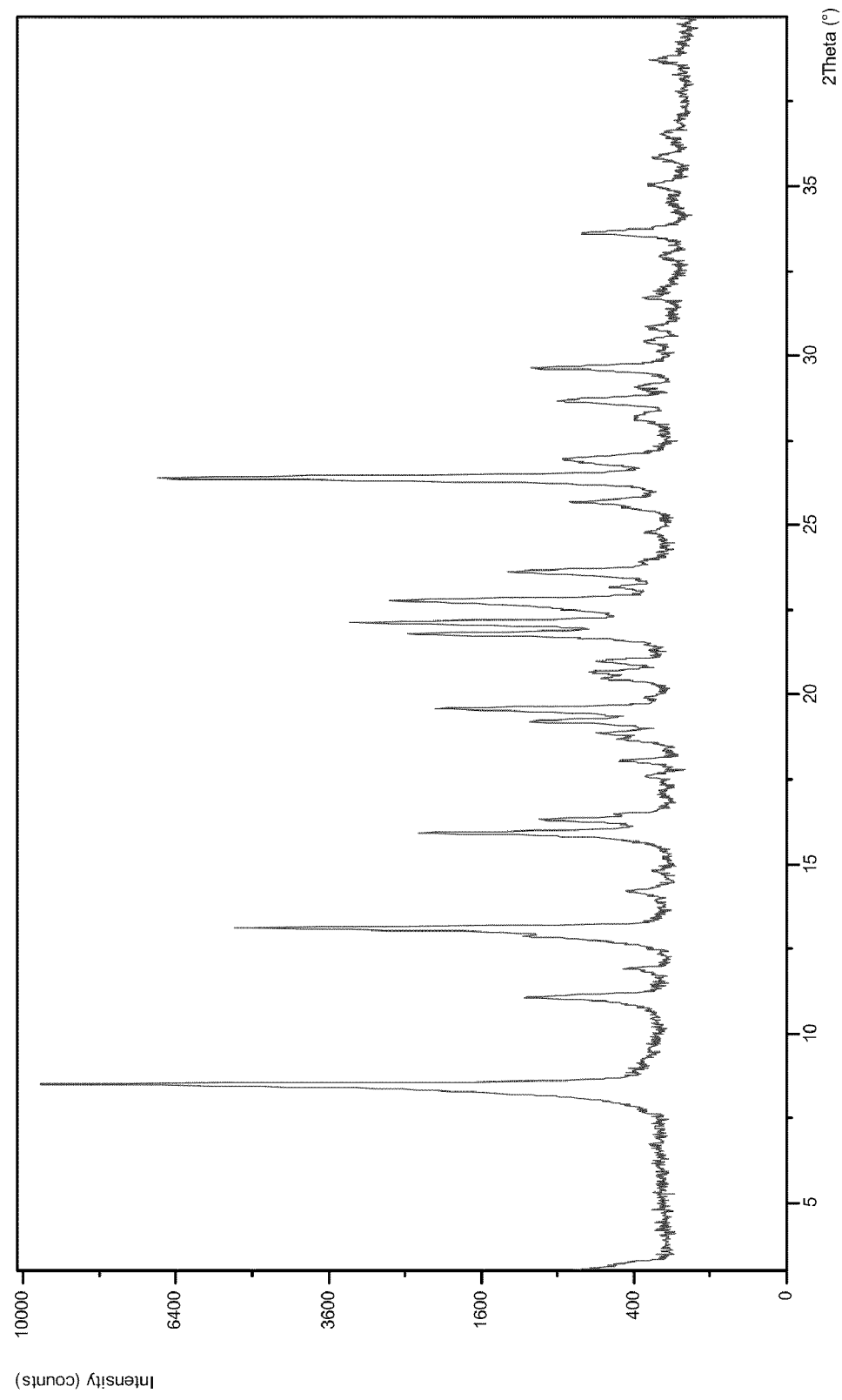
FIG. 34 shows a powder XRD pattern of crystalline 3'-amino-2'-hydroxybiphenyl-3-carboxylic acid ("BPCA") form II.

Crystalline BPCA form II is characterized a PXRD pattern described in FIG. 34.

The present invention provides a process for preparing Eltrombopag and Eltrombopag ethanolamine salt, comprising a) providing crystalline Eltrombopag form III or crystalline Eltrombopag form XVI; b) converting the crystalline Eltrombopag form III or crystalline Eltrombopag form XVI obtained in step (a) to crystalline Eltrombopag form I; c) converting the crystalline Eltrombopag form I obtained in step (b) to crystalline Eltrombopag form V; and optionally d) converting the crystalline Eltrombopag form V obtained in step (c) to Eltrombopag ethanolamine salt. Each of the described steps in this said process can be done according to the processes described above, for each of the described polymorph.

The above process provides Eltrombopag ethanolamine salt in high chemical purity of at least 99%, 99.5%, 99.9 or 99.95%, as measured by HPLC.

Each of the above described polymorphs of Eltrombopag can be used to prepare pharmaceutical formulations.

The present invention provides a pharmaceutical formulation comprising any one, or combination, of the above described polymorphs of Eltrombopag, and at least one pharmaceutically acceptable excipient.

Each of the above described crystalline forms of Eltrombopag can also be used to prepare Eltrombopag bisethanolamine or monoethanolamine salts, by reacting any one, or combination, of the above polymorphs of Eltrombopag and ethanolamine.

The process for preparing Eltrombopag ethanolamine salt can comprise preparing any one, or combination, of the above polymorphs of Eltrombopag and converting them to Eltrombopag bisethanolamine or monoethanolamine salt.

Figure 22:
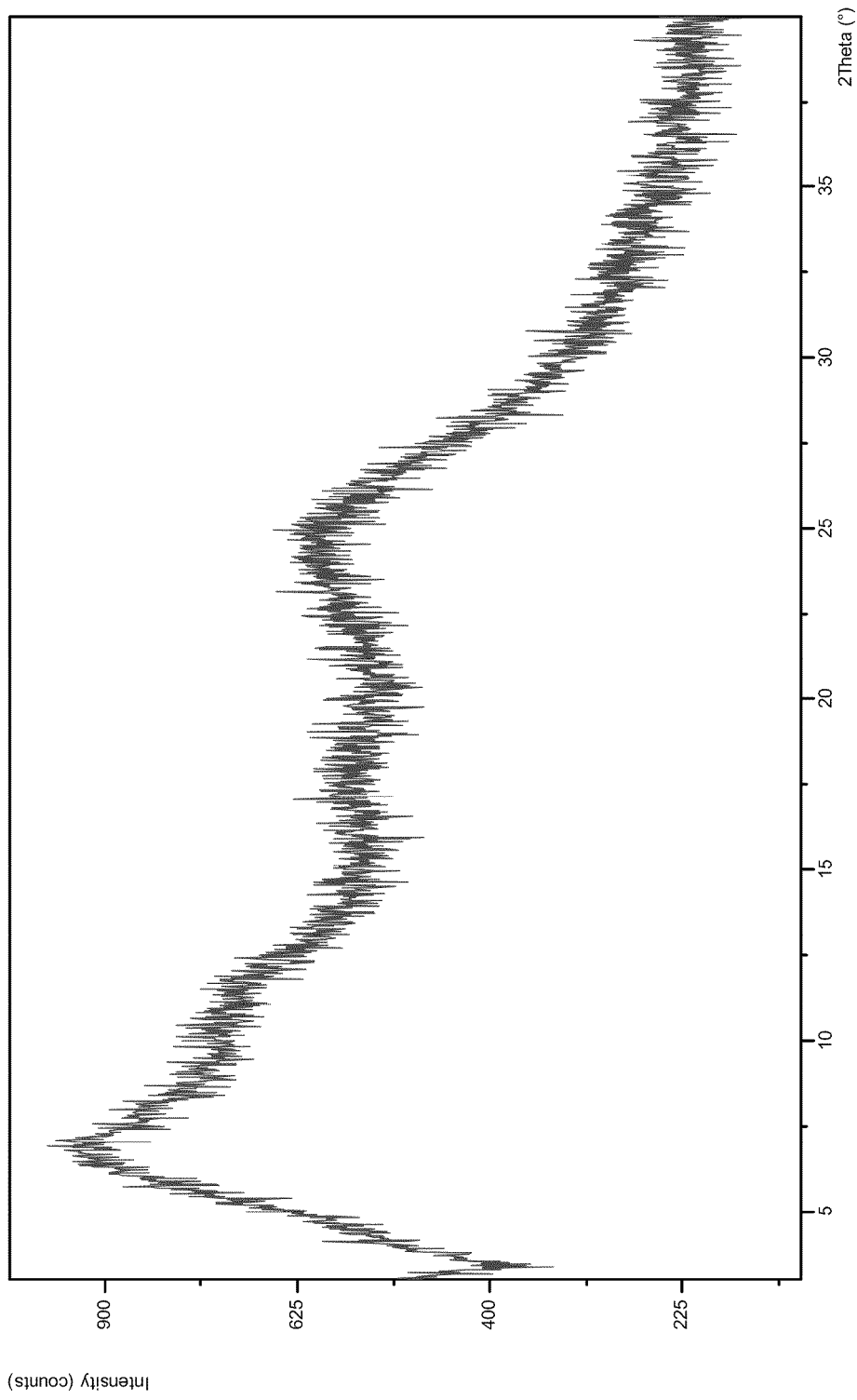
FIG. 22 shows a powder XRD pattern of amorphous Eltrombopag bisethanolamine salt.
Figure 23:
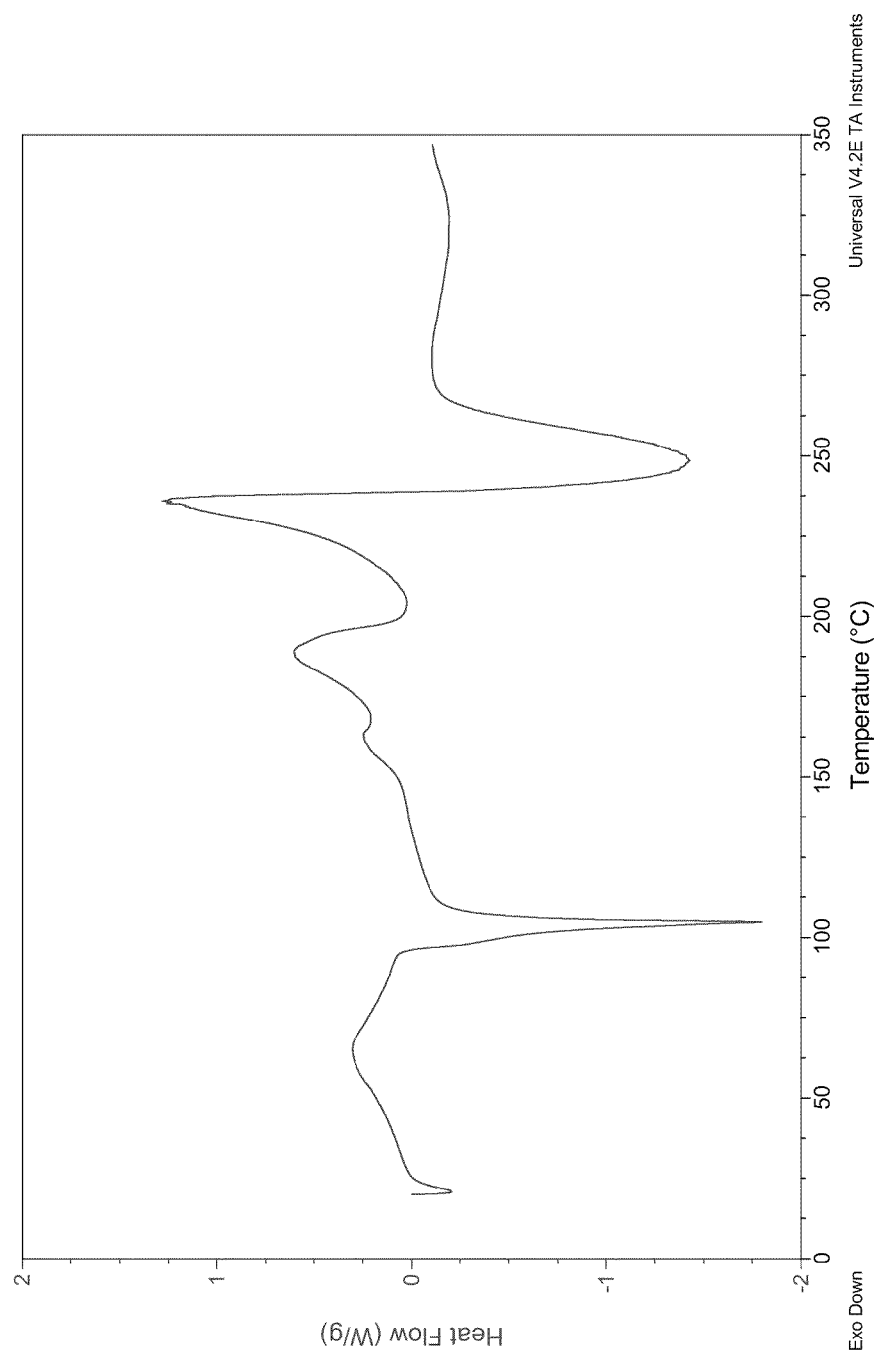
FIG. 23 shows a DSC thermogram of amorphous Eltrombopag bisethanolamine salt.

In one embodiment the present invention encompasses amorphous Eltrombopag bisethanolamine salt. The amorphous Eltrombopag bisethanolamine salt can be characterized by a PXRD pattern as depicted in FIG. 22. The amorphous Eltrombopag bisethanolamine salt can be further characterized by a DSC thermogram as depicted in FIG. 23.

The above amorphous Eltrombopag bisethanolamine salt can be prepared by a process comprising grinding Eltrombopag bisethanolamine salt in the absence of a solvent, i.e., dry grinding.

Figure 24:
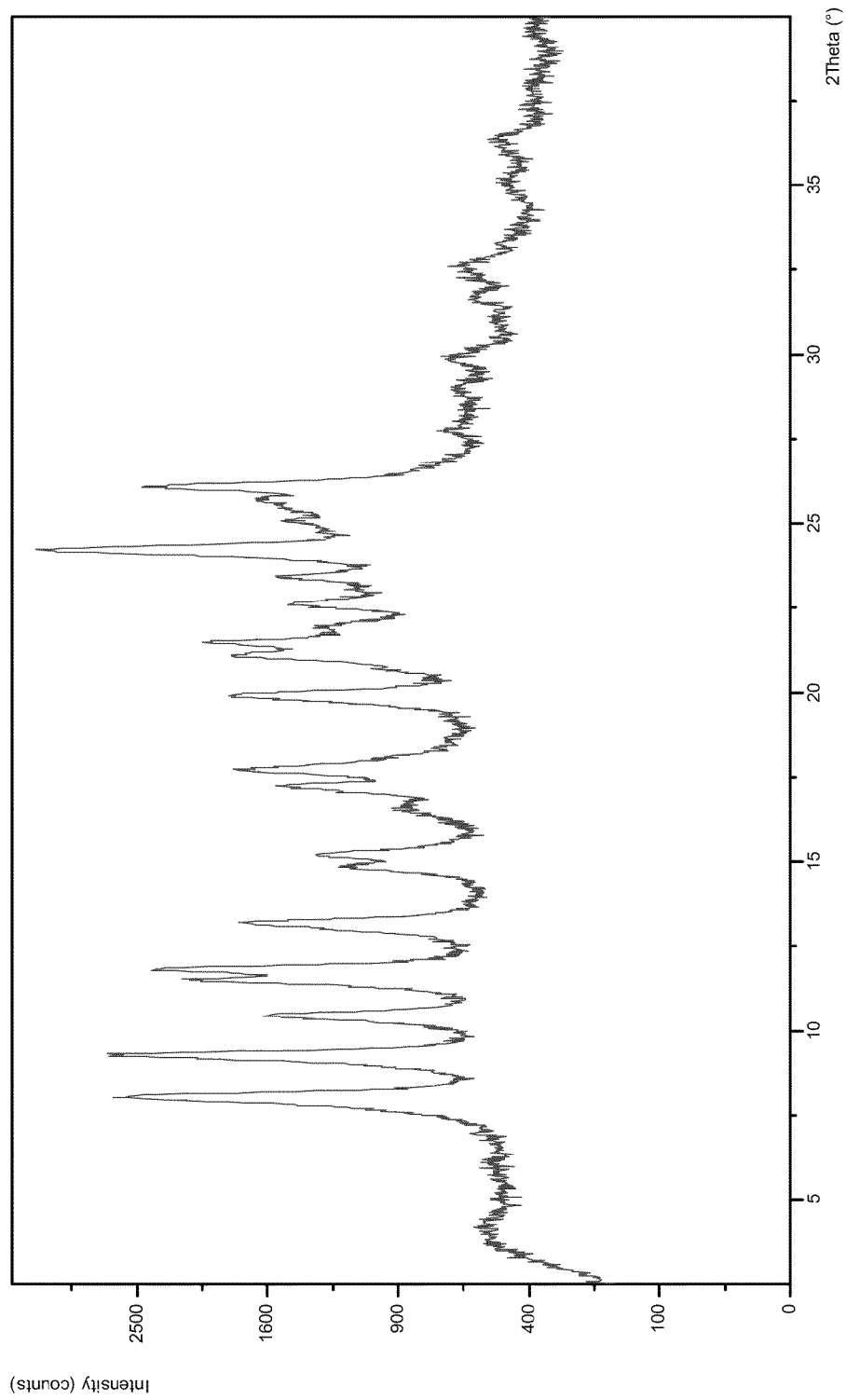
FIG. 24 shows a powder XRD pattern of crystalline Eltrombopag bisethanolamine salt designated form II.
Figure 39:
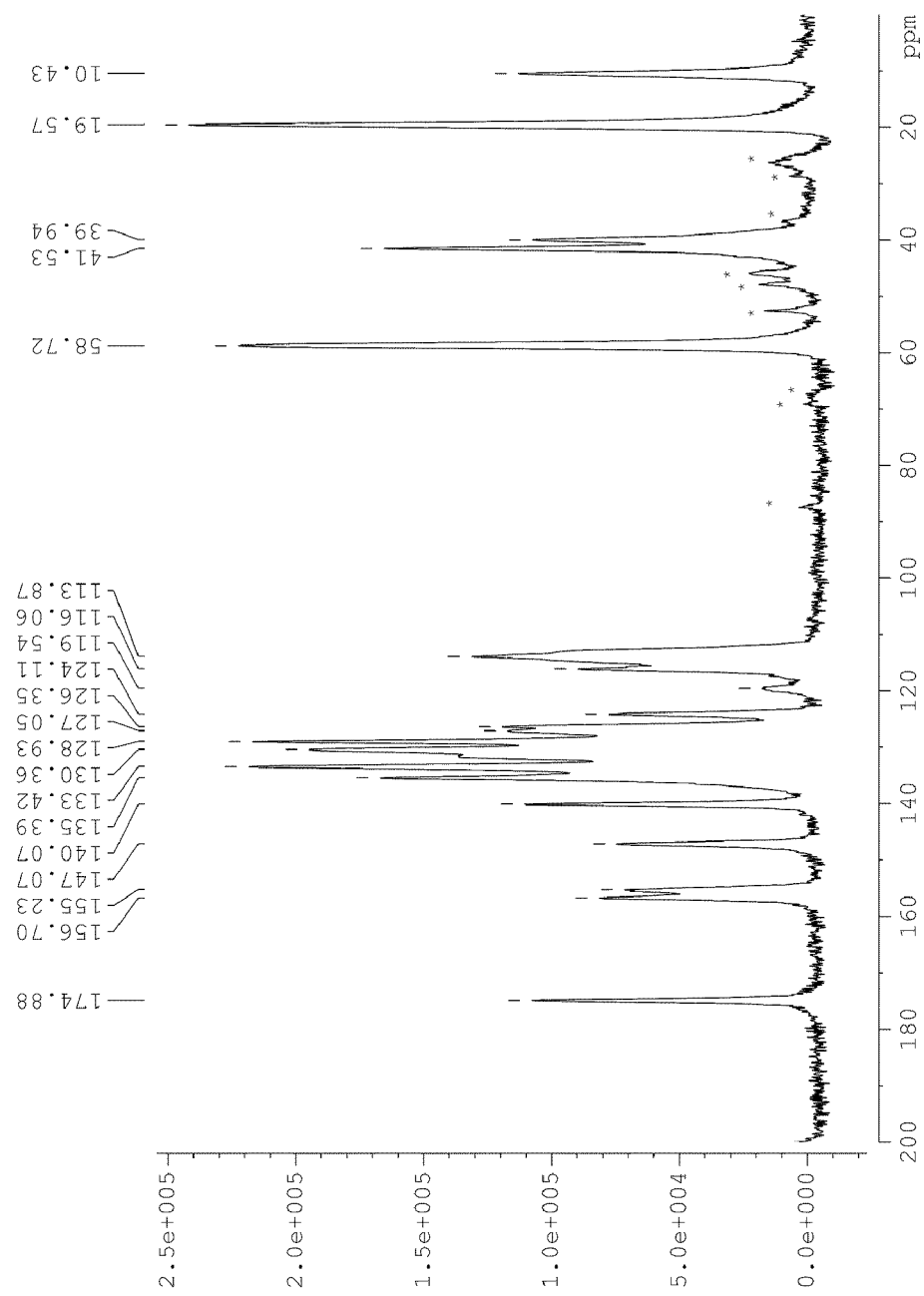
FIG. 39 shows a solid state $^{13}$C NMR spectrum of crystalline Eltrombopag bisethanolamine salt designated form II.

In another embodiment the present invention encompasses crystalline Eltrombopag bisethanolamine salt characterized by data selected from a group consisting of: powder XRD pattern having peaks at 9.3, 11.8, 13.2 and 17.7° 2θ±0.2° 2θ; a PXRD pattern as depicted in FIG. 24; a solid state $^{13}$C NMR spectrum having peaks at 174.9, 147.1, 135.4 and 58.7±0.2 ppm; a solid state $^{13}$C NMR spectrum as depicted in FIG. 39; and any combination thereof. This crystalline form of Eltrombopag bisethanolamine salt is designated herein as form II.

Figure 25:
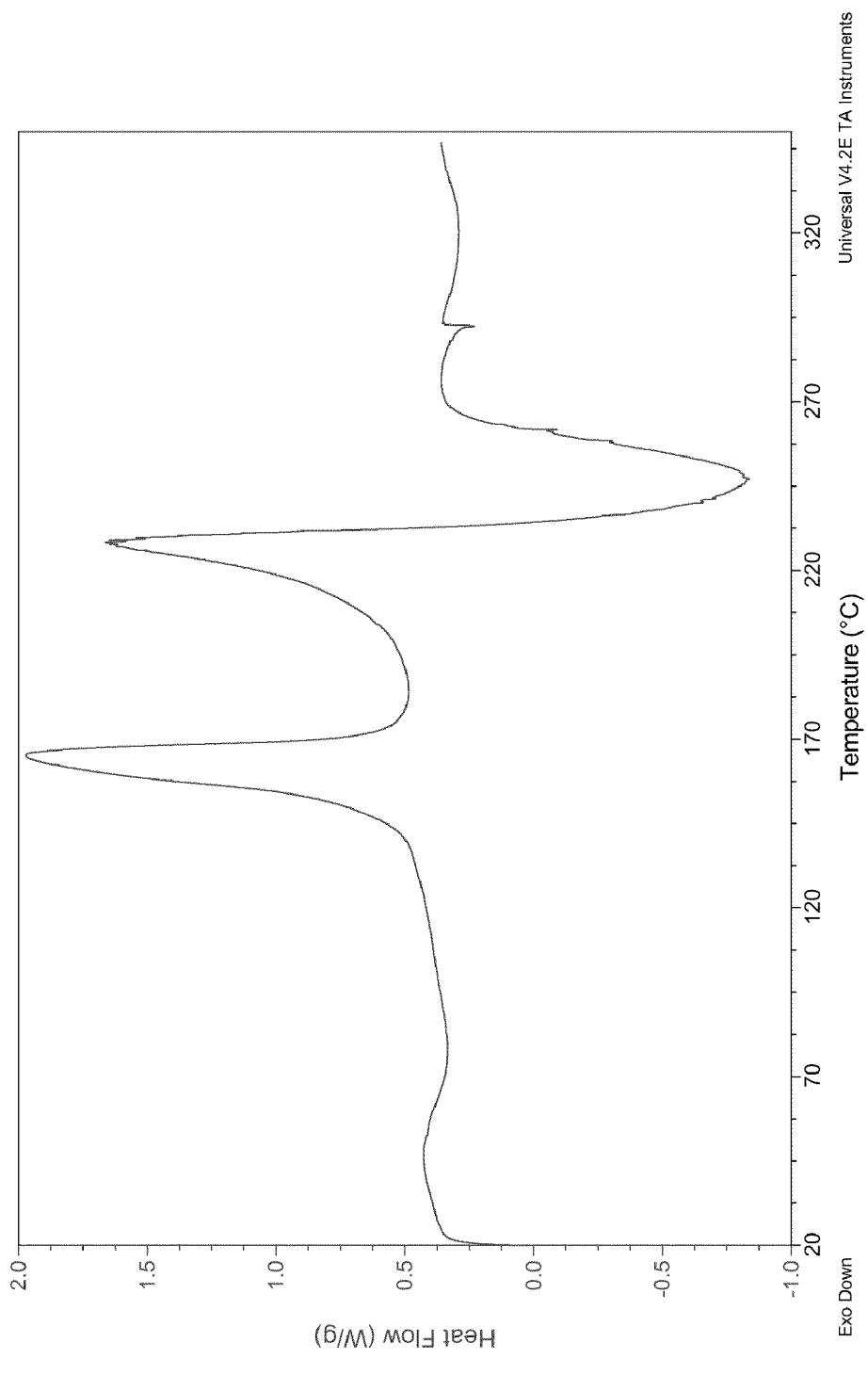
FIG. 25 shows a DSC thermogram crystalline Eltrombopag bisethanolamine salt designated form II.

The above form II of Eltrombopag bisethanolamine salt can be further characterized by data selected from a group consisting of: a powder XRD pattern having peaks at 8.1, 15.2, 22.6 and 26.1° 2θ±0.2° 2θ; a DSC thermogram as depicted in FIG. 25; a solid state $^{13}$C NMR spectrum having peaks at 156.7, 130.4, 126.4 and 113.9±0.2 ppm; and any combination thereof.

Crystalline Eltrombopag bisethanolamine form II has advantageous properties selected from at least one of: chemical purity, flowability, solubility, morphology or crystal habit, stability—such as storage stability, stability to dehydration, stability to polymorphic conversion, low hygroscopicity, low content of residual solvents. Particularly, the crystalline Eltrombopag bisethanolamine form II of the present invention has advantageous chemical purity and it is highly soluble in water.

In a preferred embodiment, the above form II is polymorphically pure. As used herein the term polymorphically pure form II corresponds to composition containing Eltrombopag bisethanolamine salt form II and not more than about 10% by weight, not more than 5%, in particular, not more than 1% preferably 1%-10%, 1%-5%, in particular 1% or less by weight, of form I of bisethanolamine salt characterized by a PXRD pattern having peaks at 7.5, 8.3, 14.0 and 23.0° 2θ±0.2° 2θ, designated form I of bisethanolamine salt.

The amount of Eltrombopag bisethanolamine salt form I and form II in the composition can be measured by PXRD. For example, the amount of form I can be measured by any one of the peaks at 7.5, 8.3 and 14.0° 2θ±0.2° 2θ; and the amount of form II can be measured by any one of the peaks at 9.3, 11.8 and 13.2° 2θ±0.2° 2θ.

The above form II of Eltrombopag bisethanolamine salt can be prepared by a process comprising grinding amorphous Eltrombopag bisethanolamine salt in the presence of methyl tert-butyl ether (MTBE). A sufficient amount of MTBE should be added to obtain Form II. Preferably, to maximize yield, as much MTBE as possible should be added without transforming the solid into a paste. See, e.g., Example 25.

Figure 26:
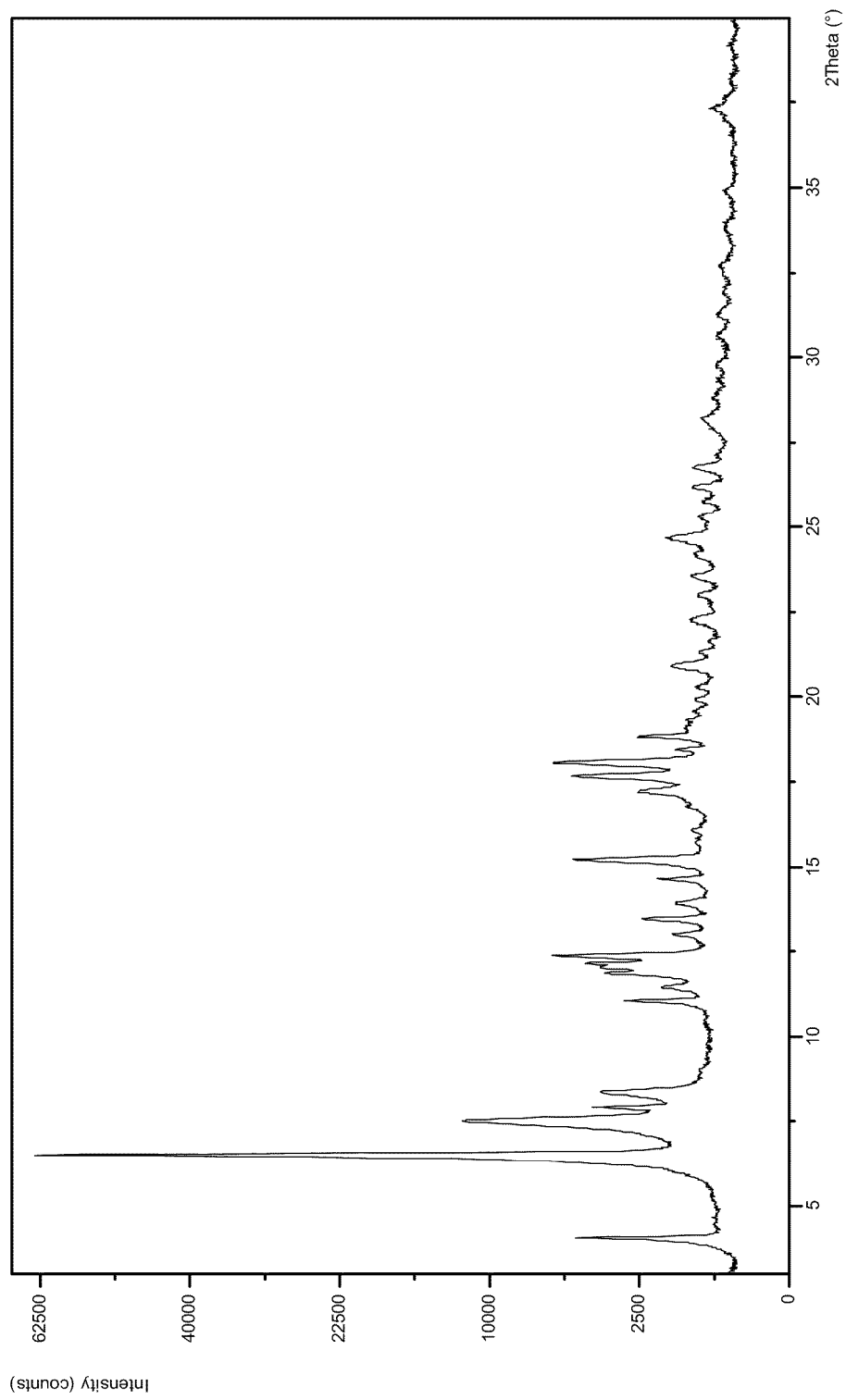
FIG. 26 shows a powder XRD pattern of crystalline Eltrombopag bisethanolamine salt designated form III.

In one embodiment the present invention encompasses crystalline Eltrombopag bisethanolamine salt characterized by data selected from a group consisting of: powder XRD pattern having peaks at 4.1, 6.5, 15.2 and 18.1° 2θ±0.2° 2θ; a PXRD pattern as depicted in FIG. 26; and any combination thereof. This crystalline form of Eltrombopag bisethanolamine salt is designated herein as form III.

Figure 27:
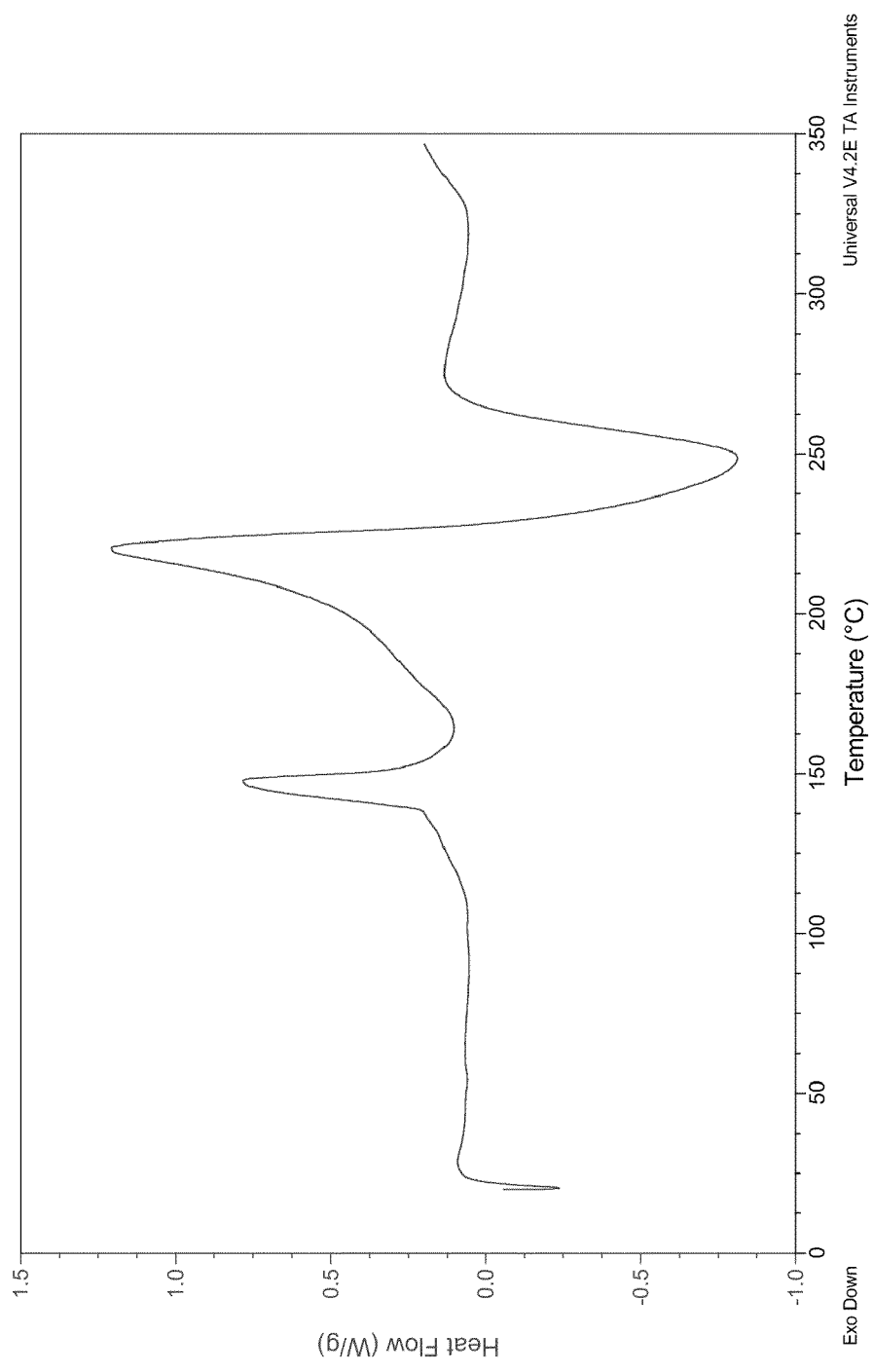
FIG. 27 shows a DSC thermogram crystalline Eltrombopag bisethanolamine salt designated form III.

The above form III of Eltrombopag bisethanolamine salt can be further characterized by data selected from a group consisting of: a powder XRD pattern having peaks at 11.9, 13.5, 14.6 and 17.7° 2θ±0.2° 2θ; a DSC thermogram as depicted in FIG. 27; and any combination thereof.

The above form III of Eltrombopag bisethanolamine salt can be prepared by a process comprising slurrying amorphous Eltrombopag bisethanolamine salt in cumen, i.e., isopropylbenzene. Slurrying can be done for a period of about a day. The form III can than be recovered from the slurry, for example, by drying, e.g. by air drying.

Figure 28:
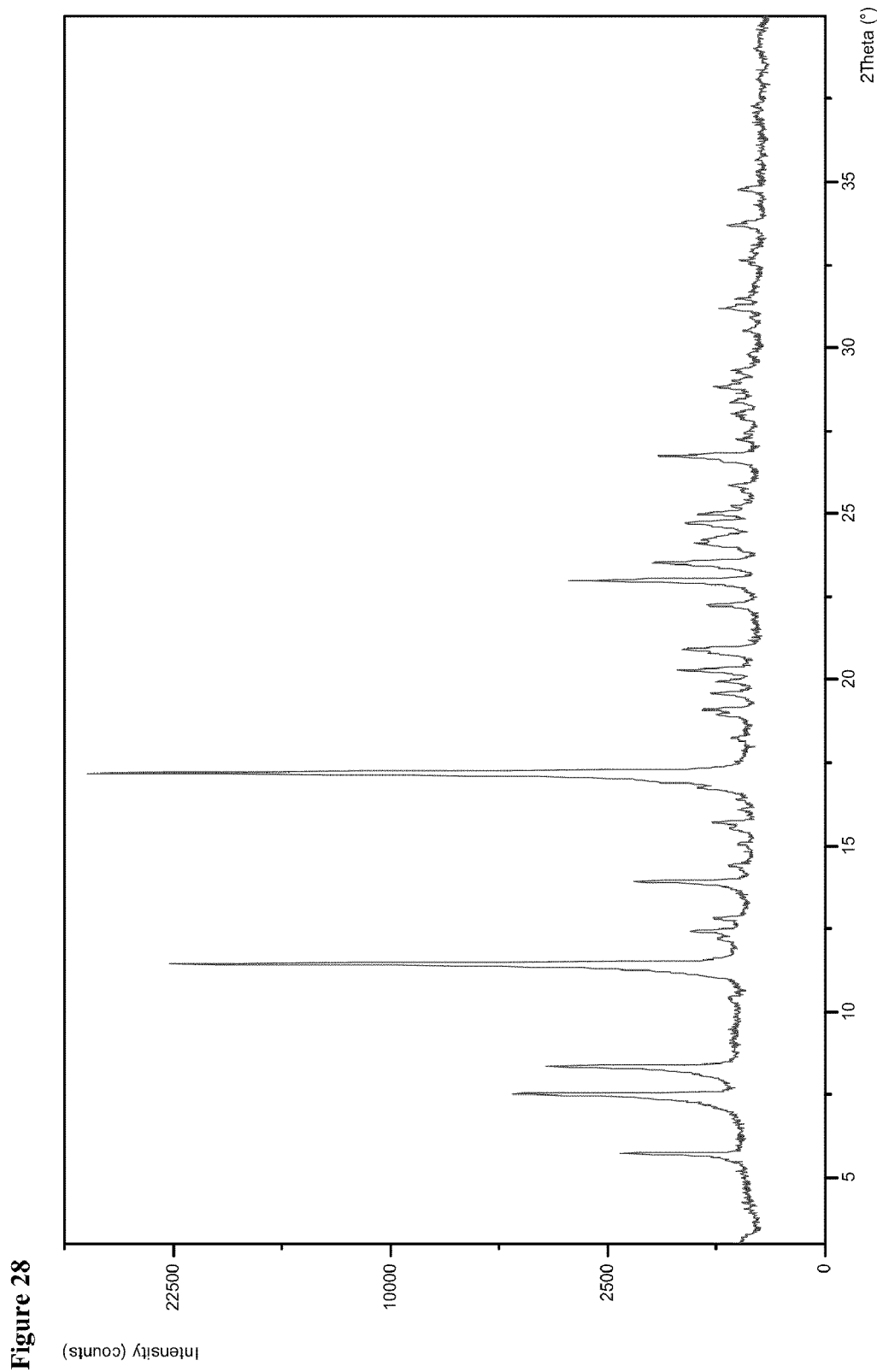
FIG. 28 shows a powder XRD pattern of crystalline Eltrombopag bisethanolamine salt designated form I.
Figure 40:
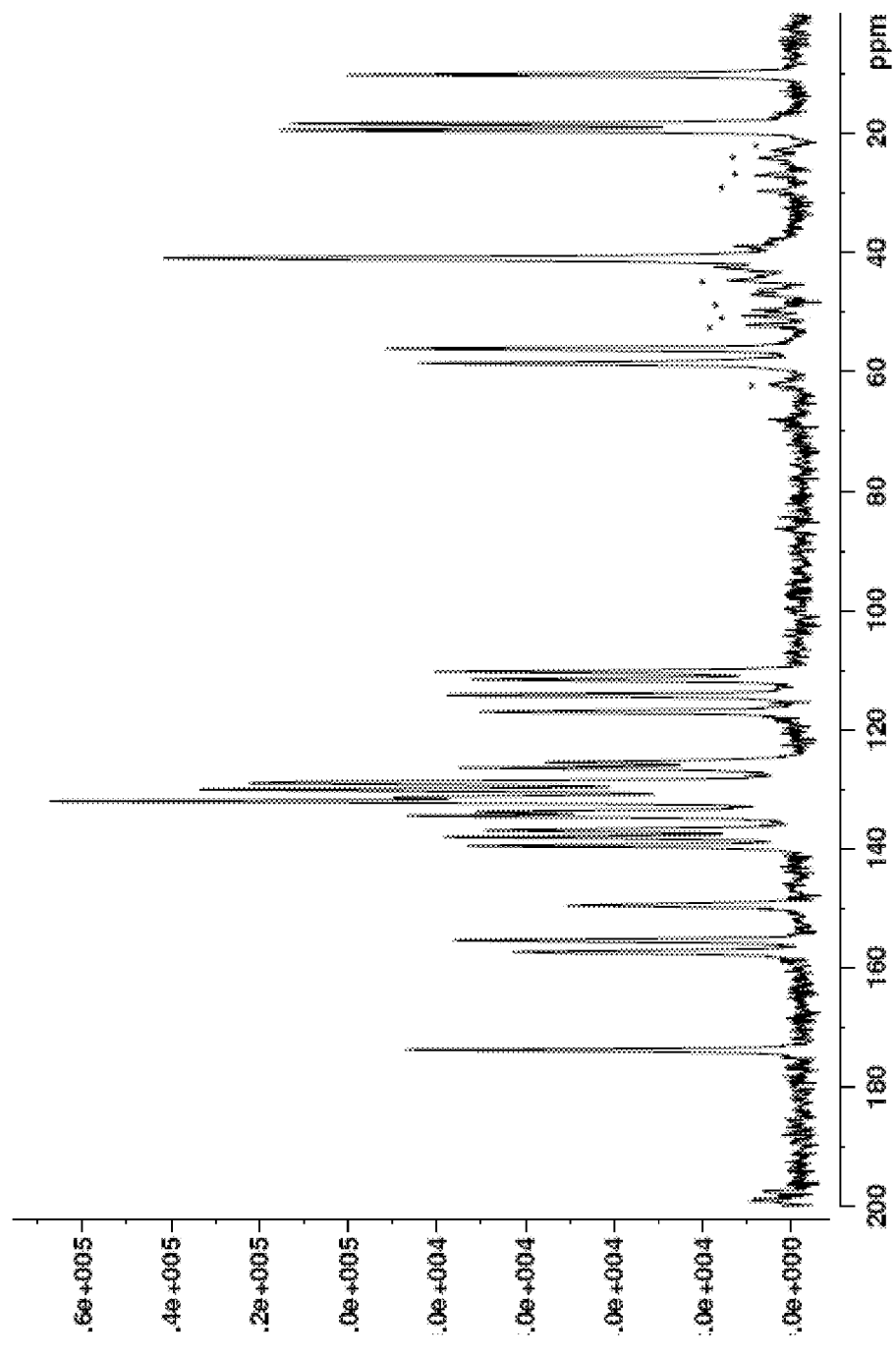
FIG. 40 shows a solid state $^{13}$C NMR spectrum of crystalline Eltrombopag bisethanolamine salt designated form I.

The present invention describes crystalline Eltrombopag bisethanolamine salt characterized by a data selected from a group consisting of: powder XRD pattern having peaks at 7.5, 8.3, 14.0 and 23.0° 2θ±0.2° 2θ; a PXRD pattern as depicted in FIG. 28; a solid state $^{13}$C NMR spectrum as depicted in FIG. 40; and any combination thereof. This crystalline form of Eltrombopag bisethanolamine salt is designated herein as form I. The above form I of Eltrombopag bisethanolamine salt can be further characterized by a powder XRD pattern having peaks at 5.7, 11.4, 17.2 and 26.7° 2θ±0.2° 2θ.

In a more preferred embodiment, the above form I is polymorphically pure. As used herein the term polymorphically pure form I corresponds to composition containing Eltrombopag bisethanolamine salt form I and not more than about 10% by weight, not more than 5%, particularly, not more than 1% by weight, of form II of bisethanolamine salt characterized by a PXRD pattern having peaks at 9.3, 11.8, 13.2 and 17.7° 2θ±0.2° 2θ, designated form II of bisethanolamine salt.

The amount of Eltrombopag bisethanolamine salt form I and form II in the composition can be measured by PXRD. For example, the amount of form I can be measured by any one of the peaks at 7.5, 8.3 and 14.0° 2θ±0.2° 2θ; and the amount of form II can be measured by any one of the peaks at 9.3, 11.8 and 13.2° 2θ±0.2° 2θ.

The above form I of Eltrombopag bisethanolamine salt can be prepared by a process comprising reacting Eltrombopag and ethanolamine in a solvent selected from a group consisting of: ethanol, methanol, tetrahydrofuran (THF), and a mixture of THF and water. The process comprises providing a reaction mixture of Eltrombopag and ethanolamine in the solvent and precipitating the crystalline form.

The reaction mixture can be provided by combining Eltrombopag or a suspension of Eltrombopag in the solvent and ethanolamine or a solution of ethanolamine in the solvent, wherein the solvent of Eltrombopag and ethanolamine can be same or different. The suspension of Eltrombopag and the solution of ethanolamine can be heated prior to the combining step, for example to a temperature such as reflux temperature. For example, when using ethanol and methanol as solvents for Eltrombopag and for ethanolamine the suspension of Eltrombopag and the solution of ethanolamine are heated, and when using THF or a mixture of THF and water the combination step is done at a temperature of about room temperature, i.e., without heating the suspension of Eltrombopag and the solution of ethanolamine.

After the reaction mixture is provided it can be further maintained, for example at the same temperature of the combination step, over a period of about 30 minutes to about 45 minutes. Precipitation is achieved, for example, by cooling the reaction mixture to obtain a suspension comprising the crystalline form. Cooling can be to a temperature in a range from about room temperature to about 0° C., over a period of about 0.5 hour to about 19 hours. For example, when using ethanol cooling is done for about 1.5 hours to about 2 hours and when using methanol cooling is done over a period of about 0.5 hour to about 19 hours. The Eltrombopag bisethanolamine form I can then be recovered.

The recovery can comprise, for example, filtering the obtained solid from the suspension, washing and drying. Washing can be done with the solvent used in the suspension of Eltrombopag or the solution of ethanolamine. Drying can be done under vacuum, at pressure such as about 5 mBar. Drying can be done at a temperature from about 20° C. to about 50° C., for example, over a period of about 1.5 hours to about 18 hours. Optionally, the drying can be done at two steps, e.g., drying at a temperature of about 20° C. and then further drying at a temperature of about 50° C. The process for crystallizing Eltrombopag bisethanolamine form I from methanol can be done subsequent to the synthesis of Eltrombopag, without recovering Eltrombopag from the reaction mixture in which it is formed.

The synthesis can be done, for example, by a process comprising combining hydrochloric acid, methanol, 2',3'-dihydroxybiphenyl-3-carboxylic acid (BPCA) and sodium nitrite to obtain a first solution, adding sulfamic acid to obtain a reaction mixture and further adding pyrazole to obtain a solution. The first solution can be cooled, for example to a temperature from about 5° C. to about 0° C. The first solution can be maintained prior to the addition of sulfamic acid, for example at a temperature from about 5° C. to about 0° C. The sulfamic acid can be dissolved in water prior to its addition to the first solution. After the addition of sulfamic acid, the obtained reaction mixture can be maintained, for instance, with stirring, at a temperature from about 5° C. to about 25° C., over a period of about 45 minutes. Then, 1-(3,4-dimethylphenyl)-3-methyl-1H-pyrazol-5-ol ("pyrazole") is added to the reaction mixture and the solution is formed. The solution can be maintained, for example, with stirring, at a temperature of about room temperature, over a period of about 10 minutes to about 15 minutes.

The solution, comprising Eltrombopag, can then be used to prepare Eltrombopag bisethanolamine form I. The process comprises combining the solution and ethanolamine to obtain a suspension from which the crystalline form precipitates. The suspension can be maintained, e.g. upon stirring, over a period of about 45 minutes. The Eltrombopag bisethanolamine form I can then be recovered, for example, by filtering the obtained solid from the suspension.

The present invention also encompasses crystalline Eltrombopag bisethanolamine form I having low ethanol content of less than about 0.5% (5000 ppm) by weight, less than 0.25% (2500 ppm) by weight, or less than about 0.24% (2400 ppm) by weight.

The crystalline Eltrombopag bisethanolamine form I having low ethanol content can be prepared by a process comprising a) providing a mixture of ethanolamine in ethanol; b) heating the mixture to a temperature from about 65° C. to about reflux temperature; c) adding solid Eltrombopag to the mixture; d) heating to reflux; and optionally e) recovering crystalline Eltrombopag bisethanolamine form I.

The present invention also provides crystalline Eltrombopag mono-ethanolamine salt. Eltrombopag mono-ethanolamine salt can be illustrated by the following chemical structure:

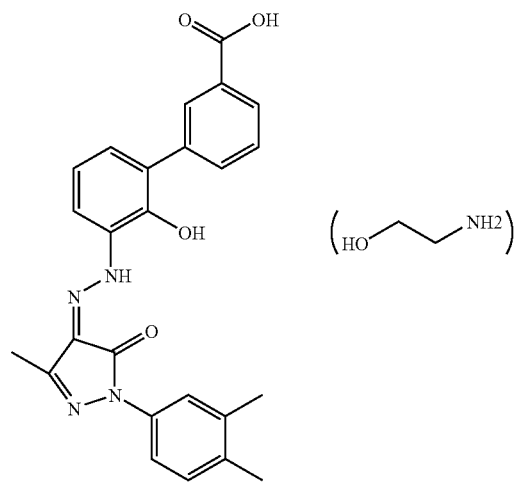

Figure 29:
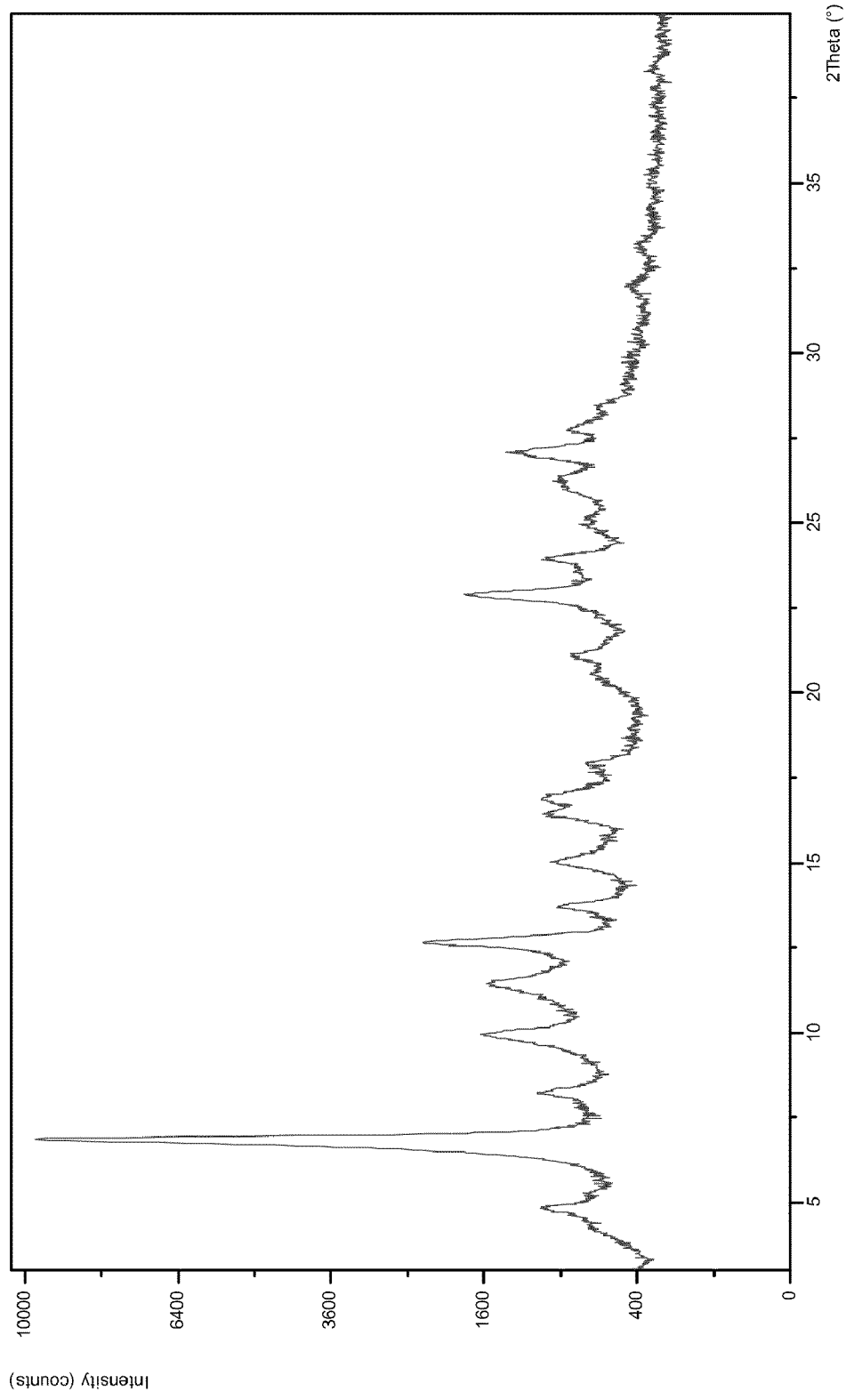
FIG. 29 shows a powder XRD pattern of crystalline Eltrombopag mono-ethanolamine salt designated form H.

In one embodiment the present invention encompasses crystalline Eltrombopag mono-ethanolamine salt characterized by a data selected from a group consisting of: powder XRD pattern having peaks at 4.9, 6.9, 15.1 and 23.0° 2θ±0.2° 2θ; a PXRD pattern as depicted in FIG. 29; and any combination thereof. This crystalline form of Eltrombopag mono-ethanolamine salt is designated herein as form H. The above form H of Eltrombopag mono-ethanolamine salt can be further characterized by a powder XRD pattern having peaks at 9.9, 12.7, 24.0 and 27.1° 2θ±0.2° 2θ.

The above form H can be prepared by a process comprising crystallizing Eltrombopag mono-ethanolamine from a solvent selected from a group consisting of 1-butanol or 1-pentanol. The crystallization comprises providing a solution of Eltrombopag bisethanolamine salt in either 1-butanol or 1-pentanol and precipitating the crystalline form. The solution can be provided by combining Eltrombopag bisethanolamine salt and 1-butanol or 1-pentanol; and heating the combination, to temperature such as about 40° C. to reflux, or about 70° C. Precipitation can be achieved, for example, by cooling the solution to obtain a suspension comprising the crystalline form. A suitable cooling temperature is a temperature, for example, of about room temperature, or about 22° C. The obtained crystalline form can then be recovered from the suspension. The recovery can comprise, for instance, filtering the crystalline form and maintaining the isolated solid, for example at a temperature of about room temperature.

Figure 30:
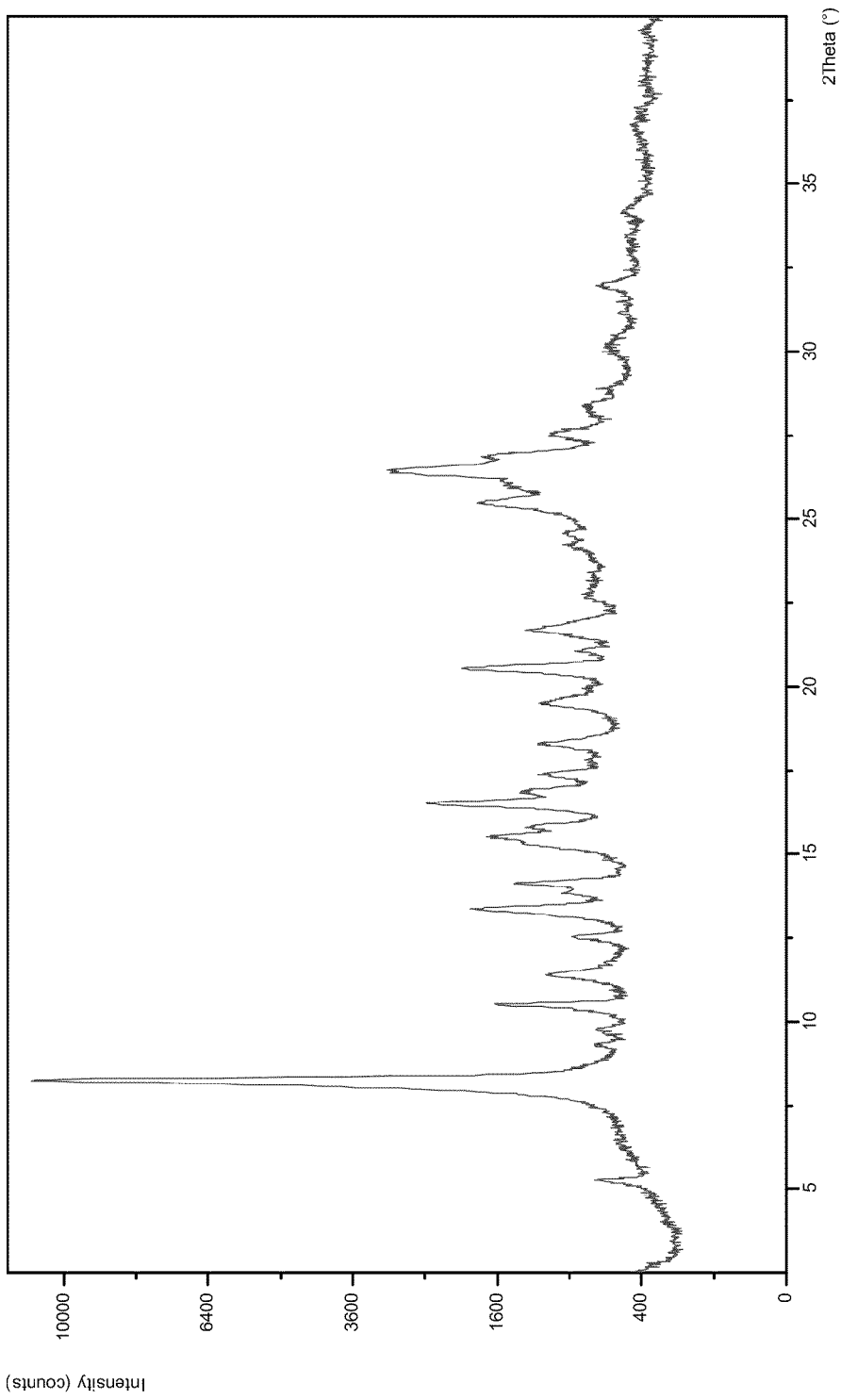
FIG. 30 shows a powder XRD pattern of crystalline Eltrombopag mono-ethanolamine salt designated form E.

In another embodiment the present invention encompasses crystalline Eltrombopag mono-ethanolamine salt characterized by a data selected from a group consisting of: powder XRD pattern having peaks at 10.5, 13.4, 19.5 and 21.7° 2θ±0.2° 2θ; a PXRD pattern as depicted in FIG. 30; and any combination thereof. This crystalline form of Eltrombopag mono-ethanolamine salt is designated herein as form E. The above form E of Eltrombopag mono-ethanolamine salt can be further characterized by a powder XRD pattern having peaks at 8.3, 14.1, 18.3, 25.5 and 26.4° 2θ±0.2° 2θ.

The above crystalline Eltrombopag mono-ethanolamine form E can be prepared by a process comprising drying amorphous Eltrombopag bisethanolamine. The drying process comprises exposing amorphous Eltrombopag bisethanolamine to 2,2,2 trifluoroethanol and further exposing to air. Exposing amorphous Eltrombopag bisethanolamine to 2, 2, 2 trifluoroethanol can be done for a period of about 7 days. Exposing amorphous Eltrombopag bisethanolamine to air is done, for example, for a period of about 24 hours, at a temperature of about 25° C.

The above described crystalline forms of Eltrombopag monoethanolamine and Eltrombopag bisethanolamine salts can be used to prepare pharmaceutical formulations, by any method known in the art.

The present invention provides a pharmaceutical formulation comprising any one, or combination, of the above described polymorphs of Eltrombopag bisethanol-amine and Eltrombopag monoethanolamine salt, and at least one pharmaceutically acceptable excipient.

A. PXRD Method

Samples, after being powdered in a mortar and pestle, are applied directly on silicon plate holder. The X-ray powder diffraction pattern was measured with Philips X'Pert PRO X-ray powder diffractometer, equipped with Cu irradiation source=1.54184 Å (Ångström), X'Celerator (2.022° 2θ) detector. Scanning parameters: angle range: 3-40 deg., step size 0.0167, time per step 50 s or 100s, continuous scan. The accuracy of peak positions was defined as ±0.2 degrees due to experimental differences like instrumentation and sample preparations.

Scanning parameters were as follows:

|  | Scan range | Time per step/s |
|---|---|---|
| EBP acid form | | |
| I | 3-40 | 50 |
| III | 4-40 | 100 |
| IV | 4-40 | 100 |
| V | 4-40 | 100 |
| VI | 3-40 | 100 |
| VII | 3-40 | 100 |
| VIII | 3-40 | 50 |
| IX | 3-40 | 50 |
| X | 3-40 | 50 |
| XI | 3-40 | 50 |
| XII | 3-40 | 50 |
| XIII | 3-40 | 50 |
| XIV | 3-40 | 50 |
| XV | 3-40 | 50 |
| XVI | 3-40 | 37 |
| EBP bisetanolamine salt form | | |
| I | 3-40 | 50 |
| II | 3-40 | 50 |
| III | 3-40 | 50 |
| EBP monoetanolamine salt form | | |
| H | 3-40 | 50 |
| E | 3-40 | 50 |

B. DSC Method

DSC analysis was performed on Q 1000 MDSC TA instruments with heating rate of 10° C./min, under nitrogen flow of 50 ml/min. Standard aluminum, closed pan (with hole) was used, sample mass was about 1-5 mg.

C. GC Method (i) Equipment

Apparatus: Capillary Gas Chromatography instrument equipped with autosampler, split/splitless injector and flame-ionization detector Capillary column: DB-WAX (USP G14), 30 m×0.53 mm, 1 μm or demonstrated equivalent Suitable data acquisition system Analytical balance 0.01 mg (ii) Reagents and Standards All reagents and standards are chromatographic grade. If chromatographic grade is not available, A.C.S. grade or any suitable grade that is available can be used.

Dimethylsulfoxide (DMSO), p.a.
Tetrahydrofurane, p.a.
Methanol, p.a.
Ethanol, p.a.
Acetic acid, p.a.

GC conditions

| | |
|---|---|
| Column temperature: | 50° C. isothermal for 5 minutes |
| | 50° C. 230° C. at 20° C./min |
| | 230° C. isothermal for 40 minutes |
| Injector temperature: | 250° C. |
| Detector temperature: | 280° C. |
| Detector: | FID |
| Carrier: | He (or N₂) at |
| | 4 mL/min (const. pressure at about 10 psi) |
| Split ratio: | 2:1 |

(iii) Preparation of Solutions:

Blank solution (B): Place DMSO into a vial.

Working standard solution (WS): Place a portion of DMSO into a 10 mL volumetric flask. Weigh, on a balance with 0.01 mg precision, about 150 mg (190 μL) of methanol, about 36 mg (41 μL) of tetrafuran standard, about 250 mg (316 μL) of ethanol standard and about 250 mg (316 μL) of acetic acid standard in the volumetric flask. Dilute to volume with DMSO and mix well.

Standard solution (STD): Place a portion of DMSO into a 100 mL volumetric flask. Pipette 1.0 mL of above prepared working standard solution (WS) and dilute to volume and mix well. Pipette standard solution (STD) into a vial.

Test solution (T): Weigh, on a balance with 0.01 mg precision, about 250 mg of sample into a 5 mL volumetric flask and dilute to volume. Pipett solution into vial.

D. Solid State $^{13}$CNMR Method $_{13}$C NMR at 125 MHz using Bruker Avance 11+500 SB probe using 4 mm rotors Magic angle was set using KBr Homogeneity of magnetic field checked using adamantane Parameters for Cross polarization optimized using glycine Spectral reference set according to glycine as external standard (176.03 ppm for low field carboxyl signal)

EXAMPLES

Example 1

Preparation of Crude Eltrombopag

3'-Amino-2'-hydroxybiphenyl-3-carboxylic acid ("BPCA") Form I (90 g, 392.6 mmol), was added slowly with stirring at room temperature to a solvent mixture of tech. methanol (1.8 L) and 4 M hydrochloric acid (0.245 L, 981.5 mmol) in 3 L reactor. The resulting red solution was stirred for thirty minutes. The solution was then cooled to 0-5° C. and a cold solution of sodium nitrite (27 g, 391.3 mmol) in 90 mL of water was added over twenty minutes such that the reaction mixture temperature did not rise above 10° C. The reaction mixture was stirred for one hour at 5-10° C. Sulfamic acid (4 g, 41.2 mmol) in 90 mL of water was added at 5° C. and the resulting mixture was stirred for additionally one hour at the same temperature. The reaction mixture was warmed to room temperature and triethylamine (ca 104 mL) was added to adjust pH 7-8. 1-(3,4-dimethylphenyl)-3-methyl-1H-pyrazol-5-ol ("pyrazole") form I (72 g, 357.8 mmol), was added in one portion to the reaction mixture and the resulting mixture was stirred for additionally two hours at room temperature. Hydrochloric acid (4M, ca 140 mL) was slowly added with stirring over twenty minutes to adjust pH to 1.8. A solid precipitated and was collected by filtration, washed with of mixture MeOH:water (1:1, 100 mL) and dried at 40° C./0 bar in vacuum oven for about 18 hours giving 151 g of crude orange to brown crystals of Eltrombopag crude (XRPD: form III with small percentage (less than 10%) of form I. (HPLC: 98.5%, Yield=95.4%)

Example 2

Preparation of Crystalline Eltrombopag Form I

A mixture of Eltrombopag Form I and Form III (500 mg) was suspended in acetone (30 mL) and heated to 57° C. Water (10 mL) was added and the resulting suspension was left to cool to reach a temperature of 22° C. The precipitate was filtered and dried for 1 h at 50° C./5 mbar to yield 314 mg.

Example 3

Preparation of Crystalline Eltrombopag Form I

A mixture of Eltrombopag Form I and Form III, (230 mg) was dissolved in 25 mL of glacial acetic acid (99.5%) while heating. The hot solution was then filtered and left to crystallize while cooling in an ice bath. The obtained product was collected by filtration and dried at 35° C. under vacuum. 139 mg of bright orange product was obtained.

Example 4

Preparation of Crystalline Eltrombopag Form I

Eltrombopag Form III (96 mg) was dissolved in 10 mL of glacial acetic acid (99.5%) while heating to boiling point of glacial acetic acid (118° C.). The hot solution was then filtered and left to crystallize while cooling to room temperature (23° C.). The obtained product was collected by filtration and dried at 35° C., under vacuum. 40 mg of bright orange product was obtained.

Example 5

Preparation of Chemically Pure Crystalline Eltrombopag Form I

Eltrombopag form III (24.42 g, HPLC purity: 98%) was suspended in 470 ml of glacial acetic acid (>99.5%) in a 1 L reactor. The suspension was stirred for five hours under reflux, then cooled to 40° C. and stirred for one hour at the same temperature. Crystals formed and were filtrated off, washed with 100 mL of methanol:water (1:1) and dried at 60° C./0 mbar for twelve hours yielding 20.49 g orange solid of Eltrombopag form I (Yield=88%; HPLC purity: 99.94%).

Example 6

Preparation of Chemically Pure Crystalline Eltrombopag Form I—Large Scale

Crude Eltrombopag (151 g, HPLC purity: 98.5%) was suspended in 2.9 L of glacial acetic acid in 3 L reactor. The suspension was stirred for five hours under reflux and cooled to 40° C. Crystals formed and were filtrated off, washed with 200 mL of methanol:water (1:1) and dried at 60° C./0 mbar overnight yielding 133 g orange solid of pure 3'-{N'-[1-(3,4-Dimethylphenyl)-3-methyl-5-oxo-1,5-dihydro-pyrazol-4-ylidene]hydrazino}-2'-hydroxybiphenyl-3-carboxylic acid (HPLC: 99.8%; XRPD: form I) (Yield=88%). PXRD analysis provided the diffractogram as shown in FIG. 1. DSC analysis provided the thermogram as shown in FIG. 2

Example 7

Preparation of Crystalline Eltrombopag Form III

Eltrombopag (210 mg) was dissolved in 15 mL of EtOAc while heating at reflux (77° C.). The hot solution was then filtered and left to crystallize while cooling in an ice bath (0-5° C.). The obtained product was collected by filtration and dried overnight at 22° C. 82 mg of bright orange product was obtained. PXRD analysis provided the diffractogram as shown in FIG. 3. DSC analysis provided the thermogram as shown in FIG. 4.

Example 8

Preparation of Crystalline Eltrombopag Form Iv

Eltrombopag (500 mg) Form I was suspended in MeOH/water mixture 1:3 (40 mL) and heated to 80° C. The suspension was left to cool to 22° C. The precipitate was filtered, washed with MeOH and air dried on air over night to yield 321 mg. PXRD analysis provided the diffractogram as shown in FIG. 5.

Example 9

Preparation of Crystalline Eltrombopag Form V

A mixture of Eltrombopag Form I and Form III (500 mg) was dissolved in THF (10 mL) and mixture of water/MeOH (1:1, 10 mL) was added dropwise. The precipitate was filtered and dried for 2 h at 50° C./5 mbar to yield 340 mg.

Example 10

Preparation of Crystalline Eltrombopag Form V

A mixture of Eltrombopag Form I and Form III (500 mg) was dissolved in THF (10 mL) and water (10 mL) was added dropwise. The solution was stirred 1 hour during which a precipitate was formed. The precipitate was filtered, washed with THF/water (1:1, 10 mL) and dried for 2 h at 50° C./5 mbar to yield 423 mg.

Example 11

Preparation of Crystalline Eltrombopag Form V

Eltrombopag (8.65 g) was dissolved in THF (50 mL) with heating to reflux. Water (50 mL) was added dropwise and the solution was stirred for 1 hour at 22° C. during which a precipitate was formed. The precipitate was filtered, washed with water and dried for 2 h at 50° C./5 mbar to yield 7.70 g. PXRD analysis provided the diffractogram as shown in FIG. 7. DSC analysis provided the thermogram as shown in FIG. 8

Example 12

Preparation of Crystalline Eltrombopag Form V

Eltrombopag Form VIII (1.092 g) was dissolved in 6.4 mL of THF while heating at 60° C. When a clear solution was obtained, 6.4 ml of $H_2O$ was added and reaction mixture was stirred for 1 hour at 22° C. A solid precipitated and was filtered, washed with $H_2O$, and dried at 50° C. under vacuum, 1 hour. 1.023 g of bright orange product was obtained.

Example 13

Preparation of Crystalline Eltrombopag Form Vi

Eltrombopag Form V (2 mg) was placed in aluminum sample pan with a small hole on lid under nitrogen pouring at a flow rate of 35 ml/min. The sample was equilibrated at 20° C., heated with heating rate of 10° C. per minute up to 120° C. The sample was cooled with a rate of 10° C./min up to 20° C. The prepared sample was measured by XRPD and a unique pattern was obtained. PXRD analysis provided the diffractogram as shown in FIG. 9.

Example 14

Preparation of Crystalline Eltrombopag Form VII

Eltrombopag Form V (2 mg) was placed in aluminum sample pan with a small hole on lid under nitrogen pouring at a flow rate of 35 ml/min. The sample was equilibrated at 20° C., heated with heating rate of 10° C. per minute up to 213° C. The DSC was calibrated with indium. The sample was cooled at a rate of 10° C./min up to 20° C. Prepared sample was measured by XRPD and a unique pattern was obtained. PXRD analysis provided the diffractogram as shown in FIG. 10.

Example 15

Preparation of Crystalline Eltrombopag Form VIII

Eltrombopag Form IV (500 mg) was suspended in dichloromethane (10 mL) and water (5 mL). The suspension was basified with NaOH, 1M (2.5 mL) and then acidified with HCl, 1M (2.5 mL). The solid was filtered off and dried in a vacuum oven for ½ h on 50° C./5 mbar. PXRD analysis provided the diffractogram as shown in FIG. 11. DSC analysis provided the thermogram as shown in FIG. 12.

Example 16

Preparation of Eltrombopag ethanolamine according to US 2006/0178518 A1, Example 1

Eltrombopag crude orange solid (1 g) was stirred in 16.75 ml of THF at approximately 30° C. Water (2.0 ml) was added slowly so as to maintain a temperature greater then 28° C. When addition was complete, the temperature was returned to 30° C. and the solution filtered through a glass fiber pad (2× Whatman GFC filters) to remove particulate matter. The filter was washed through with THF (2.0 ml) which was added to the filtrate. The filtrate was allowed to cool to room temperature. Ethanolamine (0.324 g, 2.35 mol. equiv.) was dissolved in IMS (26 ml) at 22° C. and stirred under a nitrogen atmosphere at 22° C. The filtrate containing the free acid was added to the ethanolamine solution over 20 to 30 minutes. The resulting dark red suspension was stirred for 3 hours and the solid isolated by filtration and dried at 50° C. in a vacuum oven over night to yield 1.22 g (96%) of the title compound.

Example 17

Preparation of Crystalline Eltrombopag Form IX

Eltrombopag form I (15-20 mg) was dissolved in THF (2 mL) with heating and left at 22° C. Obtained crystals were analyzed by XRD powder analysis. PXRD analysis provided the diffractogram as shown in FIG. 13.

Example 18

Preparation of Crystalline Eltrombopag Form X

Eltrombopag form I (15-20 mg) was dissolved in DMSO (2 mL) with heating and left at 22° C. Obtained crystals were analyzed by powder XRD analysis. PXRD analysis provided the diffractogram as shown in FIG. 14.

Example 19

Preparation of Crystalline Eltrombopag Form XI

Eltrombopag form I (15-20 mg) was dissolved in acetone (6 mL) with heating, filtered and left at 22° C. Obtained crystals were analyzed by powder XRD. PXRD analysis provided the diffractogram as shown in FIG. 15.

Example 20

Preparation of Crystalline Eltrombopag Form XII

Eltrombopag form I (15-20 mg) was dissolved in methoxybenzene (anisol) (6 mL) with heating. Solution was left at 22° C. Obtained crystals were analyzed by powder XRD. PXRD analysis provided the diffractogram as shown in FIG. 16.

Example 21

Preparation of Crystalline Eltrombopag Form XIII

Eltrombopag form I (15-20 mg) was dissolved in diethyl ether (6 mL), with heating, filtered and left at 22° C. Obtained crystals were analyzed by powder XRD. PXRD analysis provided the diffractogram as shown in FIG. 17.

Example 22

Preparation of Crystalline Eltrombopag Form XIV

Eltrombopag form I (15-20 mg) was dissolved in ethyl acetate (6 mL) with heating, filtered and left at 22° C. Obtained crystals were analyzed by powder XRD. PXRD analysis provided the diffractogram as shown in FIG. 18.

Example 23

Preparation of Crystalline Eltrombopag Form XV

Eltrombopag form X (2 mg) was placed in a DSC and was heated to a temperature of 160° C., under $N_2$. The prepared sample was measured by XRPD. PXRD analysis provided the diffractogram as shown in FIG. 19.

Example 24

Preparation of Amorphous Eltrombopag Bisethanolamine Salt

About 0.1 g of Eltrombopag bisethanolamine was grinded in Fritsch, Pulverisette 7, ball mill. Sample was grinded in 12 mL agate container with 7 agate balls (10 mm in diameter) with speed rate of 650 rpm. Amorphous sample was obtained after 1 h, 2 h and 3 hours of dry grinding. XRPD and DSC are given in FIG. 22 and FIG. 23.

Example 25

Preparation of Crystalline Eltrombopag Bisethanolamine Salt Form II

About 0.1 g of amorphous Eltrombopag bisethanolamine was grinded with additional 0.5 ml of methyl tert-butyl ether in Fritsch, Pulverisette 7, ball mill. Sample was grinded in 12 mL agate container with 6 agate balls (10 mm in diameter) with speed rate of 700 rpm. Crystalline sample was obtained after 1 h of grinding. Continuing the experiment, additional 0.5 ml of methyl tert-butyl ether was added in the same container after 1 hour and again after 2 hours of grinding in order to enhance material crystallinity. Raw data for XRPD and DSC measurements of the sample obtained after 3 hours of grinding are given in FIGS. 24 and 25, respectively.

Example 26

Preparation of Crystalline Eltrombopag Bisethanolamine Salt Form III

About 0.2 g of amorphous Eltrombopag bisethanolamine was slurried with about 3 ml of cumen solvent for about one day. The resulting red suspension was dried in the air at ambient temperature of about 25° C. Raw data for XRPD and DSC measurements of the sample obtained are given in FIGS. 24 25, respectively.

Example 27

Preparation of Crystalline Eltrombopag Bisethanolamine Salt Form I

Eltrombopag (2.48 g) was suspended in 50 ml of ethanol. The reaction mixture was refluxed and 3.4 ml of ethanolamine was added dropwise to the suspension. The mixture was refluxed for 45 minutes and was cooled down to 0° C. over 1.5 hr. The resulting crystals were filtered off. 2.9 g of purple crystals was obtained. Yield 91.0%

Example 28

Preparation of Crystalline Eltrombopag Bisethanolamine Salt Form I

Ethanolamine (3.1 ml) was added to 55 ml of absolute ethanol and refluxed. 2.27 g of eltrombopag was added portionwise over 10 minutes. The resulting mixture was refluxed for 30 minutes and then was cooled down to 0° C. over 1.5 hr. The resulting suspension was stirred at 20° C. overnight. Crystals formed and were filtered off. 2.75 g of purple crystals was obtained. Yield 94.8%.

Example 29

Preparation of Crystalline Eltrombopag Bisethanolamine Salt Form I

Methanolic HCl acid (22 ml, 1.25 M), 50 ml methanol and 2.5 g BPCA (2',3'-dihydroxybiphenyl-3-carboxylic acid) were stirred and cooled down to 0-5° C. at which point 0.770 g $NaNO_2$ (dissolved in 3 ml water) was added dropwise. The resulting solution was stirred at 0-5° C. for 30 min., and then 2 ml of conc. HCl acid were added dropwise. The resulting solution was stirred at 0-5° C. for 30 min. followed by addition of 40 mg sulfamic acid (dissolved in 3 ml water). The resulting reaction mixture was stirred for 45 min at 5-25° C. followed by addition 2.2 g of 1-(3,4-dimethylphenyl)-3-methyl-1,2-dihydropyrazol-5-one. The resulting solution was stirred for 10-15 min at room temperature and 4 ml of ethanolamine was added. The resulting suspension was stirred for 45 min, followed by filtration. 4.56 g of purple powder was obtained. Yield 74.15%

Example 30

Preparation of Crystalline Eltrombopag Bisethanolamine Salt Form I

Eltrombopag (1.0 g; 2.26 mmol) was dissolved in THF (17 mL) at room temperature. Water (2 mL) and additional THF (2 mL) were added and the solution was filtered. Ethanolamine (0.32 mL; 5.31 mmol) was dissolved in ethanol, p.a. (26 mL) and stirred under $N_2$ atmosphere. Eltrombopag solution was added dropwise to the ethanolamine/ethanol mixture over 25-30 minutes. The resulting reaction mixture was stirred for 3 hours under $N_2$ atmosphere. The precipitate was filtered and dried for 3 h at 50° C./5 mbar to yield 1.01 g (79%) of dark brown solid.

Example 31

Preparation of Crystalline Eltrombopag Bisethanolamine Salt Form I

Eltrombopag (1.0 g; 2.26 mmol) was dissolved in THF (30 mL) with stirring at room temperature and under $N_2$ atmosphere. Ethanolamine (1.4 mL; 23 mmol) was added to the THF solution and the resulting reaction mixture was stirred under $N_2$ atmosphere for 1.5 h. A precipitate formed and was filtered, washed with THF (2×2 mL) and dried for 3 h at 50° C./5 mbar to yield 1.20 g (94%) of purple brown solid.

Example 32

Preparation of Crystalline Eltrombopag Bisethanolamine Salt Form I

Eltrombopag (9 g; 20 mmol) was dissolved in THF (270 mL) with stirring at RT and under $N_2$ atmosphere. Ethanolamine (3.0 mL; 50 mmol) was added to the THF solution and the resulting reaction mixture was stirred under $N_2$ atmosphere for 1.5 h. A precipitate formed and was filtered, washed with THF and dried for 3 h at 20° C./5 mbar and for 18 h at 50° C./5 mbar to yield 10.0 g (89%) of purple brown solid.

Example 33

Preparation of Crystalline Eltrombopag Bisethanolamine Salt Form I

Eltrombopag (1.67 g; 3.78 mmol) was dissolved in THF (30 mL) and the solution filtered. Ethanolamine (2.28 mL; 37.8 mmol) was dissolved in ethanol, p.a. (50 mL) and heated to reflux. When the ethanol started to distill, the THF solution was added dropwise into the ethanolamine solution over 20 minutes via an addition funnel. The addition was additionally washed with THF (2×1.7 mL). The resulting reaction mixture was refluxed for 0.5 h under $N_2$ atmosphere. The heating was discontinued and the stirring was continued for 5 h. A precipitate formed and was filtered, washed with EtOH (2×4 mL) and dried for 18 h at 22° C./5 mbar and for 2 h at 50° C./5 mbar to yield 1.4 g (66%) of golden brown solid.

Example 34

Preparation of Crystalline Eltrombopag Bisethanolamine Salt Form I

Eltrombopag form III (1.0 g; 2.26 mmol) was suspended in MeOH (20 mL) and heated to reflux. Ethanolamine (1.36 mL; 22.6 mmol) was added to the resulting suspension and the resulting reaction mixture was stirred at reflux for 0.5 h. The heating was discontinued and the reaction mixture reached 25° C. in 2 hours with stirring. The suspension was cooled to 0° C. and stirred for 0.5 h. The precipitate was filtered, washed with cold MeOH (2×5 mL) and dried for 15 h at 50° C./5 mbar to yield 1.06 g (83%) of purple crystals.

Example 35

Preparation of Crystalline Eltrombopag Bisethanolamine Salt Form I

Eltrombopag form I (5.7 g; 12.9 mmol) was suspended in MeOH (114 mL) and heated to reflux. Ethanolamine (7.8 mL; 129 mmol) was dissolved in MeOH (28.5 mL) and added dropwise to the Eltrombopag suspension over 5 minutes. The resulting reaction mixture was stirred at reflux for 0.5 h and at r.t. for 19 h. The precipitate was filtered, washed with MeOH (100 mL) and dried for 2 h at 50° C./5 mbar to yield 5.39 g (74%) of purple crystals.

Example 36

Preparation of Crystalline Eltrombopag Bisethanolamine Salt Form I

A mixture of Eltrombopag form I and form V (3.5 g; 7.92 mmol) was suspended in EtOH (70 mL) and heated to reflux. Ethanolamine (4.8 mL; 79.6 mmol) was dissolved in EtOH (17.5 mL) and added dropwise to the Eltrombopag suspension over 15 minutes. The resulting reaction mixture was stirred at reflux for 0.5 h, cooled to 0° C. in 1.5 h and stirred for additional 0.5 h. The precipitate was filtered, washed with EtOH (3×10 mL) and dried for 1.5 h at 50° C./5 mbar to yield 3.71 g (83%) of purple crystals.

Example 37

Preparation of Crystalline Eltrombopag Mono-Ethanolamine Salt Form H

Eltrombopag bisethanolamine (15-20 mg) was dissolved in 5 mL of 1-butanol with heating to 70° C. and left to crystallize at 22° C. Precipitate was analysed.

Example 38

Preparation of Crystalline Eltrombopag Mono-Ethanolamine Salt Form H

Eltrombopag (15-20 mg) bisethanolamine was dissolved in 5 mL of 1-pentanol with heating to 70° C. and then was left to crystallize at 22° C. A precipitate formed and was separated by filtration and analysed. PXRD analysis provided the diffractogram as shown in FIG. 29.

Example 39

Preparation of Crystalline Eltrombopag Mono-Ethanolamine Salt Form E

Amorphous Eltrombopag bisethanolamine (0.5 g) was placed in a desiccator containing the atmosphere of 2,2,2-trifluoroethanol. After 7 days, a yellow to orange sample was removed from the desiccator and air dried at temperature of about 25° C. for about 24 hours. PXRD analysis provided the diffractogram as shown in FIG. 30.

Example 40

Preparation of Crystalline Form II of Eltrombopag Bisethanolamine in a Mixture with Form I of Eltrombopag Bisethanolamine Ethanolamine, (1.0 mL; 16.6 mmol) was dissolved in n-propyl acetate at room temperature. Eltrombopag (1.5 g; 3.39 mmol) was dissolved in THF (20 mL) at room temperature, the resulting solution filtered into an addition funnel and added thereby into the ethanolamine solution. The addition funnel was additionally washed with THF (10 mL). The reaction mixture was stirred at room temperature for 1 h. A solid formed and was filtered and the reactor washed with THF (30 mL). The precipitate was washed with THF (10 mL) and dried at 50° C./5 mbar for 2.5 h to yield 1.78 g (93%) of purple solid EBP olamine.

Example 41

Preparation of Crystalline Form II of Eltrombopag Bisethanolamine in a Mixture with Form I of Eltrombopag Bisethanolamine Eltrombopag, Form V, (50 mg) was dissolved with heating in 1,4-dioxane (3 mL). Ethanolamine was added (0.05 mL) and the flask was closed and left at room temperature. A precipitate formed and was analyzed by XRPD.

Example 42

Preparation of Crystalline Form II of Eltrombopag Bisethanolamine in a Mixture with Form I of Eltrombopag Bisethanolamine Amorphous Eltrombopag ethanolamine was slurried with tert-butylmethyl ether (TMBE) over the period of 1 hour. Eltrombopag bisethanolamine form II and amorphous were detected. The mixture was further slurried and Eltrombopag bisethanolamine Form I was also detected. After 3 days of slurrying a stable suspension of Eltrombopag bisethanolamine Form I and II was obtained, with higher amount of form II then form I.

Example 43

Preparation of Crystalline Form II of Eltrombopag Bisethanolamine in a Mixture with Form I of Eltrombopag Bisethanolamine A mixture of Form II and Form I of eltrombopag bisetanolamine was prepared by slow crystallisation of amorphous Eltrombopag bisethanolamine in atmosphere of 1-octanol over the period of about 12 days.

Example 44

Preparation of Crystalline Form II of Eltrombopag Bisethanolamine in a Mixture with Form I of Eltrombopag Bisethanolamine A mixture of Form II and Form I of eltrombopag bisetanolamine was prepared by solvent drop grinding of amorphous Eltrombopag bisethanolamine with 1-octanol. About 0.1 g of amorphous Eltrombopag olamine was ground with additional few drops of 1-octanol in Fritsch, Pulverisette 7, ball mill. The sample was ground in 12 mL agate container with 6 agate balls (10 mm in diameter). After 2 hours of grinding (700 rpm) Form II was detected.

Example 45

Preparation of Crystalline Form II of Eltrombopag Bisethanolamine in a Mixture with Form I of Eltrombopag Bisethanolamine Eltrombopag bisethanolamine form II in a mixture with amorphous Eltrombopag bisethanolamine was obtained by very strong grinding of amorphous EBP with a few drops of water after three hours of grinding. About 0.1 g of amorphous Eltrombopag bisethanolamine was ground with an additional 0.5 ml of water in Fritsch, Pulverisette 7, ball mill. The sample was ground in 12 mL agate container with 6 agate balls (10 mm in diameter). Duration of grinding: 1 h (650 rpm)+1 h (800 rpm)+1 h (800 rpm)→XRPD.

Example 46

Preparation of Pure Crystalline Form II of Eltrombopag Bisethanolamine

Pure Form II of eltrombopag bisetanolamine was prepared by slow crystallization of amorphous Eltrombopag bisethanolamine in an atmosphere of TMBE over the period of 1 month and more at room temperature.

Example 47

Preparation of Crystalline Eltrombopag Form XVI

Crystalline 3'-amino-2'-hydroxybiphenyl-3-carboxylic acid form II (50 g, 218 mmol, PXRD pattern at FIG. 34) (Supplier: Topharman Shangai Co., Ltd; Batch No: BPCA: 090921 BPCA) was added to a solvent mixture of methanol (1 L) and hydrochloric acid, 4 M (137 mL) in a 1 L reactor with stirring at room temperature (cca 22° C.). The resulting solution was stirred for ½ h and then cooled to 0-5° C. A refrigerated solution of sodium nitrite (15 g, 217 mmol) in water (50 mL) was added to the reaction mixture over 20 min (maintaining the reaction temperature below 10° C.) and the stirring was continued for 1 h. A Solution of sulfamic acid (2.22 g, 23 mmol) in water (50 mL) was added to the reaction mixture and stirred for 1 h at 5° C. The resulting reaction mixture was heated to room temperature and triethylamine (cca 80 mL) was added to adjust to pH 7-8. Crystalline 1-(3, 4-dimethylphenyl)-3-methyl-1H-pyrazol-5-ol ("pyrazole") form II (44 g, 218 mmol, PXRD pattern at FIG. 33) (Supplier: Topharman Shangai Co., Ltd; Batch No: 090805PYRAZOL) was added in one portion to the reaction mixture and stirred for 2 h at room temperature, maintaining the pH 7-8. Hydrochloric acid (4 M, cca 40 mL) was added to adjust the pH to 1.8 over 20 minutes with stirring. The precipitated solid was filtered, washed with mixture of MeOH:water (1:1, 60 mL) and dried at 40° C./5 bar for about 18 h to yield 100 g (90%) of EBP as a bright orange powder. PXRD analysis provided the diffractogram as shown in FIG. 20. DSC analysis provided the thermogram as shown in FIG. 21

Example 48

Figure 32:
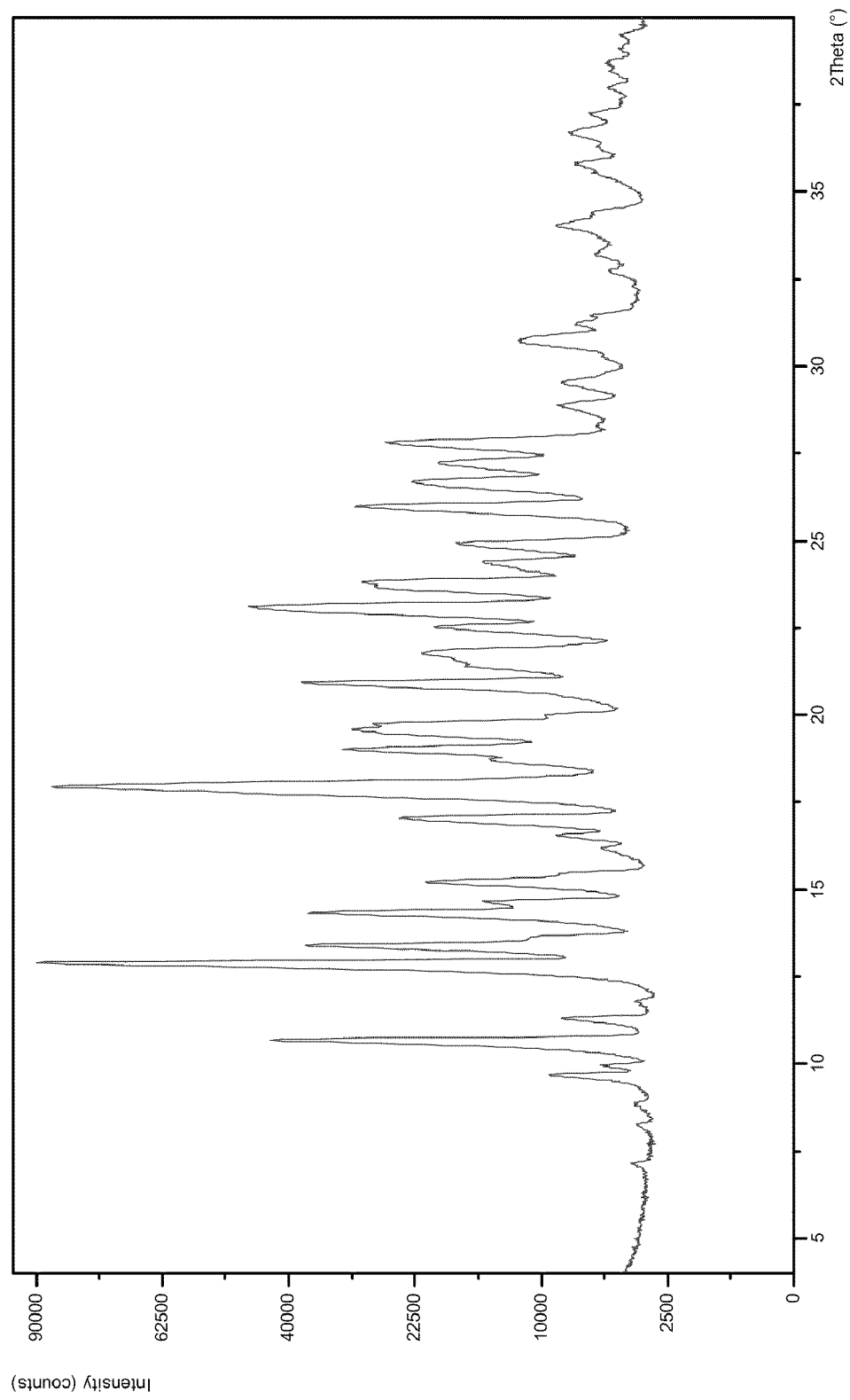
FIG. 32 shows a powder XRD pattern of crystalline 3'-amino-2'-hydroxybiphenyl-3-carboxylic acid ("BPCA") form I.

Preparation of crystalline 3'-amino-2'-hydroxybiphenyl-3-carboxylic acid ("BPCA") form I according to IPCOM000180992D A solution of 2'-hydroxy-3'-nitrobiphenyl-3-carboxylic acid (800 g, 3.2 mol) in methanol (5 L) was hydrogenated over 5% Pd/C (160 g) at room temperature for 8 hours. The reaction mixture was filtered, concentrated and slurried in THF (2.5 L) to give 3'-amino-2'-hydroxybiphenyl-3-carboxylic acid (690 g, 50.5%) as a brown solid. PXRD analysis provided the diffractogram as shown in FIG. 32.

Example 49

Preparation of crystalline 1-(3,4-dimethylphenyl)-3-methyl-1H-pyrazol-5-ol ("pyrazole") form I according to IPCOM000180992D 2-(3,4-Dimethylphenyl)hydrazinium chloride (900 g, 5.21 mol), ethyl acetoacetate (678 g, 5.21 mol), sodium acetate (428 g, 5.21 mol) and glacial acetic acid (10 L) were stirred at 118° C. for about 24 hours. The resulting mixture was cooled and concentrated, and the residue was dissolved in dichloromethane (10 L) and carefully washed with saturated sodium bicarbonate (3×3 L). The organic layer was concentrated to afford a solid. The solid was dissolved in ethanol (450 mL) under reflux. Petroleum ether (7.2 L) was slowly added, and the resulting mixture was cooled and filtered to afford the title compound (748 g, 71%). PXRD analysis provided the diffractogram as shown in FIG. 31.

Example 50

Preparation of Eltrombopag Bisetanolamine Form I with Low Content of Ethanol

Ethanolamine (24 mL, 0.4 mol) was mixed with ethanol (600 mL) in a 1 L reactor. The mixture was heated to 65° C. and Eltrombopag cryst (40 g, 0.08 mol) was added. The resulting reaction mixture was heated to reflux and stirred for half an hour. The suspension was then cooled to 25° C. A precipitate formed and was filtered off and washed with ethanol (100 mL). The solid was then dried at 50° C./5 mbar to weight loss <0.5% giving 42 g dark purple crystal of EBP olamine (XRPD: form I) (Yield=92%; GC residual EtOH=0.24%).

Example 51

Preparation of (Z)-methyl 3'-(2-(1-(3,4-dimethylphenyl)-3-methyl-5-oxo-1H-pyrazol-4(5H)-ylidene)hydrazinyl)-2'-hydroxybiphenyl-3-carboxylate (ETP impurity 1)

Pure 3'-{N'-[1-(3,4-Dimethylphenyl)-3-methyl-5-oxo-1,5-dihydro-pyrazol-4-ylidene]hydrazino}-2'-hydroxybiphenyl-3-carboxylic acid (Eltrombopag) (20 g, 0.045 mol) was suspended in a mixture of MeOH/THF=1/1 (400 mL). The suspension was heated to reflux and sulfuric acid (5 mL) was added drop wise. The reaction mixture was refluxed overnight, cooled to room temperature and evaporated to obtain an oily residue. Water (200 ml) was added to the and a thick suspension was formed. EtOAc (200 ml) was added to form a 2-phase system and the layers were separated. The organic layer was left for half an hour at room temperature resulting in formation of orange crystals. The crystals were filtered, washed with 2×20 mL EtOAc and dried in a vacuum oven at 35° C./0 bar for 2 hours, giving 17.17 g of (Z)-methyl 3'-(2-(1-(3,4-dimethylphenyl)-3-methyl-5-oxo-1H-pyrazol-4(5H)-ylidene)hydrazinyl)-2'-hydroxybiphenyl-3-carboxylate (Yield: 83.3%); (HPLC: >95%)

Example 52

Preparation of ((Z)-3'-(2-(1-(3,4-dimethylphenyl)-3-methyl-5-oxo-1H-pyrazol-4(5H)-ylidene)hydrazinyl)-2'-hydroxybiphenyl-3-carboxamide (ETP impurity 2)

Step a: Preparation of (Z)-3'-(2-(1-(3,4-dimethylphenyl)-3-methyl-5-oxo-1H-pyrazol-4(5H)-ylidene)hydrazinyl)-2'-hydroxybiphenyl-3-carbonyl chloride Thionyl chloride (5 mL, 68.5 mmol) was added to a solution of pure 3'-{N'-[1-(3,4-Dimethylphenyl)-3-methyl-5-oxo-1,5-dihydro-pyrazol-4-ylidene]hydrazino}-2'-hydroxybiphenyl-3-carboxylic acid (Eltrombopag form I) (5 g, 11 mmol) in dry THF (75 mL) followed by addition of DMF (0.5 mL) at room temperature in three-necked flask. The reaction mixture was stirred for one hour and additional thionyl chloride (5 mL, 68.5 mmol) and DMF (0.5 mL) were added. The precipitation of acyl chloride started in half an hour and heptane (90 mL) was added. The thick reaction suspension was stirred for further half an hour, filtrated and washed with 2×50 mL of heptane yielding 5 g of (Z)-3'-(2-(1-(3,4-dimethylphenyl)-3-methyl-5-oxo-1H-pyrazol-4(5H)-ylidene)hydrazinyl)-2'-hydroxybiphenyl-3-carbonyl chloride (Yield: 96%); (HPLC: 95%), that was immediately used for the next step.

Step b: Preparation of Z)-3'-(2-(1-(3,4-dimethylphenyl)-3-methyl-5-oxo-1H-pyrazol-4(5H)-ylidene)hydrazinyl)-2'-hydroxybiphenyl-3-carboxamide (ETP impurity 2)

(Z)-3'-(2-(1-(3,4-dimethylphenyl)-3-methyl-5-oxo-1H-pyrazol-4(5H)-ylidene)hydrazinyl)-2'-hydroxybiphenyl-3-carbonyl chloride (5 g, 10.9 mmol) was added portion wise (over one hour) to an NH₃/NMP solution (120 mL) and the resulting reaction mixture was cooled to 0° C. The cooled reaction mixture was stirred for one hour, then warmed to room temperature and EtOH (50 mL) was added followed by drop wise addition of 4 M HCl (100 mL). The resulting orange suspension was stirred for half an hour, filtered, washed with 2×50 mL EtOH. The filtered orange crystals were suspended in EtOAc (50 mL) and refluxed for 4 hours, then cooled to room temperature and 20 mL of MeOH/H₂O (1/1) were added. the resulting orange suspension was filtrated, washed with MeOH/H₂O=1/1 (30 mL) and dried in vacuum oven (0 bar/50° C.) for four hours giving 2.54 g of fluorescent orange crystals of Z)-3'-(2-(1-(3,4-dimethylphenyl)-3-methyl-5-oxo-1H-pyrazol-4(5H)-ylidene)hydrazinyl)-2'-hydroxybiphenyl-3-carboxamide (Yield: 50.9%; HPLC purity: 98%).

Example 53

Preparation of Eltrombopag Form I from Eltrombopag Form XVI

Eltrombopag acid, form XVI (27.3 g) was suspended in 525 mL of glacial acetic acid. The suspension was heated to reflux and stirred for two and a half hours at reflux. The suspension was then cooled to 40° C. The crystals formed in the process were filtered off and washed with methanol:water (1:1, 100 mL), and vacuum dried at 50° C. overnight. The process provided 22.08 g of an orange solid of Eltrombopag acid form I (Yield=80.9%).

What is claimed is:

1. Crystalline Eltrombopag Form I characterized by data selected from the group consisting of: a powder XRD pattern having peaks at 4.0, 7.3, 7.7, 12.1 and 16.1° 2θ±0.2° 2θ; a PXRD pattern as depicted in FIG. 1; a solid state $^{13}$C NMR spectrum having peaks at 166.9, 155.4, 134.1, 125.7 and 111.8 ±0.2 ppm; a solid state $^{13}$C NMR spectrum as depicted in FIG. 35; and any combination thereof.

2. The crystalline Eltrombopag according to claim 1, further characterized by data selected from the group consisting of: a powder XRD pattern having peaks at 8.8, 14.6, 17.6, 24.3 and 26.8° 2θ±0.2° 2θ; a DSC thermogram as depicted in FIG. 2; a solid state $^{13}$C NMR spectrum having peaks at 141.4, 130.4, 119.8 and 117.8±0.2 ppm; and any combination thereof.

3. The crystalline Eltrombopag according to claim 1, wherein the crystalline Eltrombopag is anhydrous.

4. Crystalline Eltrombopag Form I according to claim 1, characterized by a powder XRD pattern having peaks at 4.0, 7.3, 7.7, 12.1 and 16.1° 2θ±0.2° 2θ.

5. Crystalline Eltrombopag form III characterized by data selected from the group consisting of: a powder XRD pattern having peaks at 9.2, 11.2, 12.2 and 14.0° 2θ±0.2° 2θ; a PXRD pattern as depicted in FIG. 3; a solid state $^{13}$C NMR spectrum having peaks at 170.6, 128.7, 124.2 and 113.8±0.2 ppm; a solid state $^{13}$C NMR spectrum as depicted in FIG. 36; and any combination thereof.

6. The crystalline Eltrombopag according to claim 5, further characterized by data selected from the group consisting of: a powder XRD pattern having peaks at 5.3, 16.1, 22.4 and 24.3° 2θ±0.2° 2θ; a DSC thermogram as depicted in FIG. 4; a solid state $^{13}$C NMR spectrum having peaks at 155.0, 141.0, 136.6 and 133.6±0.2 ppm; and any combination thereof.

7. Crystalline Eltrombopag form III according to claim 5, characterized by a powder XRD pattern having peaks at 9.2, 11.2, 12.2 and 14.0° 2θ±0.2° 2θ.

8. Crystalline Eltrombopag Form V characterized by data selected from the group consisting of: a powder XRD pattern having peaks at 5.9, 8.2, 10.5 and 12.5° 2θ±0.2° 2θ; a PXRD pattern as depicted in FIG. 7; a solid state $^{13}$C NMR spectrum having peaks at 142.0, 131.6, 114.9 and 67.8±0.2 ppm; a solid state $^{13}$C NMR spectrum as depicted in FIG. 37; and any combination thereof.

9. The crystalline Eltrombopag according to claim 8, further characterized by data selected from the group consisting of: a powder XRD pattern having peaks at 5.3, 9.2, 14.0, 23.5 and 25.0° 2θ±0.2° 2θ; a DSC thermogram as depicted in FIG. 8; a solid state $^{13}$C NMR spectrum having peaks at 171.9, 155.4, 136.3 and 121.3 ±0.2 ppm; and any combination thereof.

10. Crystalline Eltrombopag Form V according to claim 8, characterized by a powder XRD pattern having peaks at 5.9, 8.2, 10.5 and 12.5° 2θ±0.2° 2θ.

11. Crystalline Eltrombopag form XVI characterized by a data selected from a group consisting of: a powder XRD pattern having peaks at 7.1, 9.5, 13.9, 21.2 and 25.5° 2θ±0.2° 2θ; a PXRD pattern as depicted in FIG. 20; a solid state $^{13}$C NMR spectrum having peaks at 168.7, 156.7, 127.6 and 112.8±0.2 ppm; a solid state $^{13}$C NMR spectrum as depicted in FIG. 38; and any combination thereof.

12. The crystalline Eltrombopag according to claim 11, characterized by data selected from the group consisting of: a powder XRD pattern having peaks at 5.9, 11.2, 15.4, 17.4 and 26.2° 2θ±0.2° 2θ; a DSC thermogram as depicted in FIG. 21; a solid state $^{13}$C NMR spectrum having peaks at 146.4, 140.7, 136.3 and 117.3±0.2 ppm; and any combination thereof.

13. Crystalline Eltrombopag form XVI according to claim 11, characterized by a powder XRD pattern having peaks at 7.1, 9.5, 13.9, 21.2 and 25.5° 2θ±0.2° 2θ.

14. A process for preparing Eltrombopag ethanolamine salt comprising preparing crystalline Eltrombopag according to any one of claims 1-13 and reacting the crystalline Eltrombopag with ethanolamine to obtain Eltrombopag ethanolamine salt.

15. The process according to claim 14, wherein the Eltrombopag ethanolamine salt has a total purity of at least about 99%.

16. A crystalline form of Eltrombopag according to claim 1, wherein at least one of (Z)-methyl 3'-(2-(1-(3,4-dimethylphenyl)-3-methyl-5-oxo-1H-pyrazol-4(5H)-ylidene)hydrazinyl)-2'-hydroxybiphenyl-3-carboxylate and (Z)-3'-(2-(1-(3,4-dimethylphenyl)-3-methyl-5-oxo-1H-pyrazol-4 (5H)-ylidene)hydrazinyl)-2'-hydroxybiphenyl-3-carboxamide is present in an amount from about 0.01% to about 0.1% as measured by HPLC.

17. A pharmaceutical formulation comprising a crystalline form of Eltrombopag according to any one of claims 1-13 and 16 and at least one pharmaceutically acceptable excipient.

* * * * *